United States Patent
Kietzmann et al.

(10) Patent No.: US 9,309,503 B2
(45) Date of Patent: Apr. 12, 2016

(54) PREPARATION OF AN ESTERASE

(75) Inventors: Martin Kietzmann, Graz (AT); Helmut Schwab, Graz (AT); Harald Pichler, Deutschlandsberg (AT); Mirela Ivancic, Sv. Nedjelja (HR); Oliver May, Aachen (DE); Rudolf Gijsbertus Marie Luiten, Leide (NL)

(73) Assignee: DPx Holdings B.V., Amsterdam (NL)

( * ) Notice: Subject to any disclaimer, the term of this patent is extended or adjusted under 35 U.S.C. 154(b) by 481 days.

(21) Appl. No.: 12/667,414

(22) PCT Filed: Jul. 4, 2008

(86) PCT No.: PCT/EP2008/058731
§ 371 (c)(1),
(2), (4) Date: Jul. 1, 2010

(87) PCT Pub. No.: WO2009/004093
PCT Pub. Date: Jan. 8, 2009

(65) Prior Publication Data
US 2011/0177553 A1 Jul. 21, 2011

(30) Foreign Application Priority Data

Jul. 4, 2007 (EP) .................................... 07013092
Jan. 17, 2008 (EP) .................................... 08000828

(51) Int. Cl.
*C12P 21/02* (2006.01)
*C12N 9/18* (2006.01)
*C12N 15/70* (2006.01)

(52) U.S. Cl.
CPC .................. *C12N 9/18* (2013.01); *C12N 15/70* (2013.01); *C12Y 301/01001* (2013.01)

(58) Field of Classification Search
USPC ........................................... 435/69.1, 252.33
See application file for complete search history.

(56) References Cited

U.S. PATENT DOCUMENTS

| | | | |
|---|---|---|---|
| 6,872,563 B1 | 3/2005 | Beckwith et al. | |
| 2004/0161836 A1 | 8/2004 | Bornscheur et al. | |
| 2010/0112662 A1* | 5/2010 | Bornscheuer et al. | 435/196 |
| 2010/0151541 A1* | 6/2010 | Steinbauer et al. | 435/135 |

FOREIGN PATENT DOCUMENTS

| | | |
|---|---|---|
| WO | 2004/055177 | 7/2004 |
| WO | 2007/073847 | 7/2007 |

OTHER PUBLICATIONS

Witkowski et al.; Conversion of beta-ketoacyl Synthase to a Malonyl Decarboxylase by Replacement of the Active-site Cysteine with Glutamine; Biochemistry 38:11643-11650, 1999).*
Seffernick et al.; Melanine Deaminase and Atrazine Chlorohydrolase: 98 percent Identical but Functionally Different; J. Bacteriol. 183(8):2405-2410, 2001).*
Branden et al.; Introduction to Protein Structure, Garland Publishing Inc., New York, p. 247 (1991)).*
International Search Report for PCT/EP2008/056841, mailed Oct. 7, 2008.
Written Opinion of the International Searching Authority for PCT/EP2008/056841, mailed Oct. 7, 2008.
Boettcher at al., "Functional Exprssion of the Gamma-Isoenzyme of PIG Liver Carboxyl Esterase in *Escherichia Coli*", Applied Microbiology and Biotechnology, Springer Verlag, Berlin, DE, vol, 73, No. 6, Sep. 8, 2006, pp. 1282-1289, XP002456633.
Kay, "Overview of Bacterial Expression Systems for Heterologous Protein Production; from Molecular and Biochemical Fundamentals to Commercial Systems", Applied Microbiology and Biotechnology, Springer-Verlag, BE, vol. 72, No. 2, Jun. 22, 2006, pp. 211-222, XP019422070.
S. Lange at al., "Cloning, Functional Expression, and Characterization of Recombinant Pig Lever Esterase", Chembiocem, vol. 2, 2001, pp. 576-582, XP002483884.
Matsushima et al., "The Nucleotide and Deduced Amino Acid Sequences of Porcine Liver Proline-Beta-Naphthylamidase. Evidence for the Identity with Carboxylesterase", FEBS Letters, Elsevier, Amsterdam, NL, vol. 293, No. 1-2, Nov. 18, 1991, pp. 37-41, XP002209303.
R. Novy et al., "Overcoming the Codon Bias of *E. coli* for Enhanced Protein Expression", Innovations, vol. 12, Jun. 2001, pp. 1-3, XP002483885.
Bessette et al., "Efficient Folding of Proteins with Multiple Disulfide Bonds in the *Escherichia coli* Cytoplasm", Proceedings of the National Academy of Sciences of USA, National Academy of Science, Washington, DC, vol. 96, No. 24, Nov. 23, 1999, pp. 13703-13708, XP002233564.
Bruesehaber et al., "Identification of Pig Liver Esterase Variants by Tandem Mass Spectroscopy Analysis and Their Characterization", Applied Microbiology and Biotechnology, Springer Verlag, Berlin, DE, vol. 76, Jun. 26, 2007, pp. 853-859, XP002456632.
Aslund et al., "Efficient Production of Disulfide Bonded Proteins in the Cytoplasm in Oxidizing Mutants of *E. coli*", Innovations, XX, XX, vol. 10, Nov. 1, 1999, pp. 11-12, XP002456634.
Prinz, W.A., Aslund, F., Holmgren, A. and Beckwith, J. (1997) J. Biol.Chem. 272: 15661-15667.
Balzer D, Ziegelin G, Pansegrau W, Kruft V, Lanka E. (1992). Nucleic Acids Res.20, 1851-1858.
Datsenko, K.A. & Wanner, B.L. (2000) PNAS 97, 6640-6645.

* cited by examiner

*Primary Examiner* — Anne Gussow
*Assistant Examiner* — Antonio Galisteo Gonzalez
(74) *Attorney, Agent, or Firm* — Pierce Atwood LLP; Raymond G. Arner

(57) ABSTRACT

The present invention relates to a recombinant *E. coli* strain characterized in that the organisms contains a gene coding for a protein having esterase activity. Such *E. coli* is suitable for the preparation of a protein with esterase activity, whereby the expression takes place without coexpression of GroEL and/or GroES from a plasmid. The expression of glutathione reductase and/or thioredoxin reductase may be abolished by mutation. Furthermore, the ability of the organism to grow under oxygen-rich conditions has been restored by mutation. The expression of the gene of the protein with esterase activity is unaccompanied by the expression of an additional gene encoding a heat shock chaperone protein.

18 Claims, 5 Drawing Sheets

PREPARATION OF AN ESTERASE

This application is the U.S. national phase of International Application No. PCT/EP2008/058731, filed 4 Jul. 2008, which designated the U.S. and claims priority to European Application No(s). 07013092.7, filed 4 Jul. 2007, and 08000828.7, filed 17 Jan. 2008, the entire contents of each of which are hereby incorporated by reference.

The present invention relates to a method for the preparation of a protein with esterase activity comprising expression of a gene encoding such a protein in an *Escherichia coli* (*E. coli*) strain.

High level expression of proteins with Pig Liver Esterase activity is not easily realized. Reports by Lange et al (2001) [1] indicate low but detectable production of the γ-isoenzyme of Pig Liver Esterase (γ-rPLE) in *Pichia pastoris*. More recently a method has been described by Böttcher et al. (2007) [2]. These authors showed that the expression of the γ-isoenzyme of Pig Liver Esterase (γ-rPLE) in an *E. coli* strain was not a straightforward process. Such expression failed completely if no additional measures were taken. These measures imply not only proper selection of a suitable *E. coli* strain, but also co-expression of chaperone proteins. In particular, preparation of functional γ-rPLE turned out to be possible only in the *E. coli* strain Origami, co-expressing considerable amounts of the chaperone proteins designated as GroEL and GroES.

At least part of the problems encountered in proper expression of γ-rPLE relates to the occurrence of multiple disulfide bonds in the protein.

Very surprisingly and against the teaching reported by Böttcher et al. (2007) [1] it was discovered according to the present invention that functional expression of a protein with pig liver esterase (PLE) activity could be achieved without the extensive additional measures disclosed by Böttcher et al. (2007) [1] and in particular without co-expression of additional genes.

Accordingly, the present invention relates to a method for the preparation of a protein with esterase activity comprising expression of a gene encoding such protein in an *E. coli* strain, characterized in that the gene encoding the protein with esterase activity has at least 70% identity, preferably at least 80% identity, preferably at least 85% identity, preferably at least 90% identity, preferably at least 95% identity, preferably at least 98% identity and most preferably at least 99% identity to SEQ ID NO 12, SEQ ID NO 33, SEQ ID NO 35, SEQ ID NO 37, SEQ ID NO 39, SEQ ID NO 41, SEQ ID NO 43 or SEQ ID NO 45, respectively. It is an advantage of the invention that correctly folded esterases are obtained, without the need to co-express GroEL and/or GroES from a plasmid. In a preferred embodiment the expression takes place without coexpression of GroEL and/or GroES from a plasmid.

In the framework of this invention, identity is calculated as described in Tatiana A. Tatusova, Thomas L. Madden (1999), "Blast 2 sequences—a new tool for comparing protein and nucleotide sequences", FEMS Microbial Lett. 174:247-250, using the following standard parameters at Hypertext Transfer Protocol Secure://world wide web ncbi.nlm.nih.gov/BLAST/bl2seq/wblast2.cgi for Protein sequences:
Matrix: BLOSUM62
Open gap: 5
extension gap: 2
Penalties gap x_dropoff: 11
Expected: 10
word size: 11
for nucleotide sequences:
Reward for match: 1
Penalty for mismatch: −2
Open gap: 11
extension gap: 1
Penalties gap x_dropoff: 50
Expected: 10
word size: 3

More preferably, the invention relates to a method for the preparation of a protein with esterase activity comprising expression of a gene encoding such protein in an *E. coli* strain, characterized in that the gene encoding the protein with esterase activity has at least 70% identity, preferably at least 80% identity, preferably at least 85% identity, preferably at least 90% identity, preferably at least 95% identity, preferably at least 98% identity and most preferably at least 99% identity to the polynucleotide of SEQ ID NO 11, and encodes a protein that has at least 80% identity, preferably at least 85% identity, preferably at least 90% identity, preferably at least 95% identity, preferably at least 98% identity, more preferably at least 99% identity to SEQ ID NO 12.

According to a further embodiment the present invention relates to a method for the preparation of a protein with esterase activity comprising expression of a gene encoding such protein in an *E. coli* strain, characterized in that the gene encodes a protein that has at least 80% identity, preferably at least 85% identity, preferably at least 90% identity, preferably at least 95% identity, preferably at least 98% identity, more preferably at least 99% identity to. SEQ ID NO 12. SEQ ID NO 12 represents the amino acid sequence of APLE.

According to another embodiment the present invention relates to a recombinant *E. coli* strain suitable for the preparation of a protein with esterase activity, characterized in that the organism contains a gene encoding the protein with esterase activity which has at least 70% identity, preferably 80% identity, more preferably at least 85% identity, preferably at least 90% identity, preferably at least 95% identity, preferably at least 98% identity and most preferably at least 99% identity to the polynucleotide of SEQ ID NO 11 SEQ ID NO 32, SEQ ID NO 34, SEQ ID NO 36, SEQ ID NO 38, SEQ ID NO 40, SEQ ID NO 42 or SEQ ID NO 44, and encodes a protein that has at least 80% identity, preferably at least 85% identity, preferably at least 90% identity, preferably at least 95% identity, preferably at least 98% identity, more preferably at least 99% identity to SEQ ID NO 12 SEQ ID NO 33, SEQ ID NO 35, SEQ ID NO 37, SEQ ID NO 39, SEQ ID NO 41, SEQ ID NO 43 or SEQ ID NO 45, respectively. In a preferred embodiment, the recombinant *E. coli* strains do not comprise a plasmid for co-expression of GroEL and/or GroES and are capable of producing proteins with esterase activity.

In particular, the present invention relates to a recombinant *E. coli* strain suitable for the preparation of a protein with esterase activity according to the method described above, wherein the organism contains a gene coding for a protein with esterase activity wherein the gene has at least 80% identity, preferably at least 85% identity, preferably at least 90% identity, at least 95% identity, preferably 98% identity and most preferably at least 99% identity to the polynucleotide of SEQ ID NO 11, and encodes a protein that has at least 80% identity, preferably at least 85% identity, preferably at least 90% identity, preferably at least 95% identity, preferably at least 98% identity, more preferably at least 99% identity to SEQ ID NO 12.

In particular, the present invention also relates to a recombinant E. coli strain suitable for the preparation of a protein with esterase activity according to the method described above, wherein the organism contains a gene coding for a protein that has at least 80% identity, preferably at least 85% identity, preferably at least 90% identity, preferably at least 95% identity, preferably at least 98% identity, more preferably at least 99% identity to SEQ ID NO. 12.

According to a further embodiment the present invention relates to a recombinant E. coli strain suitable for the preparation of a protein with esterase activity, characterized in that the expression of glutathione reductase and/or thioredoxin reductase is abolished, e.g. by a mutation.

According to a further embodiment of the present invention the expression of both glutathione reductase and thioredoxin reductase of the recombinant E. coli strain is abolished.

Prinz et al (1997) [3] have taught that the activity of a protein containing disulfide bridges (in particular alkaline phosphatase) expressed in E. coli is higher if this protein has been produced in a strain in which the activity of a reductase has been abolished. It was shown also that if both reductases have been abolished spontaneous mutations will take place which enable growth under aerobic conditions. Beckwith et al. (2005) [4] identified a possible spontaneous mutation which restores the ability of the organism to grow under aerobic conditions. They claimed that a mutation in the AhpC gene, comprising an insertion of three nucleotides in the TCT triplet rich region at about codons 36-39 of this gene provides this effect.

Bessette et al. (1999) [5] have analyzed the expression system described by Prinz et al. (1997) in further detail and have shown that the co-expression of the helper protein DsbC (disulfide bond isomerase) enhances the expression of active tissue plasminogen activator and of active alkaline phosphatase. In addition it was disclosed that intracellular expression of a truncated version of DsbC resulted in a functional disulfide bond isomerase protein.

According to a further embodiment of the present invention the recombinant E. coli has been further modified so as to produce a low molecular weight helper protein which is capable to introduce disulfide bonds for a proper folding of proteins requiring disulfide bonds and or is capable to correct misfolding caused by inappropriate disulfide bonds.

Suitable low molecular weight helper proteins referred to above are disulfide isomerases. In a particularly preferred embodiment the helper protein is a protein indicated as DsbC of E. coli (Bessette et al (1999)).

E. coli strains which suitably can be used according to the present invention have the property of a less reductive intracellular environment than wild-type E. coli strains. A particular example of such E. coli strain is the E. coli Origami strain which possesses mutations in the glutathione reductase gene and the thioredoxin reductase gene (Terpe (2006)[6]. When functionally expressed, these genes are counteracting disulfide bond formation in the cytoplasm. Thus heterologous expression of proteins containing disulfide bonds was hitherto considered to require elimination of glutathione and thioredoxin reductase activities, respectively.

However, it was discovered that only one of the mutations is sufficient to have increased functional expression of proteins with PLE activity.

Surprisingly, suitable esterase encoding genes are polynucleotides which encode esterase proteins, and which have codon usage adapted to Pichia.

More in particular, the present invention relates to genes encoding functional esterase protein and which have nucleotide sequence with at least 70% identity, preferably at least 80% identity, preferably at least 85% identity, preferably at least 90% identity, preferably at least 95% identity, preferably at least 98% identity and most preferably at least 99% at least 95% identity compared to the polynucleotide of SEQ ID NO 11, and encodes a protein that has at least 80% identity, preferably at least 85% identity, preferably at least 90% identity, preferably at least 95% identity, preferably at least 98% identity, more preferably at least 99% identity to SEQ ID NO 12.

In an embodiment of the invention, the invention relates to an isolated polynucleotide encoding a functional protein with esterase activity which has a nucleotide sequence of at least 70% identity, preferably at least 80% identity, preferably at least 85% identity, preferably at least 90% identity, preferably at least 95% identity, preferably at least 98% identity and most preferably at least 99% identity to the polynucleotide of SEQ ID NO 11, SEQ ID NO 32, SEQ ID NO 34, SEQ ID NO 36, SEQ ID NO 38, SEQ ID NO 40, SEQ ID NO 42, or SEQ ID NO 44 and encodes a protein that has at least 80% identity, preferably at least 85% identity, preferably at least 90% identity, preferably at least 95% identity, preferably at least 98% identity, more preferably at least 99% identity to SEQ ID NO 12, SEQ ID NO 33, SEQ ID NO 35, SEQ ID NO 37, SEQ ID NO 39, SEQ ID NO 41, SEQ ID NO 43 or SEQ ID NO 45, respectively.

Production of proteins in large amounts can be achieved by expression of the gene encoding the protein of interest in inter alia microbial hosts like bacteria and yeasts, that are amenable to large scale fermentative production. Bacterial protein expression systems have recently been reviewed by Terpe (2006).

According to the present invention such a gene encoding the protein of interest is expressed in a transformed E. coli strain. Transformation of E. coli with the heterologous gene can be accomplished by any suitable method, such as by electroporation, by heat shock transformation, or by chemical transformation.

For transformation of E. coli the gene encoding the protein with esterase activity can be part of a vector, such as a plasmid, a bacteriophage or a phagemid.

The invention also relates to vectors suitable for replication and expression in E. coli containing a polynucleotide encoding a protein with esterase activity which has a nucleotide sequence with at least 70% identity, preferably at least 80% identity, preferably at least 85% identity, preferably at least 90% identity, preferably at least 95% identity, preferably at least 98% identity and most preferably at least 99% identity to the polynucleotide of SEQ ID NO 11, SEQ ID NO 32, SEQ ID NO 34, SEQ ID NO 36, SEQ ID NO 38, SEQ ID NO 40, SEQ ID NO 42, or SEQ ID NO 44 and encodes a protein that has at least 80% identity, preferably at least 85% identity, preferably at least 90% identity, preferably at least 95% identity, preferably at least 98% identity, more preferably at least 99% identity to SEQ ID NO 12, SEQ ID NO 33, SEQ ID NO 35, SEQ ID NO 37, SEQ ID NO 39, SEQ ID NO 41, SEQ ID NO 43 or SEQ ID NO 45, respectively.

The vector should contain the necessary functional elements suitable for e.g. selection, replication, gene regulation transcription (initiation and termination) and the cloning of the desired gene sequence.

The selection of an E. coli strain, a vector, the vector elements, the method of transfection, the culturing of the transfected organisms and the harvesting and isolation of the desired polypeptide suitable for use according to the present invention will be obvious for the man skilled in the art.

Commercial Pig Liver Esterase (PLE) preparations, obtained from animal sources by extraction of pig liver, are widely used in synthetic organic chemistry.

The commercial enzyme preparation has been shown to at least consist of several PLE isozymes possibly with different substrate specificities.

Commercial PLE is used in a variety of biocatalytic reactions exploiting the broad substrate specificity and enantioselectivity of the ester hydrolysis.

E.g. WO 01/09079 describes the use of animal derived PLE for the selective hydrolysis of the (R)-enantiomer of (4E)-5-chloro-2-isopropylpent-4-enoic acid methylester.

As for pharmaceuticals production the interest in using only non animal derived raw materials is increasing due to concerns with respect to transmissible diseases caused by among others viruses and prions, microbial production of esterases using recombinant DNA technology can provide a solution for this issue.

Based on available information (Matsushima et al (1991) [7]., Lange et al. (2001)) on identification and expression of the PLE major (γ-) isozyme, cDNA from pig liver was prepared and screened for PLE γ-isozyme related sequences. For this purpose, PCR primers were designed that recognize cDNA fragments encoding PLE γ-isozyme related proteins. By DNA sequencing of a number of these γ-PLE related cDNA fragments, as expected the known γ-PLE encoding DNA sequence was retrieved, but in addition a second PLE isozyme was identified that differed from the mature γ-PLE protein in 21 out of 548 amino acids. This new PLE isozyme was called APLE for Alternative Pig Liver Esterase.

For functional characterization of both the γ-PLE and APLE isozymes with respect to substrate specificity, both γ-PLE and APLE encoding DNA sequences were inserted in expression cassettes designed for secreted protein production in *Pichia pastoris*, similar as described by Lange et al. In contrast to the latter publication, successful expression of both proteins was accomplished even when the C-terminal amino acid sequence HAEL was present in the encoded protein. Esterase activity was identified by activity determination using a general esterase assay using alpha-naphtylacetate.

Surprisingly, although having a more than 95% identity in amino acid sequence, a distinct difference between γ-PLE and APLE was observed with respect to the hydrolysis of 5-halogen-2-alkylpent-4-enoic acid esters. APLE was able to hydrolyze racemic (4E)-5-chloro-2-isopropylpent-4-enoic acid methylester very efficiently, whereas γ-PLE did not hydrolyze this compound at all. Moreover, it could be shown that the hydrolysis of racemic (4E)-5-chloro-2-isopropylpent-4-enoic acid methylester was by selective hydrolysis of the R-enantiomer only: APLE showed no reactivity towards (2S, 4E)-5-chloro-2-isopropylpent-4-enoic acid methylester. It can be concluded that the known enantioselective hydrolysis of 5-chloro-2-isopropylpent-4-enoic acid methylester by animal derived PLE as described in WO 01/09079 can be attributed to a minor isozyme, APLE, present in the commercial pig liver extract.

For large scale production of a non-animal derived esterase preparation capable of enantioselective hydrolysis of 5-halogen-2-alkylpent-4-enoic acid esters, the *Pichia pastoris* based expression levels of APLE insufficient. Therefore alternative protein production systems were contemplated, taking into account that fast and reliable production at industrial scales will be required for economic production.

PLE isozymes are structurally very related, and it is known that the protein requires intramolecular disulfide bonds for maintaining its structural integrity and activity. Many attractive microbial protein expression systems will only allow disulfide bonds to be formed when the protein is targeted to the extracellular environment, essentially as described above for *Pichia pastoris*. Most bacteria, notably *Escherichia coli*, maintain a reducing environment intracellularly; however, mutants of *E. coli* in which disulfide bonds can be formed in proteins expressed in the cytoplasm have been described (Prinz et al. (1997)), and various strains are available commercially (*E. coli* Origami, Novagen).

Böttcher et al. have made use of such *E. coli* strains, and have shown that γ-PLE can be successfully produced provided that additional measures are taken to ensure proper folding of the γ-PLE protein by overexpression of heat shock proteins; these heat shock proteins, or chaperones, function as folding or refolding helpers to assist proteins to attain their natural conformation. Böttcher et al. (2007) report that no expression of active γ-PLE was observed in the absence of large amounts of the chaperone proteins.

Surprisingly APLE, with only 21 differences out of 548 amino acids when compared to γ-PLE, can be produced as an active esterase enzyme in *E. coli* Origami strains without requiring concomitant overexpression of chaperone proteins; even in the presence of various overexpressed chaperones no effect on APLE activity level is noticed.

More surprisingly, altering the codon usage of the native APLE gene (as isolated from pig liver cDNA) provided an additional boost to APLE expression in *E. coli* Origami strains. Still more surprisingly, particularly altering the codon usage to resemble a set of *Pichia pastoris* genes proved more efficient than performing "codon optimization" towards *E. coli* (for codon tables see:) Hypertext Transfer Protocol Secure://world wide web KAZUSA.OR.JP. This result indicates that there is a direct effect of the DNA and derived messenger RNA sequence on the folding efficiency yielding active APLE protein, rather than optimal codon induced increased translation efficiency and protein production level.

Further improvement of active APLE enzyme production was achieved by overexpressing an *E. coli* endogenous disulfide bond isomerase (DsbC); as already shown by Bessette et al. (1999), truncated versions of DsbC protein can be constructed, that result in intracellular localization of this protein. Combining expression of such truncated DsbC protein results in a considerable increase in APLE activity expressed by the various recombinant *E. coli* hosts.

Functional expression of APLE did not absolutely require a full non-reducing environment in the *E. coli* cell caused by disruption of both trxB and gor genes. Active APLE expression is possible in *E. coli* BL21 Star (full reducing environment !), and in *E. coli* strains in which only one of the genes trxB or gor were inactivated.

The gene structure of the optimal APLE gene, C8P, has been used to construct various esterase isoforms, allowing their high level production in simple and scalable industrial *E. coli* fermentation processes.

Figure 1A:
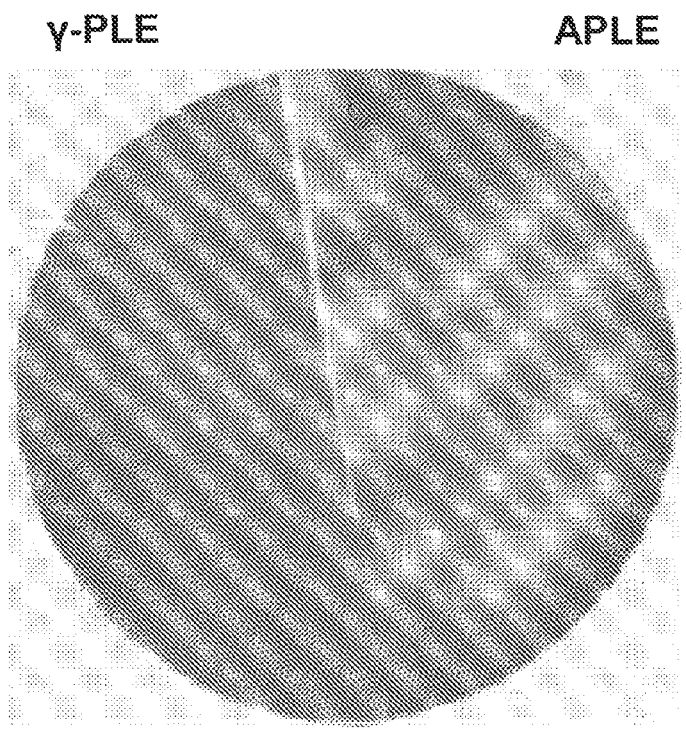
FIG. 1

A. Plate-assay of *P. pastoris* strain X-33 transformed with an APLE or γ-PLE expression cassette using racemic (4E)-5-chloro-2-isopropylpent-4-enoic acid methyl ester as a substrate.

B. Plate-assay of *P. pastoris* strain X33 transformed with an APLE or γ-PLE expression cassette using (2S,4E)-5-chloro-2-isopropylpent-4-enoic acid methyl ester as a substrate.

FIG. 2

A. Functional map of expression plasmid pMS470_C8P;
B. Functional map of expression plasmid pMS470_dsbC_C8P.

FIG. 3

Plate-assay using racemic (4E)-5-chloro-2-isopropylpent-4-enoic acid methyl ester as a substrate and cell-free extract of *E. coli* BL21 Star strains as a source of APLE.

FIG. 4

A: Plate assay using racemic (4E)-5-chloro-2-isopropylpent-4-enoic acid methyl ester as a substrate.
   1. *E. coli* Origami [pMS470_C8E] induced with 0.1 mM IPTG
   2. *E. coli* Origami [pMS470_C8E] induced with 0.5 mM IPTG
   3. *E. coli* Origami [pMS470_C8E] induced with 0.1 mM IPTG in the presence of chaperone encoding plasmid pTf12
   4. *E. coli* Origami [pMS470_C8P] induced with 0.1 mM IPTG
   3. *E. coli* Origami [pMS470_C8P] induced with 0.1 mM IPTG in the presence of chaperone encoding plasmid pTf12

B. Plate assay using racemic (4E)-5-chloro-2-isopropylpent-4-enoic acid methyl ester as a substrate On the left a 2 µl sample of whole cell suspension has been applied to the plate, on the right to each sample 1 µl of 1 M potassium phosphate buffer, pH 8.0 was added to highlight the most efficient hydrolysis. The alphanumerically numbered dots have the following meanings:
   A. *E. coli* Origami non-transformed strain
   B. *E. coli* Origami [pMS470_C8P] stored at 4° C. for 1 month
   C. *E. coli* Origami [pMS470_C8P]
   D. *E. coli* Origami [pMS470_dsbC_C8P]
   E. technical PLE (commercial pig liver esterase, Boehringer)

FIG. 5

A. Coomassie-stained SDS-PAGE.
   1=technical PLE
   2=*E. coli* Origami non-transformed strain
   3=*E. coli* Origami [pMS470_C8P]
   4=*E. coli* Origami [pMS470_dsbC_C8P]
   5=PageRuler prestained protein standard
B. Western blot using polyclonal antibody against PLE.
   1=technical PLE
   2=*E. coli* Origami non-transformed strain
   3=*E. coli* Origami [pMS470_C8P]
   4=*E. coli* Origami [pMS470_dsbC_C8P]

FIG. 6

Qualitative plate assay of various esterase gene constructs using dimethyl methylsuccinate as substrate (both γ-PLE and APLE are reactive towards this substrate).
   1=*E. coli* Origami B [pMS470_dsbC_γ-PLE] (native γ-PLE)
   2=*E. coli* Origami B [p MS470_dsbC_APLE] (native APLE)
   3=*E. coli* Origami B [p MS470_dsbC_APLE-C8A] (APLE C8A gene)
   4=*E. coli* Origami B [p MS470_dsbC_APLE-C8 CpO] (APLE C8 CpO gene)
   5=*E. coli* Origami B [p MS470_dsbC_APLE-C8P] (APLE C8P gene)
   6=*E. coli* Origami B [p MS470_dsbC_APLE-C8E2] (APLE C8E2 gene)
   7=*E. coli* Origami B [p MS470_dsbC_γ-PLE-C8P] (γ-PLE C8A gene)
   8=*E. coli* Origami B [p MS470_dsbC_APLE-C8E] (APLE C8E gene)
   9=*E. coli* Origami B [p MS470_dsbC_BosTaurus] (Bos-Taurus γ-PLE like gene)
   10=Negative control

EXAMPLES

Example 1

Isolation of mRNA and cDNA Synthesis; Identification of Alternative Pig Liver Esterase (APLE)

0.7 g fresh pig liver from a local slaughterhouse was frozen in liquid nitrogen and homogenized using mortar and pestle. mRNA was extracted from the homogenate using the Fast Track® 2.0 mRNA Isolation Kit (Invitrogen, Carlsbad, USA) according to the manufacturer's instructions. The extraction protocol yielded 13 µg mRNA. 0.26 µg mRNA was taken as template for cDNA synthesis using SuperScript™ III First-Strand Synthesis System for RT-PCR (Invitrogen, Carlsbad, USA), according to the manufacturer's instructions.

The cDNA obtained was used as a template in a PCR reaction using specific primers fw-PLE and rv-PLE designed to amplify pig liver esterase/amidase sequences related to the gene described by Matsushima et al. (GenBank Accession No X63323; SEQ ID NO 1).

```
                                            (SEQ ID NO 3)
fw-cPLE: 5'-CAGAATTCATGGCTATCGGGCAGCCAGCCTCGC-3'

(SEQ ID NO 4)
rv-cPLE: 5'-CCGGAATTCAGCCTCCCCTTCACAGCTCAG-3',
``` introducing EcoRI restriction sites (Italics) for cloning purposes. Sequences homologous to known pig liver esterase/amidase sequences are underlined.

Amplification was performed using 1 U Phusion DNA Polymerase (Finnzymes, Espoo, Finland), with 500 ng cDNA as template, 20 µmol of each forward and reverse primer according to the Phusion High-Fidelity DNA Polymerase Manuals (Finnzymes). PCR conditions: 30 s denaturation at 98° C., followed by 30 cycles (10 s 98° C., 20 s 68° C., 1 min 72° C.) for amplification, and a final incubation for 8 min at 72° C. to ensure full-length amplification products.

The resulting 1.7 kbp DNA fragment was cleaned using QIAquick Gel Extraction Kit (QIAGEN, Hilden, Germany), digested using EcoRI restriction endonuclease, inserted into plasmid vectors pHILZ and pHIL-D2 (Invitrogen, Carlsbad, USA), and transformed into electrocompetent *E. coli* TOP10 cells.

DNA sequencing of plasmid DNA from randomly selected transformants revealed two different DNA fragments, one of which was completely identical to the gene described by Matsushima et al., which was later also identified as γ-PLE encoding gene by Böttcher et al.; the second fragment had the nucleotide sequence SEQ ID NO 5 and encoded a protein (APLE; SEQ ID NO 6) that differed from γ-PLE at 21 out of 548 amino acids of the mature protein sequence.

Example 2

Functional Expression of APLE and Characterization of APLE Activity

Both γ-PLE and APLE genes were adapted for secretory expression in *Pichia pastoris* by fusion with the α-mating factor secretion signal sequence as present in vector pPICZα (Invitrogen, Carlsbad, USA).

The α-mating factor secretion signal sequence and the γ-PLE and APLE genes were first amplified separately:
PCR 1: α-mating factor secretion signal sequence using the primers:

```
fw-alpha:
                                          (SEQ ID NO 7)
5'-TCTTCGAAGAATTCACGATGAGATTTCCTTCAATTTTTACTGC-3' rv-alpha:
                                          (SEQ ID NO 8)
5'-GAGGCTGGCTGCCCAGCTTCAGCCTCTCTTTTCTCG-3'
```

PCR 2 (γ-PLE) and PCR 3 (APLE) using the primers:

```
fw-PLE:
                                          (SEQ ID NO 9)
5'-AGAGAGGCTGAAGCTGGGCAGCCAGCCTCGCCG-3' rv-PLE:
                                         (SEQ ID NO 10)
5'-ATGGTACCGAATTCTCACTTTATCTTGGGTGGCTTCTTTG-3'
```

EcoRI restriction sites for cloning purposes are italicized, whereas sequences homologous to templates are underlined.

PCR conditions for all reactions: 50 µl reaction mix with 2 ng template DNA, 0.5 µM of each primer, 0.2 mM dNTPs, 1× Phusion HF buffer and 1 U of Phusion DNA-Polymerase, according to Phusion High-Fidelity DNA Polymerase Manual (Finnzymes), 3 min denaturation at 85° C., amplification in 30 cycles (30 s 95° C., 30 s 57° C., 15 s 72° C.), and a final incubation of 7 min at 72° C.

Template for the α-mating factor secretion signal amplification (PCR1) was plasmid pPICZα; template for the γ-PLE and APLE gene amplification (PCR2 and PCR3, respectively) were the cDNA's in pHILZ vectors described in example 1.

Subsequently, the separate fragments obtained were combined in fusion reactions between the α-mating factor fragment and each of the pig liver esterase genes, as follows: α-mating factor fragment (PCR1)+γ-PLE fragment (PCR2); α-mating factor fragment (PCR1)+APLE fragment (PCR3).

Reactions were started in a total volume of 45 µl with 3 µl each from PCR1 and PCR2 or PCR3, respectively, 0.2 mM dNTPs, 1× Phusion HF buffer, and 1 U of Phusion DNA-Polymerase, 3 min at 95° C. followed by 10 cycles of 30 s at 95° C. and 45 s at 72° C. Subsequently, primers fw-alpha and rv-PLE were added to 0.5 µM final concentration and full-length product amplification was achieved by 3 min denaturation at 95° C., amplification in 30 cycles (30 s 95° C., 30 s 57° C., 15 s 72° C.), and a final incubation of 7 min at 72° C.

The resulting fragments were purified using the QIAquick PCR Purification Kit (QIAGEN, Hilden, Germany), and after digestion with EcoRI inserted into vector pGAPZ A (Invitrogen, Carlsbad, USA), resulting in plasmids pGAPZA_γ-PLE and pGAPZA_APLE.

DNA of plasmids pGAPZA_γ-PLE and pGAPZA_APLE was linearized and introduced into *Pichia pastoris* X-33 according to the *Pichia* Expression Kit manual (Invitrogen, Carlsbad, USA). Transformants were selected on YPD-agar containing 100 mg/l Zeocin.

*Pichia pastoris* transformants carrying pGAPZA_γ-PLE and pGAPZA_APLE were streaked onto YPD agar supplemented with 100 mg/l Zeocin and grown for 48 h at 30° C. Cell material was then lifted onto Whatman 541 hardened ashless 70 mmØ filters (Whatman International Ltd., Maidstone, Great Britain) and dried. Then, filters were soaked in a mixture of 6 mg α-naphthylacetate (Sigma, dissolved in 500 µl acetone), 2.5 mg Fast Blue Salt BN (Sigma, dissolved in 125 µl water) and 5 ml 0.1 M potassium phosphate buffer, pH 7.0, incubated to visualize esterase activity by hydrolysis of α-naphthylacetate resulting in a colored product. All *Pichia pastoris* strains transformed with γ-PLE and APLE expression cassettes showed increased esterase activity when compared to the non-transformed *Pichia pastoris* X-33 parent strain.

A similar set-up as described for the general esterase assay was developed to determine activity of γ-PLE and APLE towards 5-halogen-2-alkylpent-4-enoic acid esters. The filters were now soaked in assay mixture consisting of 14 mM potassium phosphate buffer, pH 8.0, 10% (v/v) racemic (4E)-5-chloro-2-isopropylpent-4-enoic acid methyl ester (DSM Fine Chemicals Austria Nfg GmbH & Co KG, Linz, Austria), 1% (v/v) Emulgen 913 detergent (Kao Corporation, Tokyo, Japan), 2 mg/ml phenol red. Enzyme activity is indicated by a color change from red (basic and neutral pH) to yellow (acidic pH), caused by the hydrolysis of (4E)-5-chloro-2-isopropylpent-4-enoic acid methyl ester and the associated liberation of acidic groups.

Figure 1B:
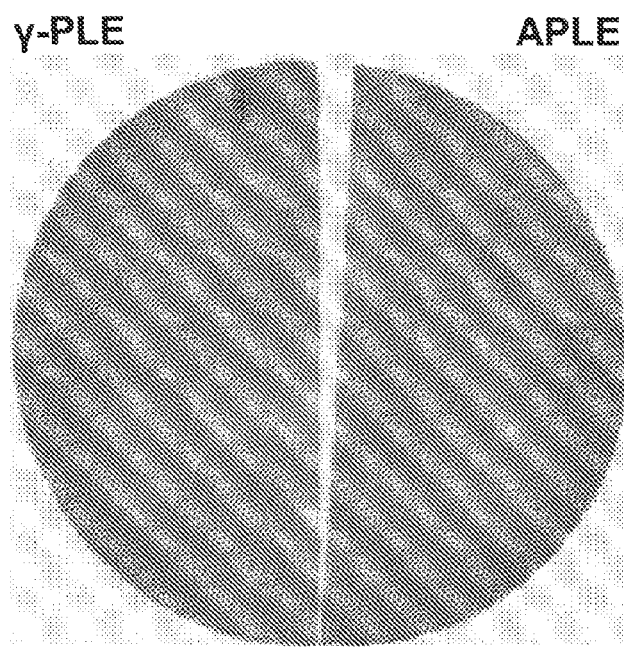

As shown in FIG. 1A, only APLE gives a positive signal indicating that this enzyme is capable of hydrolysis of racemic (4E)-5-chloro-2-isopropylpent-4-enoic acid methyl ester; γ-PLE does not hydrolyze this substrate to a detectable extent. More importantly, it can be concluded that the APLE enzyme selectively hydrolyzes (2R,4E)-5-chloro-2-isopropylpent-4-enoic acid methyl ester: in a plate assay in which only the S-enantiomer of the substrate was applied to the filter no hydrolysis of the S-form can be detected (FIG. 1B).

Example 3

Design of Synthetic APLE Genes

Based on the amino acid sequence of mature APLE (SEQ ID NO 6) derived from the APLE encoding gene (SEQ ID NO 5), synthetic genes with altered codon usage and lacking the native secretion signal sequence were designed and chemically synthesized (supplier: DNA2.0, Menlo Park, USA). Synthetic APLE gene variants C8P (SEQ ID NO 11), C8A (SEQ ID NO 13), C8 CpO (SEQ ID NO 14), and C8E (SEQ ID NO 15) all encode mature APLE protein with an additional N-terminal Methionine as a required translation startcodon (SEQ ID NO 12).

For expression studies in *E. coli*, synthetic APLE genes were inserted into plasmid pMS470 (Balzer et al. (1992) [8]). PCR amplification (for conditions see Example 1) was used to add an NdeI restriction site (including an ATG startcodon) to the 5' end and a HindIII restriction site to the 3' end, respectively, using the following primers:

For gene APLE C8P the following PCR primers were designed

```
Fw-C8P (SEQ ID NO 16):
CTTTAAGAAGGAGATATACATATGGGACAACCAGCTTCGCCGCC

Rv-C8P (SEQ ID NO 17):
CCCCCCCCCCCCAAGCTTATTACAATTCGGCGTGCTTTATCTTAGG
```

For gene APLE C8A the following PCR primers were designed

```
Fw-C8A (SEQ ID NO 18):
ATTTATACATATGGGACAACCAGCTTCGCCGCCTGTCG
```

```
-continued
Rv-C8A (SEQ ID NO 19):
CCGCCAAGCTTATTACAATTCAGCGTGCTTAATCTTTGGAGGC
```

For gene APLE C8 CpO the following PCR primers were designed

```
Fw-C8CpO (SEQ ID NO 20):
ATTTATACATATGGGCCAACCTGCTTCTCCACCTGTTG

Rv-C8CpO (SEQ ID NO 21):
CCGCCAAGCTTATTACAATTCAGCATGCTTGATCTTTGGTGGC
```

For gene APLE C8E the following PCR primers were designed

```
Fw-C8E (SEQ ID NO 22):
ATTTATACATATGGGACAACCAGCTTCGCCGCCTGTCG

Rv-C8E (SEQ ID NO 23):
CCGCCAAGCTTATTACAATTCGGCGTGCTTTATCTTAGGTGGC
```

NdeI and HindIII restriction sites for cloning purposes are in italics, sequences homologous to the gene templates are underlined.

Figure 2A:
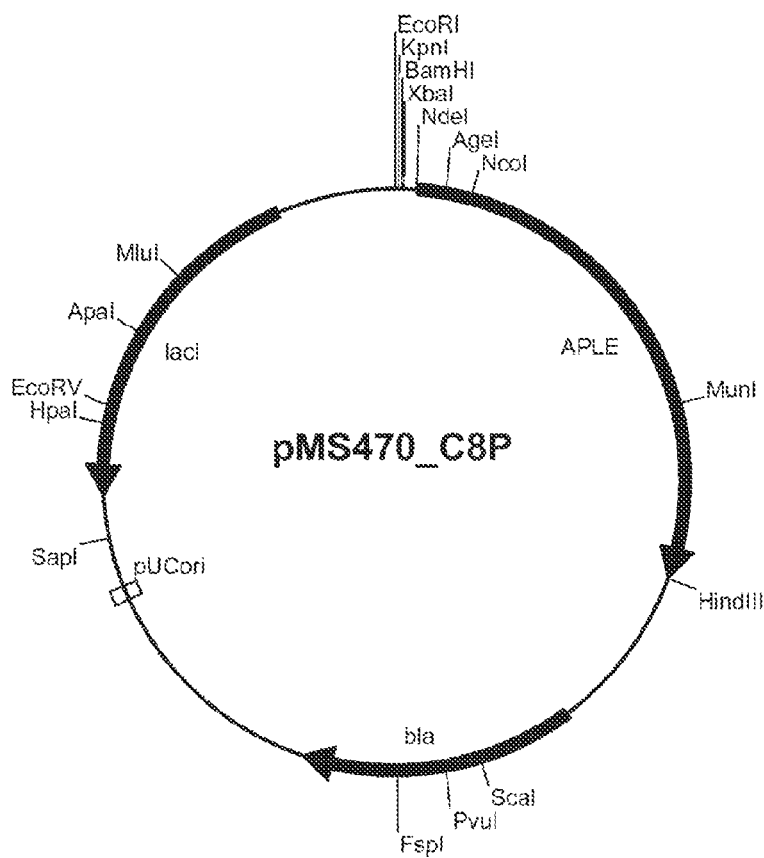

The resulting fragments were inserted into NdeI/HindIII digested pMS470 creating the plasmids pMS470_C8P, pMS470_C8A, pMS470_C8 CpO, and pMS470_C8E. A map of plasmid pMS470_C8P is depicted in FIG. 2A.

Natural sequences of APLE and γ-PLE were obtained as cDNA from pig liver as described in example 1. These natural genes were amplified and transferred to E. coli expression vectors using the following primers:

```
Fw-PLEnat
                                  (SEQ ID NO 24)
ATTTATACATATGGGGCAGCCAGCCTCGCCGCCTG Rv-PLEnat
                                  (SEQ ID NO 25)
CCGCCAAGCTTATCACAGCTCAGCATGCTTTATCTTGGGTGG
```

NdeI and HindIII restriction sites for cloning purposes are in italics, sequences homologous to templates are underlined.

Because these natural genes have an internal HindIII restriction site, a two-step ligation was necessary: first the longer fragment with NdeI and HindIII was inserted into pMS470, subsequently each gene was completed by adding the 3' HindIII fragment, resulting in the final expression vectors pMS470_γ-PLE and pMS470_APLE, respectively.

Example 4

Transformation of APLE Expression Vectors to Suitable E. coli Host: Functional Expression of APLE in E. coli For analyzing esterase expression in E. coli, the following procedures were used for cultivation and preparation of cells for activity analysis.

For plate assays, E. coli strains harboring various expression plasmids were streaked onto LB-agar plates containing 100 μg/ml I ampicillin and 0.1 mM IPTG, and incubated for 16 h at 37° C.

For liquid culture assays, E. coli strains carrying the respective expression plasmid was inoculated in 5 ml of Luria-Bertani (LB) broth with 100 μg/ml ampicillin and incubated at 28° C. under continuous shaking for 16 hrs. This culture was then used to inoculate 250 ml LB broth with 100 μg/ml ampicillin, in 1 L baffled shake flasks. When the culture reached an optical density of 0.6 to 0.8 at 600 nm, IPTG was added to a final concentration of 0.1 mM to induce gene expression. Cells were harvested after 16 to 20 h incubation at 28° C.

Plate assays: Assay on cells grown on agar plates have been described in Example 2 with various esterase substrates.

Activity analysis on liquid E. coli cultures: Esterase activity was quantitatively determined on cell suspensions in MOPS buffer (100 mM) with 5 mM p-nitrophenyl acetate as substrate. The amount of p-nitrophenol released was determined spectrophotometrically at 405 nm. One unit (U) of esterase activity is defined as the amount of enzyme that liberates 1 micromole p-nitrophenol per minute under the conditions of the test (pH 7.5, 37° C.).

The expression cassettes for the different APLE encoding genes were transformed to various E. coli strains: both regular gene expression strains like E. coli BL21 strains, and specifically engineered E. coli strains that allow functional intracellular expression of proteins requiring intramolecular disulfide bonds for correct folding and enzymatic activity (Prinz et al., Bessette et al.) were used as expression host strains. For this purpose, commercially available E. coli strains of the Origami family (Novagen) were used, notably Origami 1, Origami 2, and Origami B.

Figure 3:
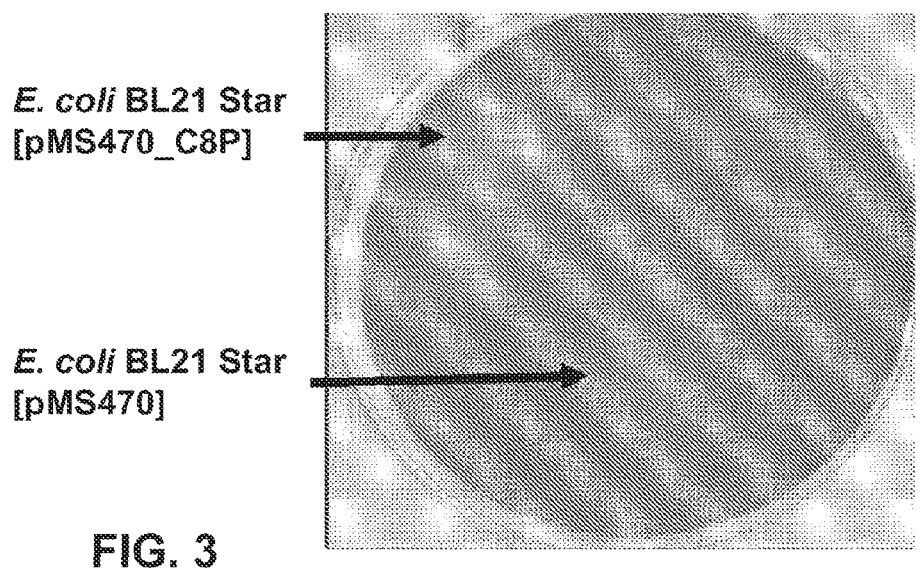

Functional expression of APLE (SEQ ID NO 12) was observed in standard expression strain E. coli BL21 Star (FIG. 3), however activity was far below activities obtained by the use of E. coli Origami strains.

E. coli Origami strains were transformed with the respective expression vectors, and selected transformants were subsequently evaluated for esterase expression either by plating on substrate specific assay plates or via shake flask cultures.

Figure 4:
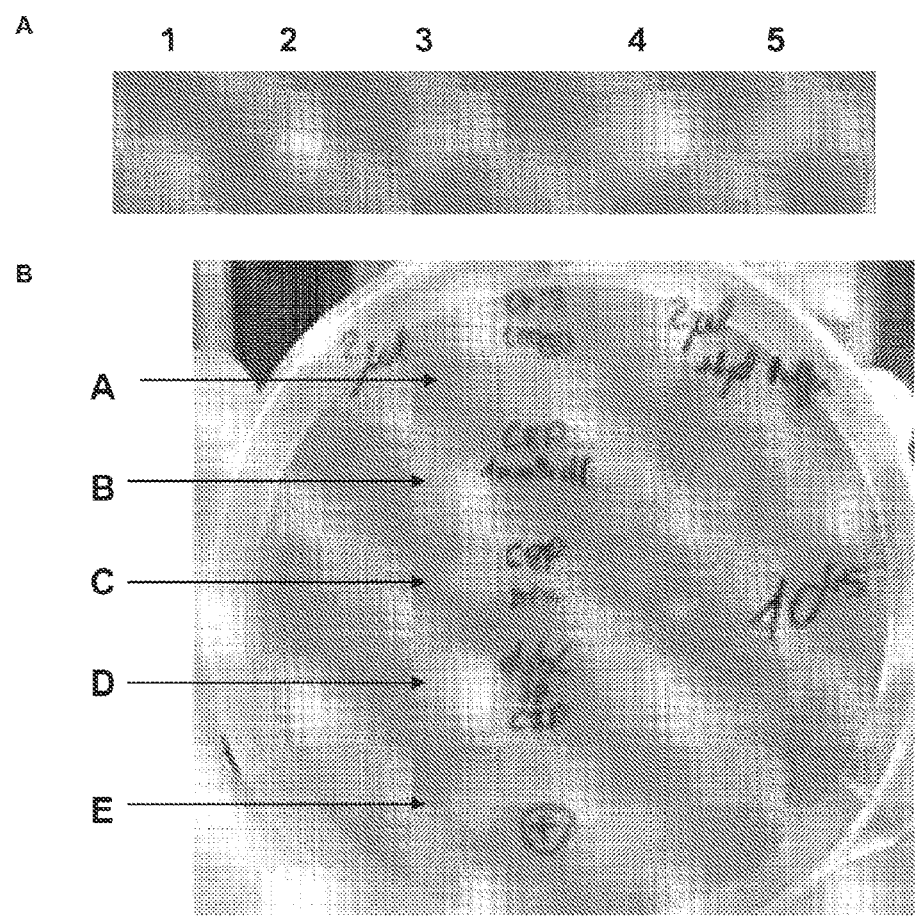

The expression levels of several APLE gene variants are summarized in FIG. 4A and Table 1; gene C8E has only minor changes as compared to natural APLE gene. FIG. 4A shows the expression difference of C8E and C8P as such and in the presence of chaperone pTf16; the plate results are confirmed by the shake flask results presented in Table 1.

TABLE 1

| E. coli host strain | APLE expression plasmids | Esterase activity (u/ml) |
|---|---|---|
| Origami 1/2/B | — | 0.8 |
| Origami 1 | pMS470_C8E | 1.2 |
| Origami 1 | pMS470_C8P | 9.1 |
| Origami 2 | pMS470_C8P | 9.6 |
| Origami B | pMS470_C8P | 10.7 |

A series of experiments was executed to assess whether co-expression of various heat shock chaperones contributed to APLE expression. The results (summarized in table 2) show that heat shock protein/chaperone expression does not significantly affect APLE production.

TABLE 2

| E. coli host | APLE expression plasmids | Heat shock protein expression plasmid | |
|---|---|---|---|
| Origami 1 | — | | 0.8 |
| Origami 1 | pMS470_C8P | | 9.2 |
| Origami 1 | pMS470_C8P | pG-KJE8 | 8.1 |
| Origami 1 | pMS470_C8P | pGro7 | 9.3 |
| Origami 1 | pMS470_C8P | pKJE7 | 10.1 |
| Origami 1 | pMS470_C8P | pG-Tf2 | 9.2 |
| Origami 1 | pMS470_C8P | pTf16 | 8.8 |

Example 5

Increase in APLE Expression Through Addition of DsbC

With no effect observed of co-expressed heat shock proteins, it was investigated whether other cofactors like overexpression of the *E. coli* endogenous disulfide-isomerase gene dsbC (Bessette et al.) would affect expression of APLE in *E. coli*.

*E. coli* Top10F' chromosomal DNA was used as a template to amplify a truncated version of the *E. coli* dsbC gene (native DsbC protein is secreted to the periplasm, the truncated DsbC protein remains in the intracellular compartment) by polymerase chain reaction (PCR) with Phusion™ High-Fidelity DNA Polymerase (Finnzymes, Espoo, Finland), using Phusion HF-Buffer and the following conditions: 5 minutes denaturation at 95° C., amplification in 30 cycles (10 s 98° C., 30 s 66° C., 30 s 72° C.), and a final incubation of 8 min at 72° C. Primers used were designed to include a Shine-Dalgarno sequence in front of truncated DsbC coding sequence:

```
Fw-dsbC (SEQ ID NO 26):
5'-CGGATCCTTTAACTTTAAGAAGGAGATATAATGGATGACGCGGCAAT

TCAACAAACG-3'

Rv-dsbC (SEQ ID NO 27):
5'-CGGATCCTTATTTACCGCTGGTCATTTTTTGGTGTTCG-3'
```

Figure 2B:
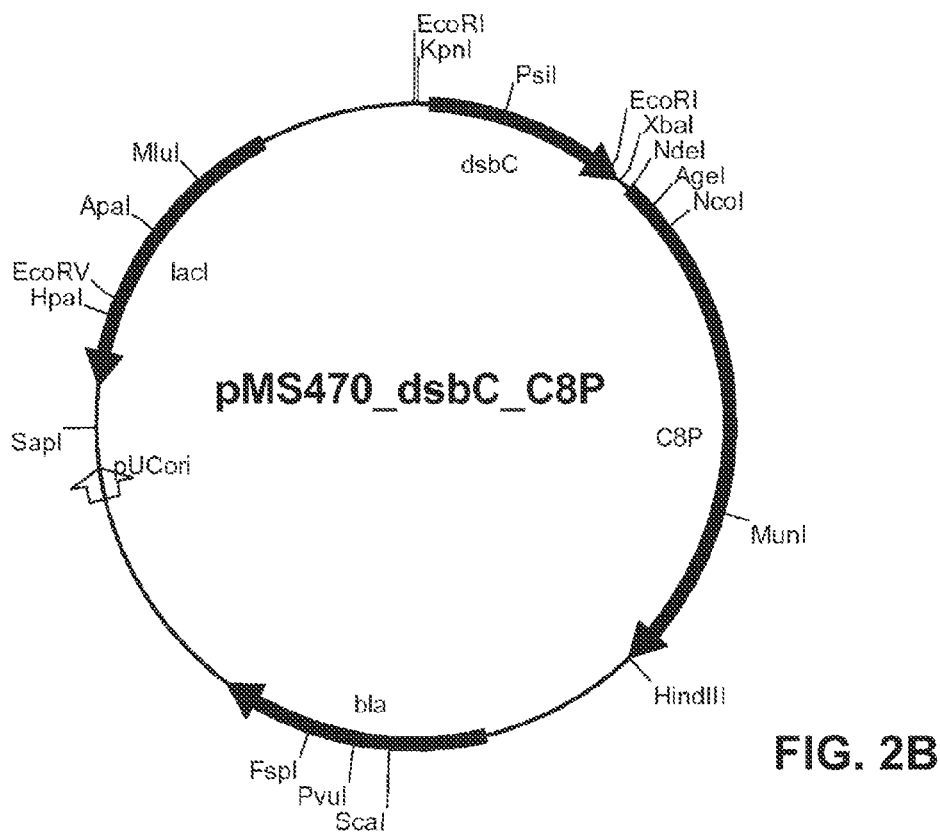

The PCR product was digested with BamHI and inserted in the BamHI restriction site of the APLE expression plasmid pMS470_C8P. DsbC and C8P are separated by 49 bp. The constructs were verified by sequencing. The construct was named pMS470_dsbC_C8P and improved expression of APLE drastically (see FIG. 4 for plate assays, and Table 3). A functional map of plasmid pMS470_dsbC_C8P is depicted in FIG. 2B.

TABLE 3

| *E. coli* host strain | Plasmids | Esterase activity (u/ml) |
|---|---|---|
| Origami B | — | 0.8 |
| Origami 1 | — | 0.8 |
| Origami 1 | pMS470_C8P | 9.0 |
| Origami 1 | pMS470_dsbC_C8P | 47 |
| Origami B | pMS470_C8P | 10.5 |
| Origami B | pMS470_dsbC_C8P | 59 |

To confirm that the observed esterase activity was indeed due to functional expression of the APLE encoding gene Western blotting experiments were performed. After fermentation, *E. coli* cells were centrifuged at 5.000 g for 10 min. The resulting pellet was resuspended in 4 volumes of 20 mM potassium phosphate buffer, pH 8.0, and 2-2.5 µl of the cell suspension were combined with 17.5-18 µl SDS loading buffer, heated at 95° C. for 10-15 min and loaded onto a 12.5% SDS-PAGE gel. APLE was detected by Western blot analysis using a rabbit polyclonal antibody against porcine liver esterase (abcam, Cambridge, UK) as primary antibody and goat-anti-rabbit polyclonal antibody conjugated with alkaline phosphatase (Leinco Technologies Inc., St. Louis, USA) as secondary antibody. Western blot detection was done by Lumi-Phos™ WB Chemiluminescent Substrate (AP) (Pierce, Rockford, USA) and chemiluminescence detection in a G:Box HR (Syngene, Cambridge, UK) or by BCIP/NBT detection solution (CALBIOCHEM; La Jolla; USA) and direct staining of the nitrocellulose membrane (Hybond-ECL™, Amersham Biosciences, Uppsala, Sweden).

Figure 5A:
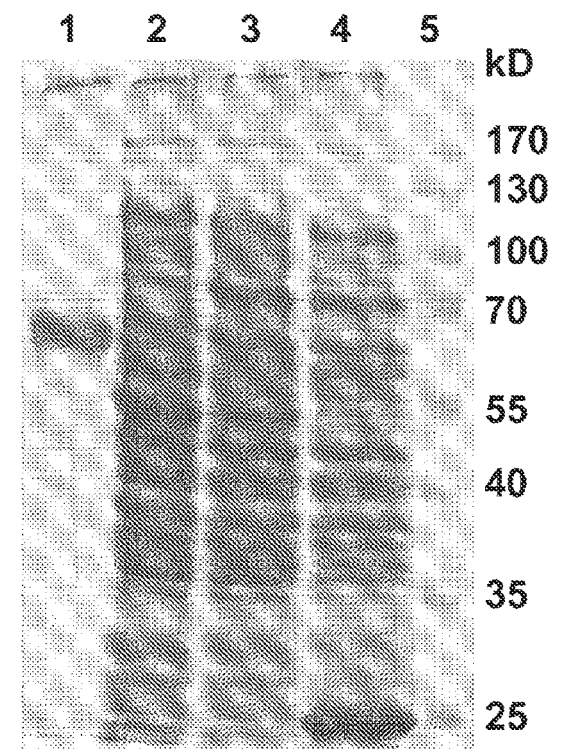
Figure 5B:
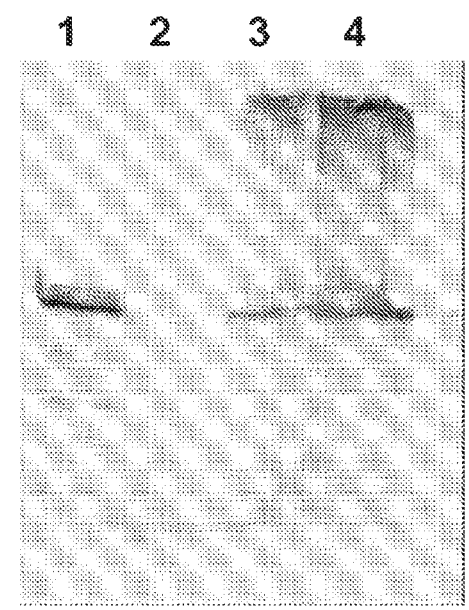

FIG. 5 shows the Coomassie stained SDS-PAGE gel (FIG. 5A) and the results of the Western blotting experiment (FIG. 5B), indicating that the protein expression level parallels the activity difference. FIG. 5A also shows that truncated DsbC is very well expressed.

Example 6

Preparation of New *E. coli* Host Strains and Analysis of the APLE Production Properties of these Hosts

*Escherichia coli* K12 strain RV308 ΔtrxB; Δgor was constructed starting from *E. coli* strain RV308 (ATCC 31608). Similarly as described by Prinz et al., two genes involved in intracellular disulfide reduction were inactivated. These two genes, trxB and gor encoding thioredoxin reductase and glutathione oxidoreductase, respectively, were inactivated through deletion using site directed recombination technology according to the procedures described by Datsenko et al. (2000) [9].

The initial result of this modification is that the *E. coli* strain is no longer capable of growing aerobically, except in the presence of a reducing agent; however, suppressor mutations restoring aerobic growth in the absence of a reductant are easily selected. These properties and phenotypic change have been described previously in *E. coli* strains in which the genes trxB and gor were inactivated using a different approach.

In detail: deletion cassettes were obtained by PCR using the following primers and plasmid pKD3 as a template:
Application in this reaction of fw-trxB (SEQ ID NO 28): 5'-GTAAATTCCCTACAATCCTGCCCAT-TGTCTGCCAACAACTATGGGGATCTTGTGTA GGCTGGAGCTGCTTC-3' and rv-trxB (SEQ ID NO 29): 5'-CCCATAGTCGCATGGTGTCGCCTTCTT-TACTTTTGTTACTGATTTGTAAAACATATG AATATC-CTCCTTAG-3' results in a deletion cassette for the gene trxB
Application in this reaction of fw-gor (SEQ ID NO 30): 5'-CCTATTACGTCTCGCGCTACAATCGCGG-TAATCAACGATAAGGACACTTTGTCTGT GTAG-GCTGGAGCTGCTTC-3' and rv-gor (SEQ ID NO): 5'-CT-GATAGCGGAAACGTAATTAAGGGCTAAGAGCACAC-TACTCTTAGCCCTTTAACC ATATGAATATCCTCCT-TAG-3' results in a deletion cassette for the gene gor.

The trxB and gor deletion cassettes were transformed separately to an *E. coli* RV308 strain that already contains plasmid pKD46, and successful transformants were selected based on their acquired resistance towards the antibiotic chloramphenicol. Correct exchange of the trxB gene or the gor gene by the respective deletion cassettes was confirmed by PCR controls and Southern blotting. The chloramphenicol resistance gene was subsequently removed by transformation with plasmid pCP20, encoding a FLP recombinase enzyme [reference 6]. The resulting *E. coli* strain RV308 ΔtrxB was checked again for a clean deletion of trxB using PCR and Southern blotting. Similarly the clean deletion of the gor gene in *E. coli* strain RV308 confirmed.

Starting from strain *E. coli* strain RV308 ΔtrxB exactly the same set of reactions was carried out to perform a clean deletion of the gene gor. Because the initial result of this second modification, as described by Prinz et al. is that this *E. coli* RV308 strain having both trxB and gor deleted is no longer capable of growing aerobically except in the presence of a reducing agent, growth of *E. coli* strains that were assumed to also have the gor deletion was conducted in the presence of the reducing agent DTT. Finally, spontaneous RV308 ΔtrxB; Δgor mutants could be selected that for aerobic growth were no longer dependent on the presence DTT.

Transformation of *E. coli* strain RV308 ΔtrxB; Δgor and intermediate strains with only a single reductase deletion were transformed with selected APLE expression plasmids and evaluated in shake flask for APLE production (Table 4).

TABLE 4

| E. coli host | Plasmid | |
|---|---|---|
| Origami B | — | 0.7 |
| RV308 ΔtrxB; Δgor | | 0.6 |
| Origami B | pMS470_C8P | 11.5 |
| RV308 ΔtrxB | pMS470_C8P | 2.2 |
| RV308 Δgor | pMS470_C8P | 2.8 |
| RV308 ΔtrxB; Δgor | pMS470_C8P | 8.0 |
| Origami B | pMS470_dsbC_C8P | 56 |
| RV308 ΔtrxB | pMS470_dsbC_C8P | 1.5 |
| RV308 Δgor | pMS470_dsbC_C8P | 10.2 |
| RV308 ΔtrxB; Δgor | pMS470_dsbC_C8P | 42 |

Example 7

Additional synthetic genes were chemically synthesized that encoded various natural isoforms of pig liver esterase protein. For production of a new esterase protein, a *Bos taurus* γ-PLE like gene was synthesized.

Other new genes encoded known the PLE esterases γ-PLE and PICE; also hybrids between the APLE and γ-PLE isoforms were designed. The common feature of the latter set was that all are based on the APLE C8P template. Starting from APLE C8P, only the codons required to obtain the isoforms or hybrid proteins were changed.

The genes with their encoded proteins are represented by:
Natural isoforms: New hypothetical *Bos taurus* γ-PLE like gene (SEQ ID NO 32)

C8P encoded natural esterases: C8P-γ-PLE (SEQ ID NO 34) and C8P-PICE (SEQ ID NO 36).

C8P encoded hybrid esterases: C8P-H1 (SEQ ID NO 38), C8P-H2 (SEQ ID NO 40), C8P-H3 (SEQ ID NO 42), and C8P-H4 (SEQ ID NO 44).

All sequences were inserted in the *E. coli* expression vector of FIG. 2B (pMS470_dsbC_APLE) effectively replacing the C8P gene.

Figure 6:
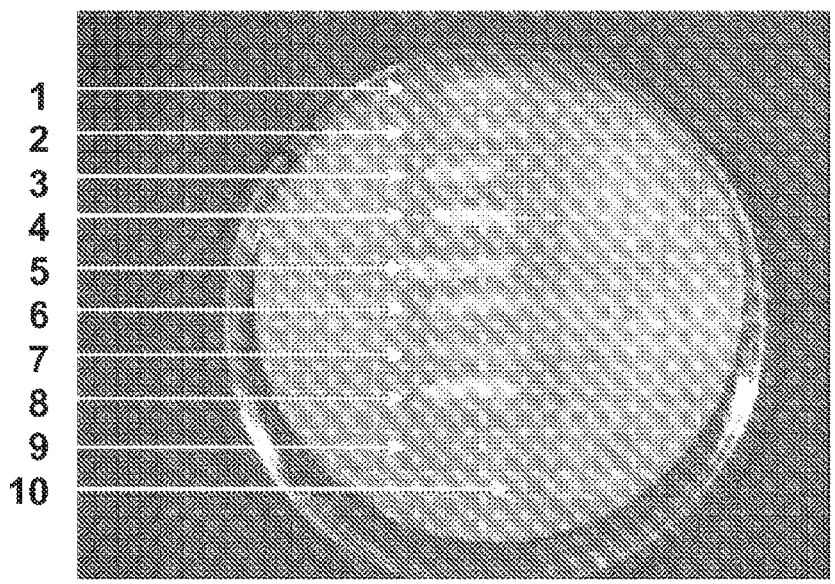

The results of the qualitative plate assay (see example 2) using dimethyl methylsuccinate as a substrate confirm that each of the designed genes encodes an active esterase (FIG. 6). This plate assay however does not allow quantitative conclusions because the specific activity of enzyme variants towards the dimethyl methylsuccinate is not known.

REFERENCES

[1] Lange S., Musidlowska A., Schmidt-Dannert C., Schmitt J., Bornscheuer U. T. (2001) *Chem BioChem* 2, 576-582
[2] Böttcher, D., Brüsehaber, E., Doderer, K. and Bornscheuer, U. T. (2007) *Appl. Microbiol. Biotechnol.* 73, 1282-1289
[3] Prinz, W. A., Åslund, F., Holmgren, A. and Beckwith, J. (1997) *J. Biol. Chem.* 272: 15661-15667
[4] Beckwith, J., Åslund, F., Bessette, P. H., Georgiou, G., Ritz, D. and Lim, J. E. U.S. Pat. No. 6,872,563
[5] Bessette, P. H., Åslund, F., Beckwith, J. And Georgiou, G. (1999) *PNAS* 96 (24), 13703-13708
[6] Terpe, K. (2006) *Appl. Microbiol. Biotechnol.* 72, 211-222.
[7] Matsushima M, Inoue H, Ichinose M, Tsukada S, Miki K, Kurokawa K, Takahashi T, Takahashi K. (1991). *FEBS Lett.* 293, 37-41
[8] Balzer D, Ziegelin G, Pansegrau W, Kruft V, Lanka E. (1992). *Nucleic Acids Res.* 20, 1851-1858
[9] Datsenko, K. A. & Wanner, B. L. (2000) *PNAS* 97, 6640-6645

The invention claimed is:

1. A method of producing a protein with esterase activity comprising expressing a gene encoding the protein in an *E. coli* strain, wherein the gene encoding the protein with esterase activity has at least 99% identity to the polynucleotide of SEQ ID NO 11 and encodes a protein that has at least 99% identity to SEQ ID NO 12 and wherein the expression takes place without coexpression of GroEL and/or GroES from a plasmid.

2. The method according to claim 1, wherein the expression takes place without coexpression of an additional heat shock chaperone protein.

3. The method according to claim 1, wherein the expression takes place with overexpression of endogenous dsbC gene.

4. The method according to claim 1, wherein the *E. coli* strain comprises Origami 1, Origami 2 or Origami B cells.

5. The method according to claim 4, wherein the expression takes place without coexpression of an additional heat shock chaperone protein.

6. The method according to claim 4, wherein the expression takes place with overexpression of endogenous dsbC gene.

7. The method according to claim 1, wherein the expression takes place in a recombinant *E. coli* strain that is unable to express glutathione reductase and/or thioredoxin reductase.

8. The method according to claim 7, wherein the expression takes place without coexpression of an additional heat shock chaperone protein.

9. The method according to claim 7, wherein the expression takes place with overexpression of endogenous dsbC gene.

10. A method of producing a protein with esterase activity comprising expressing a gene encoding the protein in an *E. coli* strain, wherein the gene encoding the protein with esterase activity has at least 99% identity to the polynucleotide of SEQ ID NO 11 and encodes a protein that has at least 99% identity to SEQ ID NO 12.

11. The method according to claim 10, wherein the expression takes place without coexpression of an additional heat shock chaperone protein.

12. The method according to claim 10, wherein the expression takes place with overexpression of endogenous dsbC gene.

13. The method according to claim 10, wherein the *E. coli* strain comprises Origami 1, Origami 2 or Origami B cells.

14. The method according to claim 13, wherein the expression takes place without coexpression of an additional heat shock chaperone protein.

15. The method according to claim 13, wherein the expression takes place with overexpression of endogenous dsbC gene.

16. The method according to claim 10, wherein the expression takes place in a recombinant *E. coli* strain that is unable to express glutathione reductase and/or thioredoxin reductase.

17. The method according to claim 16, wherein the expression takes place without coexpression of an additional heat shock chaperone protein.

18. The method according to claim 16, wherein the expression takes place with overexpression of endogenous dsbC gene.

* * * * *

SEQUENCE LISTING

```
<160> NUMBER OF SEQ ID NOS: 45

<210> SEQ ID NO 1
<211> LENGTH: 1701
<212> TYPE: DNA
<213> ORGANISM: Sus scrofa
<220> FEATURE:
<221> NAME/KEY: CDS
<222> LOCATION: (1)..(1701)
<223> OTHER INFORMATION: Pig Liver Esterase

<400> SEQUENCE: 1 atg tgg ctt ctc ccg ctg gtc ctg acc tcc ctc gcc tct tct gca act      48
Met Trp Leu Leu Pro Leu Val Leu Thr Ser Leu Ala Ser Ser Ala Thr
1               5                   10                  15 tgg gca ggg cag cca gcc tcg ccg cct gtt gtg gac act gcc cag ggc      96
Trp Ala Gly Gln Pro Ala Ser Pro Pro Val Val Asp Thr Ala Gln Gly
            20                  25                  30 cga gtc ctg ggg aag tac gtc agc tta gaa ggc ctg gca cag ccg gtg     144
Arg Val Leu Gly Lys Tyr Val Ser Leu Glu Gly Leu Ala Gln Pro Val
        35                  40                  45 gcc gtc ttc ctg gga gtc cct ttt gcc aag ccc cct ctc gga tcc ttg     192
Ala Val Phe Leu Gly Val Pro Phe Ala Lys Pro Pro Leu Gly Ser Leu
    50                  55                  60 agg ttt gct ccg ccg cag cct gca gaa cca tgg agc ttc gtg aag aac     240
```

-continued

| | | |
|---|---|---|
| Arg Phe Ala Pro Pro Gln Pro Ala Glu Pro Trp Ser Phe Val Lys Asn<br>65                              70                        75                          80 | |
| acc acc tcc tac cct ccc atg tgc tgc cag gac cca gta gtg gag cag<br>Thr Thr Ser Tyr Pro Pro Met Cys Cys Gln Asp Pro Val Val Glu Gln<br>                              85                          90                        95 | 288 |
| atg acc tca gat cta ttt acc aac gga aag gag agg ctc act ctg gag<br>Met Thr Ser Asp Leu Phe Thr Asn Gly Lys Glu Arg Leu Thr Leu Glu<br>                        100                       105                      110 | 336 |
| ttt tct gaa gac tgt ctc tac cta aat att tac acc cct gct gac ctg<br>Phe Ser Glu Asp Cys Leu Tyr Leu Asn Ile Tyr Thr Pro Ala Asp Leu<br>            115                      120                      125 | 384 |
| aca aag agg ggc aga ctg ccg gtg atg gtg tgg atc cac gga gga ggc<br>Thr Lys Arg Gly Arg Leu Pro Val Met Val Trp Ile His Gly Gly Gly<br>        130                      135                      140 | 432 |
| ctg gtg ttg ggc ggg gca cca atg tat gat ggg gtg gtg ctt gct gcg<br>Leu Val Leu Gly Gly Ala Pro Met Tyr Asp Gly Val Val Leu Ala Ala<br>145                              150                        155                      160 | 480 |
| cat gaa aac gtg gtg gtg gtg gcc atc cag tac cgc ctg ggc atc tgg<br>His Glu Asn Val Val Val Val Ala Ile Gln Tyr Arg Leu Gly Ile Trp<br>                        165                       170                      175 | 528 |
| gga ttc ttc agc aca ggg gat gaa cac agc cgg ggc aac tgg ggt cac<br>Gly Phe Phe Ser Thr Gly Asp Glu His Ser Arg Gly Asn Trp Gly His<br>                  180                       185                      190 | 576 |
| ttg gac cag gtg gcc gca ctg cac tgg gtc cag gag aac atc gcc aac<br>Leu Asp Gln Val Ala Ala Leu His Trp Val Gln Glu Asn Ile Ala Asn<br>                195                       200                      205 | 624 |
| ttt gga ggc gac cca ggc tct gtg acc atc ttt gga gag tca gca gga<br>Phe Gly Gly Asp Pro Gly Ser Val Thr Ile Phe Gly Glu Ser Ala Gly<br>        210                      215                      220 | 672 |
| ggg gaa agt gtc tct gtt ctg gtg ttg tct ccc ttg gcc aag aac ctc<br>Gly Glu Ser Val Ser Val Leu Val Leu Ser Pro Leu Ala Lys Asn Leu<br>225                              230                        235                      240 | 720 |
| ttc cac cgg gcc atc tct gag agt ggc gtg gcc ctc act gtt gcc ctg<br>Phe His Arg Ala Ile Ser Glu Ser Gly Val Ala Leu Thr Val Ala Leu<br>                        245                       250                      255 | 768 |
| gtc agg aag gac atg aag gct gca gct aag caa att gct gtc ctt gct<br>Val Arg Lys Asp Met Lys Ala Ala Ala Lys Gln Ile Ala Val Leu Ala<br>                  260                       265                      270 | 816 |
| ggg tgt aaa acc acc acc tcg gct gtc ttt gtt cac tgc ctg cgc cag<br>Gly Cys Lys Thr Thr Thr Ser Ala Val Phe Val His Cys Leu Arg Gln<br>            275                      280                      285 | 864 |
| aag tcg gag gac gag ctc ttg gac tta acg ctg aag atg aaa ttt tta<br>Lys Ser Glu Asp Glu Leu Leu Asp Leu Thr Leu Lys Met Lys Phe Leu<br>        290                      295                      300 | 912 |
| act ctt gat ttt cat gga gac caa aga gag agc cat ccc ttc ctg ccc<br>Thr Leu Asp Phe His Gly Asp Gln Arg Glu Ser His Pro Phe Leu Pro<br>305                              310                        315                      320 | 960 |
| act gtg gtg gat gga gtg ctg ctg ccc aag atg cct gaa gag att ctg<br>Thr Val Val Asp Gly Val Leu Leu Pro Lys Met Pro Glu Glu Ile Leu<br>                        325                       330                      335 | 1008 |
| gct gag aag gat ttc aac act gtc ccc tac atc gtg gga atc aac aag<br>Ala Glu Lys Asp Phe Asn Thr Val Pro Tyr Ile Val Gly Ile Asn Lys<br>                  340                       345                      350 | 1056 |
| caa gag ttt ggc tgg ctt ctg cca acg atg atg ggc ttc ccc ctc tct<br>Gln Glu Phe Gly Trp Leu Leu Pro Thr Met Met Gly Phe Pro Leu Ser<br>                355                       360                      365 | 1104 |
| gaa ggc aag ctg gac cag aag acg gcc acg tca ctc ctg tgg aag tcc<br>Glu Gly Lys Leu Asp Gln Lys Thr Ala Thr Ser Leu Leu Trp Lys Ser<br>        370                      375                      380 | 1152 |

```
tac ccc atc gct aac atc cct gag gaa ctg act cca gtg gcc act gac   1200
Tyr Pro Ile Ala Asn Ile Pro Glu Glu Leu Thr Pro Val Ala Thr Asp
385                 390                 395                 400 aag tat ttg ggg ggg aca gac gac ccc gtc aaa aag aaa gac ctg ttc   1248
Lys Tyr Leu Gly Gly Thr Asp Asp Pro Val Lys Lys Lys Asp Leu Phe
            405                 410                 415 ctg gac ttg atg ggg gat gtg gtg ttt ggt gtc cca tct gtg acg gtg   1296
Leu Asp Leu Met Gly Asp Val Val Phe Gly Val Pro Ser Val Thr Val
                420                 425                 430 gcc cgt caa cac aga gat gca gga gcc ccc acc tac atg tat gag ttt   1344
Ala Arg Gln His Arg Asp Ala Gly Ala Pro Thr Tyr Met Tyr Glu Phe
435                 440                 445 cag tat cgc cca agc ttc tca tcg gac aag aaa ccc aag acg gtg atc   1392
Gln Tyr Arg Pro Ser Phe Ser Ser Asp Lys Lys Pro Lys Thr Val Ile
    450                 455                 460 ggg gac cac ggg gat gag atc ttc tcc gtc ttt ggt ttt cca ctg tta   1440
Gly Asp His Gly Asp Glu Ile Phe Ser Val Phe Gly Phe Pro Leu Leu
465                 470                 475                 480 aaa ggc gat gcc cca gaa gag gag gtc agt ctc agc aag acg gtg atg   1488
Lys Gly Asp Ala Pro Glu Glu Glu Val Ser Leu Ser Lys Thr Val Met
            485                 490                 495 aaa ttc tgg gcc aac ttt gct cgc agt ggg aac ccc aat ggg gag ggg   1536
Lys Phe Trp Ala Asn Phe Ala Arg Ser Gly Asn Pro Asn Gly Glu Gly
                500                 505                 510 ctg ccc cat tgg ccg atg tac gac cag gaa gaa ggg tac ctt cag atc   1584
Leu Pro His Trp Pro Met Tyr Asp Gln Glu Glu Gly Tyr Leu Gln Ile
515                 520                 525 ggc gtc aac acc cag gca gcc aag agg ctg aaa ggt gaa gaa gtg gcc   1632
Gly Val Asn Thr Gln Ala Ala Lys Arg Leu Lys Gly Glu Glu Val Ala
    530                 535                 540 ttc tgg aac gat ctc ctg tcc aag gag gca gca aag aag cca ccc aag   1680
Phe Trp Asn Asp Leu Leu Ser Lys Glu Ala Ala Lys Lys Pro Pro Lys
545                 550                 555                 560 ata aag cat gct gag ctg tga                                        1701
Ile Lys His Ala Glu Leu
                565

<210> SEQ ID NO 2
<211> LENGTH: 566
<212> TYPE: PRT
<213> ORGANISM: Sus scrofa

<400> SEQUENCE: 2

Met Trp Leu Leu Pro Leu Val Leu Thr Ser Leu Ala Ser Ser Ala Thr
1               5                   10                  15

Trp Ala Gly Gln Pro Ala Ser Pro Pro Val Val Asp Thr Ala Gln Gly
            20                  25                  30

Arg Val Leu Gly Lys Tyr Val Ser Leu Glu Gly Leu Ala Gln Pro Val
        35                  40                  45

Ala Val Phe Leu Gly Val Pro Phe Ala Lys Pro Pro Leu Gly Ser Leu
    50                  55                  60

Arg Phe Ala Pro Pro Gln Pro Ala Glu Pro Trp Ser Phe Val Lys Asn
65                  70                  75                  80

Thr Thr Ser Tyr Pro Pro Met Cys Cys Gln Asp Pro Val Glu Gln
                85                  90                  95

Met Thr Ser Asp Leu Phe Thr Asn Gly Lys Glu Arg Leu Thr Leu Glu
            100                 105                 110

Phe Ser Glu Asp Cys Leu Tyr Leu Asn Ile Tyr Thr Pro Ala Asp Leu
        115                 120                 125
```

```
Thr Lys Arg Gly Arg Leu Pro Val Met Val Trp Ile His Gly Gly
130                 135                 140

Leu Val Leu Gly Gly Ala Pro Met Tyr Asp Gly Val Val Leu Ala Ala
145                 150                 155                 160

His Glu Asn Val Val Val Ala Ile Gln Tyr Arg Leu Gly Ile Trp
                165                 170                 175

Gly Phe Phe Ser Thr Gly Asp Glu His Ser Arg Gly Asn Trp Gly His
                180                 185                 190

Leu Asp Gln Val Ala Ala Leu His Trp Val Gln Glu Asn Ile Ala Asn
                195                 200                 205

Phe Gly Gly Asp Pro Gly Ser Val Thr Ile Phe Gly Glu Ser Ala Gly
210                 215                 220

Gly Glu Ser Val Ser Val Leu Val Leu Ser Pro Leu Ala Lys Asn Leu
225                 230                 235                 240

Phe His Arg Ala Ile Ser Glu Ser Gly Val Ala Leu Thr Val Ala Leu
                245                 250                 255

Val Arg Lys Asp Met Lys Ala Ala Lys Gln Ile Ala Val Leu Ala
                260                 265                 270

Gly Cys Lys Thr Thr Thr Ser Ala Val Phe Val His Cys Leu Arg Gln
                275                 280                 285

Lys Ser Glu Asp Glu Leu Leu Asp Leu Thr Leu Lys Met Lys Phe Leu
290                 295                 300

Thr Leu Asp Phe His Gly Asp Gln Arg Glu Ser His Pro Phe Leu Pro
305                 310                 315                 320

Thr Val Val Asp Gly Val Leu Leu Pro Lys Met Pro Glu Glu Ile Leu
                325                 330                 335

Ala Glu Lys Asp Phe Asn Thr Val Pro Tyr Ile Val Gly Ile Asn Lys
                340                 345                 350

Gln Glu Phe Gly Trp Leu Leu Pro Thr Met Met Gly Phe Pro Leu Ser
                355                 360                 365

Glu Gly Lys Leu Asp Gln Lys Thr Ala Thr Ser Leu Leu Trp Lys Ser
                370                 375                 380

Tyr Pro Ile Ala Asn Ile Pro Glu Glu Leu Thr Pro Val Ala Thr Asp
385                 390                 395                 400

Lys Tyr Leu Gly Gly Thr Asp Asp Pro Val Lys Lys Asp Leu Phe
                405                 410                 415

Leu Asp Leu Met Gly Asp Val Val Phe Gly Val Pro Ser Val Thr Val
                420                 425                 430

Ala Arg Gln His Arg Asp Ala Gly Ala Pro Thr Tyr Met Tyr Glu Phe
                435                 440                 445

Gln Tyr Arg Pro Ser Phe Ser Ser Asp Lys Leu Pro Lys Thr Val Ile
                450                 455                 460

Gly Asp His Gly Asp Glu Ile Phe Ser Val Phe Gly Phe Pro Leu Leu
465                 470                 475                 480

Lys Gly Asp Ala Pro Glu Glu Val Ser Leu Ser Lys Thr Val Met
                485                 490                 495

Lys Phe Trp Ala Asn Phe Ala Arg Ser Gly Asn Pro Asn Gly Glu Gly
                500                 505                 510

Leu Pro His Trp Pro Met Tyr Asp Gln Glu Glu Gly Tyr Leu Gln Ile
                515                 520                 525

Gly Val Asn Thr Gln Ala Ala Lys Arg Leu Lys Gly Glu Glu Val Ala
530                 535                 540
```

```
Phe Trp Asn Asp Leu Leu Ser Lys Glu Ala Ala Lys Lys Pro Pro Lys
545                 550                 555                 560

Ile Lys His Ala Glu Leu
            565
```

<210> SEQ ID NO 3
<211> LENGTH: 33
<212> TYPE: DNA
<213> ORGANISM: artificial sequence
<220> FEATURE:
<223> OTHER INFORMATION: primer

<400> SEQUENCE: 3
cagaattcat ggctatcggg cagccagcct cgc                          33

<210> SEQ ID NO 4
<211> LENGTH: 30
<212> TYPE: DNA
<213> ORGANISM: artificial sequence
<220> FEATURE:
<223> OTHER INFORMATION: primer

<400> SEQUENCE: 4
ccggaattca gcctcccctt cacagctcag                              30

<210> SEQ ID NO 5
<211> LENGTH: 1698
<212> TYPE: DNA
<213> ORGANISM: Sus scrofa
<220> FEATURE:
<221> NAME/KEY: CDS
<222> LOCATION: (1)..(1698)
<223> OTHER INFORMATION: Alternative Pig Liver Esterase

<400> SEQUENCE: 5

```
atg tgg ctt ctc ccg ctg gtc ctg acc tcc ctc gcc tct tct gca act    48
Met Trp Leu Leu Pro Leu Val Leu Thr Ser Leu Ala Ser Ser Ala Thr
1               5                   10                  15 tgg ggg cag cca gcc tcg ccg cct gtt gtg gac act gcc cag ggc cga    96
Trp Gly Gln Pro Ala Ser Pro Pro Val Val Asp Thr Ala Gln Gly Arg
            20                  25                  30 gtc ctg ggg aag tac gtc agc tta gaa ggc ctg gca cag ccg gtg gcc   144
Val Leu Gly Lys Tyr Val Ser Leu Glu Gly Leu Ala Gln Pro Val Ala
        35                  40                  45 gtc ttc ctg gga gtc cct ttt gcc aag ccc cct ctc gga tcc ttg agg   192
Val Phe Leu Gly Val Pro Phe Ala Lys Pro Pro Leu Gly Ser Leu Arg
    50                  55                  60 ttt gct ccg ccg cag cct gca gaa cca tgg agc ttc gtg aag aac acc   240
Phe Ala Pro Pro Gln Pro Ala Glu Pro Trp Ser Phe Val Lys Asn Thr
65                  70                  75                  80 acc tcc tac cct ccc atg tgc tgc caa gag cca att ggg gga cag atg   288
Thr Ser Tyr Pro Pro Met Cys Cys Gln Glu Pro Ile Gly Gly Gln Met
                85                  90                  95 ctc tca gat cta ttt acc aac aga aag gag agg ctc att ccg gag ttt   336
Leu Ser Asp Leu Phe Thr Asn Arg Lys Glu Arg Leu Ile Pro Glu Phe
            100                 105                 110 tct gaa gac tgt ctc tac cta aat att tac acc cct gct gac ctg aca   384
Ser Glu Asp Cys Leu Tyr Leu Asn Ile Tyr Thr Pro Ala Asp Leu Thr
        115                 120                 125 aag agg ggc aga ctg ccg gtg atg gtg tgg atc cac gga gga ggt ctg   432
Lys Arg Gly Arg Leu Pro Val Met Val Trp Ile His Gly Gly Gly Leu
    130                 135                 140 gtg gtg ggc ggg gct tcc acc tat gat gga ctg gcc ctc gct gcg cat   480
```

|  |  |  |  |  |  |  |  |  |  |  |  |  |  |  |  |
|---|---|---|---|---|---|---|---|---|---|---|---|---|---|---|---|
| Val | Val | Gly | Gly | Ala | Ser | Thr | Tyr | Asp | Gly | Leu | Ala | Leu | Ala | Ala | His |
| 145 |  |  |  |  | 150 |  |  |  |  | 155 |  |  |  |  | 160 |

```
gaa aac gtg gtg gtg gtg gcc atc cag tac cgc ctg ggc atc tgg gga       528
Glu Asn Val Val Val Val Ala Ile Gln Tyr Arg Leu Gly Ile Trp Gly
                165                 170                 175 ttc ttc agc aca ggg gac gaa cac agc cgg ggc aac tgg ggt cac ttg       576
Phe Phe Ser Thr Gly Asp Glu His Ser Arg Gly Asn Trp Gly His Leu
            180                 185                 190 gac cag gtg gcc gca ctg cac tgg gtc cag gag aac atc gcc aac ttt       624
Asp Gln Val Ala Ala Leu His Trp Val Gln Glu Asn Ile Ala Asn Phe
        195                 200                 205 gga ggc gac cca ggc tct gtg acc atc ttt gga gag tca gca gga ggg       672
Gly Gly Asp Pro Gly Ser Val Thr Ile Phe Gly Glu Ser Ala Gly Gly
    210                 215                 220 gaa agt gtc tct gtt ctg gtg ttg tct ccc ttg gcc aag aac ctc ttc       720
Glu Ser Val Ser Val Leu Val Leu Ser Pro Leu Ala Lys Asn Leu Phe
225                 230                 235                 240 cac cgg gcc atc tct gag agt ggc gtg gcc ttc act gct ggc ctg gtc       768
His Arg Ala Ile Ser Glu Ser Gly Val Ala Phe Thr Ala Gly Leu Val
                245                 250                 255 agg aag gac atg aag gct gca gct aag caa att gct gtc ctt gct ggg       816
Arg Lys Asp Met Lys Ala Ala Ala Lys Gln Ile Ala Val Leu Ala Gly
            260                 265                 270 tgt aaa acc acc acc tcg gct gtc ttt gtt cac tgc ctg cgc cag aag       864
Cys Lys Thr Thr Thr Ser Ala Val Phe Val His Cys Leu Arg Gln Lys
        275                 280                 285 tcg gag gac gag ctc ttg gac tta acg ctg aag atg aaa ttt ttc gct       912
Ser Glu Asp Glu Leu Leu Asp Leu Thr Leu Lys Met Lys Phe Phe Ala
    290                 295                 300 ctt gat ttg cat gga gac ccc aga gag agc cat ccc ttc ctg acc act       960
Leu Asp Leu His Gly Asp Pro Arg Glu Ser His Pro Phe Leu Thr Thr
305                 310                 315                 320 gtg gtg gat gga gtg ctg ctg ccc aag atg cct gaa gag att ctg gct      1008
Val Val Asp Gly Val Leu Leu Pro Lys Met Pro Glu Glu Ile Leu Ala
                325                 330                 335 gaa aag gat ttc aac act gtc ccc tac atc gtg gga atc aac aag caa      1056
Glu Lys Asp Phe Asn Thr Val Pro Tyr Ile Val Gly Ile Asn Lys Gln
            340                 345                 350 gag ttt ggc tgg ctt ctg cca acg atg atg ggc ttc ccc ctc tct gaa      1104
Glu Phe Gly Trp Leu Leu Pro Thr Met Met Gly Phe Pro Leu Ser Glu
        355                 360                 365 ggc aag ctg gac cag aag acg gcc acg tca ctc ctg tgg aag tcc tac      1152
Gly Lys Leu Asp Gln Lys Thr Ala Thr Ser Leu Leu Trp Lys Ser Tyr
    370                 375                 380 ccc atc gct aac atc cct gag gaa ctg act cca gtg gcc act gac aag      1200
Pro Ile Ala Asn Ile Pro Glu Glu Leu Thr Pro Val Ala Thr Asp Lys
385                 390                 395                 400 tat ttg ggg ggg aca gac gac ccc gtc aaa aag aaa gac ctg ttc ctg      1248
Tyr Leu Gly Gly Thr Asp Asp Pro Val Lys Lys Lys Asp Leu Phe Leu
                405                 410                 415 gac ttg atg ggg gat gtg gtg ttt ggt gtc cca tct gtg acg gtg gcc      1296
Asp Leu Met Gly Asp Val Val Phe Gly Val Pro Ser Val Thr Val Ala
            420                 425                 430 cgt caa cac aga gat gca gga gcc ccc acc tac atg tat gag ttt cag      1344
Arg Gln His Arg Asp Ala Gly Ala Pro Thr Tyr Met Tyr Glu Phe Gln
        435                 440                 445 tat cgc cca agc ttc tca tcg gac aag aaa ccc aag acg gtg atc ggg      1392
Tyr Arg Pro Ser Phe Ser Ser Asp Lys Lys Pro Lys Thr Val Ile Gly
    450                 455                 460
```

```
gac cac ggg gat gag atc ttc tcc gtc ttt ggt ttt cca ctg tta aaa    1440
Asp His Gly Asp Glu Ile Phe Ser Val Phe Gly Phe Pro Leu Leu Lys
465             470                 475                 480 ggc gat gcc cca gaa gag gag gtc agt ctc agc aag acg gtg atg aaa    1488
Gly Asp Ala Pro Glu Glu Glu Val Ser Leu Ser Lys Thr Val Met Lys
                485                 490                 495 ttc tgg gcc aac ttt gct cgc agt ggg aac ccc aat ggg gag ggg ctg    1536
Phe Trp Ala Asn Phe Ala Arg Ser Gly Asn Pro Asn Gly Glu Gly Leu
    500                 505                 510 ccc cat tgg ccg atg tac gac cag gaa gaa ggg tac ctt cag atc ggc    1584
Pro His Trp Pro Met Tyr Asp Gln Glu Glu Gly Tyr Leu Gln Ile Gly
        515                 520                 525 gtc aac acc cag gca gcc aag agg ctg aaa ggt gaa gaa gtg gcc ttc    1632
Val Asn Thr Gln Ala Ala Lys Arg Leu Lys Gly Glu Glu Val Ala Phe
            530                 535                 540 tgg aac gat ctc ctg tcc aag gag gca gca aag aag cca ccc aag ata    1680
Trp Asn Asp Leu Leu Ser Lys Glu Ala Ala Lys Lys Pro Pro Lys Ile
545                 550                 555                 560 aag cat gct gag ctg tga                                            1698
Lys His Ala Glu Leu
                565
```

<210> SEQ ID NO 6
<211> LENGTH: 565
<212> TYPE: PRT
<213> ORGANISM: Sus scrofa

<400> SEQUENCE: 6

```
Met Trp Leu Leu Pro Leu Val Leu Thr Ser Leu Ala Ser Ser Ala Thr
1               5                   10                  15

Trp Gly Gln Pro Ala Ser Pro Pro Val Val Asp Thr Ala Gln Gly Arg
            20                  25                  30

Val Leu Gly Lys Tyr Val Ser Leu Glu Gly Leu Ala Gln Pro Val Ala
        35                  40                  45

Val Phe Leu Gly Val Pro Phe Ala Lys Pro Pro Leu Gly Ser Leu Arg
    50                  55                  60

Phe Ala Pro Pro Gln Pro Ala Glu Pro Trp Ser Phe Val Lys Asn Thr
65                  70                  75                  80

Thr Ser Tyr Pro Pro Met Cys Cys Gln Glu Pro Ile Gly Gly Gln Met
                85                  90                  95

Leu Ser Asp Leu Phe Thr Asn Arg Lys Glu Arg Leu Ile Pro Glu Phe
            100                 105                 110

Ser Glu Asp Cys Leu Tyr Leu Asn Ile Tyr Thr Pro Ala Asp Leu Thr
        115                 120                 125

Lys Arg Gly Arg Leu Pro Val Met Val Trp Ile His Gly Gly Gly Leu
    130                 135                 140

Val Val Gly Gly Ala Ser Thr Tyr Asp Gly Leu Ala Leu Ala Ala His
145                 150                 155                 160

Glu Asn Val Val Val Ala Ile Gln Tyr Arg Leu Gly Ile Trp Gly
                165                 170                 175

Phe Phe Ser Thr Gly Asp Glu His Ser Arg Gly Asn Trp Gly His Leu
            180                 185                 190

Asp Gln Val Ala Ala Leu His Trp Val Gln Glu Asn Ile Ala Asn Phe
        195                 200                 205

Gly Gly Asp Pro Gly Ser Val Thr Ile Phe Gly Glu Ser Ala Gly Gly
    210                 215                 220

Glu Ser Val Ser Val Leu Val Leu Ser Pro Leu Ala Lys Asn Leu Phe
```

```
            225                 230                 235                 240
    His Arg Ala Ile Ser Glu Ser Gly Val Ala Phe Thr Ala Gly Leu Val
                        245                 250                 255

Arg Lys Asp Met Lys Ala Ala Lys Gln Ile Ala Val Leu Ala Gly
                260                 265                 270

Cys Lys Thr Thr Thr Ser Ala Val Phe Val His Cys Leu Arg Gln Lys
                275                 280                 285

Ser Glu Asp Glu Leu Leu Asp Leu Thr Leu Lys Met Lys Phe Phe Ala
                290                 295                 300

Leu Asp Leu His Gly Asp Pro Arg Glu Ser His Pro Phe Leu Thr Thr
    305                 310                 315                 320

Val Val Asp Gly Val Leu Leu Pro Lys Met Pro Glu Glu Ile Leu Ala
                        325                 330                 335

Glu Lys Asp Phe Asn Thr Val Pro Tyr Ile Val Gly Ile Asn Lys Gln
                        340                 345                 350

Glu Phe Gly Trp Leu Leu Pro Thr Met Met Gly Phe Pro Leu Ser Glu
                        355                 360                 365

Gly Lys Leu Asp Gln Lys Thr Ala Thr Ser Leu Leu Trp Lys Ser Tyr
                370                 375                 380

Pro Ile Ala Asn Ile Pro Glu Glu Leu Thr Pro Val Ala Thr Asp Lys
    385                 390                 395                 400

Tyr Leu Gly Gly Thr Asp Asp Pro Val Lys Lys Asp Leu Phe Leu
                        405                 410                 415

Asp Leu Met Gly Asp Val Val Phe Gly Val Pro Ser Val Thr Val Ala
                        420                 425                 430

Arg Gln His Arg Asp Ala Gly Ala Pro Thr Tyr Met Tyr Glu Phe Gln
                435                 440                 445

Tyr Arg Pro Ser Phe Ser Ser Asp Lys Lys Pro Lys Thr Val Ile Gly
                450                 455                 460

Asp His Gly Asp Glu Ile Phe Ser Val Phe Gly Phe Pro Leu Leu Lys
    465                 470                 475                 480

Gly Asp Ala Pro Glu Glu Val Ser Leu Ser Lys Thr Val Met Lys
                        485                 490                 495

Phe Trp Ala Asn Phe Ala Arg Ser Gly Asn Pro Asn Gly Glu Gly Leu
                500                 505                 510

Pro His Trp Pro Met Tyr Asp Gln Glu Gly Tyr Leu Gln Ile Gly
                515                 520                 525

Val Asn Thr Gln Ala Ala Lys Arg Leu Lys Gly Glu Glu Val Ala Phe
                530                 535                 540

Trp Asn Asp Leu Leu Ser Lys Glu Ala Ala Lys Lys Pro Pro Lys Ile
    545                 550                 555                 560

Lys His Ala Glu Leu
                565

<210> SEQ ID NO 7
<211> LENGTH: 43
<212> TYPE: DNA
<213> ORGANISM: artificial sequence
<220> FEATURE:
<223> OTHER INFORMATION: primer

<400> SEQUENCE: 7
tcttcgaaga attcacgatg agatttcctt caatttttac tgc                        43

<210> SEQ ID NO 8
```

```
<211> LENGTH: 36
<212> TYPE: DNA
<213> ORGANISM: artificial sequence
<220> FEATURE:
<223> OTHER INFORMATION: primer

<400> SEQUENCE: 8
gaggctggct gcccagcttc agcctctctt ttctcg                                36

<210> SEQ ID NO 9
<211> LENGTH: 33
<212> TYPE: DNA
<213> ORGANISM: artificial sequence
<220> FEATURE:
<223> OTHER INFORMATION: primer

<400> SEQUENCE: 9
agagaggctg aagctgggca gccagcctcg ccg                                   33

<210> SEQ ID NO 10
<211> LENGTH: 40
<212> TYPE: DNA
<213> ORGANISM: artificial sequence
<220> FEATURE:
<223> OTHER INFORMATION: primer

<400> SEQUENCE: 10
atggtaccga attctcactt tatcttgggt ggcttctttg                            40

<210> SEQ ID NO 11
<211> LENGTH: 1650
<212> TYPE: DNA
<213> ORGANISM: artificial sequence
<220> FEATURE:
<223> OTHER INFORMATION: protein encoding esterase activity
<220> FEATURE:
<221> NAME/KEY: CDS
<222> LOCATION: (1)..(1650)

<400> SEQUENCE: 11
```

| | | | | | | | | | | | | | | | | |
|---|---|---|---|---|---|---|---|---|---|---|---|---|---|---|---|---|
| atg | gga | caa | cca | gct | tcg | ccg | cct | gtc | gtt | gat | acc | gct | caa | gga | cga | 48 |
| Met | Gly | Gln | Pro | Ala | Ser | Pro | Pro | Val | Val | Asp | Thr | Ala | Gln | Gly | Arg | |
| 1 | | | | 5 | | | | | 10 | | | | | 15 | | |
| gtc | ttg | ggt | aag | tac | gtc | tct | tta | gag | gga | ttg | gca | caa | ccg | gtt | gct | 96 |
| Val | Leu | Gly | Lys | Tyr | Val | Ser | Leu | Glu | Gly | Leu | Ala | Gln | Pro | Val | Ala | |
| | | | 20 | | | | | 25 | | | | | 30 | | | |
| gtc | ttc | ttg | gga | gtc | cct | ttt | gct | aag | cca | cct | ctt | gga | tct | ttg | agg | 144 |
| Val | Phe | Leu | Gly | Val | Pro | Phe | Ala | Lys | Pro | Pro | Leu | Gly | Ser | Leu | Arg | |
| | | 35 | | | | | 40 | | | | | 45 | | | | |
| ttt | gcc | ccg | ccg | caa | cca | gca | gag | cca | tgg | tct | ttc | gtt | aag | aac | act | 192 |
| Phe | Ala | Pro | Pro | Gln | Pro | Ala | Glu | Pro | Trp | Ser | Phe | Val | Lys | Asn | Thr | |
| | 50 | | | | | 55 | | | | | 60 | | | | | |
| act | tcc | tac | cct | cca | atg | tgt | tgt | caa | gaa | cca | atc | gga | gga | caa | atg | 240 |
| Thr | Ser | Tyr | Pro | Pro | Met | Cys | Cys | Gln | Glu | Pro | Ile | Gly | Gly | Gln | Met | |
| 65 | | | | | 70 | | | | | 75 | | | | | 80 | |
| ctt | tca | gac | cta | ttc | act | aac | aga | aag | gaa | agg | ctt | atc | ccg | gag | ttc | 288 |
| Leu | Ser | Asp | Leu | Phe | Thr | Asn | Arg | Lys | Glu | Arg | Leu | Ile | Pro | Glu | Phe | |
| | | | | 85 | | | | | 90 | | | | | 95 | | |
| tct | gag | gat | tgc | ctt | tac | cta | aat | att | tac | act | cct | gcc | gat | ttg | aca | 336 |
| Ser | Glu | Asp | Cys | Leu | Tyr | Leu | Asn | Ile | Tyr | Thr | Pro | Ala | Asp | Leu | Thr | |
| | | | 100 | | | | | 105 | | | | | 110 | | | |
| aag | agg | ggt | agg | ttg | ccg | gtt | atg | gtt | tgg | att | cat | gga | gga | ggt | ttg | 384 |
| Lys | Arg | Gly | Arg | Leu | Pro | Val | Met | Val | Trp | Ile | His | Gly | Gly | Gly | Leu | |
| | | 115 | | | | | 120 | | | | | 125 | | | | |

```
gtt gtt ggc gga gca tcc act tat gac gga ttg gct ctt gcc gcg cac         432
Val Val Gly Gly Ala Ser Thr Tyr Asp Gly Leu Ala Leu Ala Ala His
    130                 135                 140 gag aac gtt gtt gtt gtt gct att caa tac cgt ttg ggt att tgg gga         480
Glu Asn Val Val Val Val Ala Ile Gln Tyr Arg Leu Gly Ile Trp Gly
145                 150                 155                 160 ttt ttc tcc aca gga gat gag cat tcc cgt gga aac tgg ggc cat tta         528
Phe Phe Ser Thr Gly Asp Glu His Ser Arg Gly Asn Trp Gly His Leu
                165                 170                 175 gat caa gtt gct gca ttg cat tgg gtc caa gaa aac att gct aac ttc         576
Asp Gln Val Ala Ala Leu His Trp Val Gln Glu Asn Ile Ala Asn Phe
            180                 185                 190 gga ggt gat cca ggt tct gtt act att ttc gga gaa tca gca ggc gga         624
Gly Gly Asp Pro Gly Ser Val Thr Ile Phe Gly Glu Ser Ala Gly Gly
        195                 200                 205 gag agt gtc tct gta ttg gtt tta tca cca tta gct aag aac ctt ttt         672
Glu Ser Val Ser Val Leu Val Leu Ser Pro Leu Ala Lys Asn Leu Phe
    210                 215                 220 cat cgt gct att tcc gaa agt ggt gtt gct ttt acc gcc ggt ttg gtc         720
His Arg Ala Ile Ser Glu Ser Gly Val Ala Phe Thr Ala Gly Leu Val
225                 230                 235                 240 agg aag gat atg aag gcc gca gcc aag cag atc gct gtc ctt gca gga         768
Arg Lys Asp Met Lys Ala Ala Ala Lys Gln Ile Ala Val Leu Ala Gly
                245                 250                 255 tgc aaa act act act tcg gca gtc ttc gtg cat tgt ttg cgt caa aag         816
Cys Lys Thr Thr Thr Ser Ala Val Phe Val His Cys Leu Arg Gln Lys
            260                 265                 270 tcg gaa gat gaa ctt tta gac ctc acg ttg aag atg aaa ttc ttt gcc         864
Ser Glu Asp Glu Leu Leu Asp Leu Thr Leu Lys Met Lys Phe Phe Ala
        275                 280                 285 ctt gac tta cac gga gat cca agg gaa tct cac cct ttt ttg acc act         912
Leu Asp Leu His Gly Asp Pro Arg Glu Ser His Pro Phe Leu Thr Thr
    290                 295                 300 gtt gtt gac gga gtt ttg ttg cct aag atg cct gag gaa atc ttg gcc         960
Val Val Asp Gly Val Leu Leu Pro Lys Met Pro Glu Glu Ile Leu Ala
305                 310                 315                 320 gag aag gac ttt aac acc gtc cca tac att gtt gga att aac aag cag        1008
Glu Lys Asp Phe Asn Thr Val Pro Tyr Ile Val Gly Ile Asn Lys Gln
                325                 330                 335 gag ttc gga tgg ctt ttg cca acg atg atg gga ttt cct ctt tcc gag        1056
Glu Phe Gly Trp Leu Leu Pro Thr Met Met Gly Phe Pro Leu Ser Glu
            340                 345                 350 gga aag ttg gat caa aag acg gct acg tca ctt ttg tgg aag tcc tac        1104
Gly Lys Leu Asp Gln Lys Thr Ala Thr Ser Leu Leu Trp Lys Ser Tyr
        355                 360                 365 cca att gcc aac att cct gaa gag ttg acc cca gtt gct acc gat aag        1152
Pro Ile Ala Asn Ile Pro Glu Glu Leu Thr Pro Val Ala Thr Asp Lys
    370                 375                 380 tat tta gga gga aca gat gat cct gtc aaa aag aaa gat ttg ttt ttg        1200
Tyr Leu Gly Gly Thr Asp Asp Pro Val Lys Lys Lys Asp Leu Phe Leu
385                 390                 395                 400 gat ctg atg gga gac gtt gtt ttc ggc gtc cca tca gtt acg gtt gct        1248
Asp Leu Met Gly Asp Val Val Phe Gly Val Pro Ser Val Thr Val Ala
                405                 410                 415 cgt cag cat agg gac gca gga gct cca act tac atg tat gag ttc caa        1296
Arg Gln His Arg Asp Ala Gly Ala Pro Thr Tyr Met Tyr Glu Phe Gln
            420                 425                 430 tat cgt cca tct ttt tca tcg gat aag aaa cct aag acg gtt att gga        1344
Tyr Arg Pro Ser Phe Ser Ser Asp Lys Lys Pro Lys Thr Val Ile Gly
        435                 440                 445
```

```
gat cat gga gac gaa att ttt tcc gtc ttc ggc ttc cca ttg ctc aaa      1392
Asp His Gly Asp Glu Ile Phe Ser Val Phe Gly Phe Pro Leu Leu Lys
    450                 455                 460 ggt gac gct cca gag gaa gaa gtc agt ctt tct aag acg gtt atg aaa      1440
Gly Asp Ala Pro Glu Glu Glu Val Ser Leu Ser Lys Thr Val Met Lys
465                 470                 475                 480 ttt tgg gct aac ttc gcc cgt agt gga aac cct aat gga gaa gga ttg      1488
Phe Trp Ala Asn Phe Ala Arg Ser Gly Asn Pro Asn Gly Glu Gly Leu
                485                 490                 495 cct cac tgg ccg atg tac gat caa gag gag gga tac ctt caa att ggt      1536
Pro His Trp Pro Met Tyr Asp Gln Glu Glu Gly Tyr Leu Gln Ile Gly
            500                 505                 510 gtc aac act caa gca gct aag agg ttg aaa ggc gag gag gtt gct ttt      1584
Val Asn Thr Gln Ala Ala Lys Arg Leu Lys Gly Glu Glu Val Ala Phe
        515                 520                 525 tgg aac gac ctg ttg tcc aag gaa gca gca aag aag cca cct aag ata      1632
Trp Asn Asp Leu Leu Ser Lys Glu Ala Ala Lys Lys Pro Pro Lys Ile
    530                 535                 540 aag cac gcc gaa ttg taa                                              1650
Lys His Ala Glu Leu
545

<210> SEQ ID NO 12
<211> LENGTH: 549
<212> TYPE: PRT
<213> ORGANISM: artificial sequence
<220> FEATURE:
<223> OTHER INFORMATION: Synthetic Construct

<400> SEQUENCE: 12

Met Gly Gln Pro Ala Ser Pro Pro Val Val Asp Thr Ala Gln Gly Arg
1               5                   10                  15

Val Leu Gly Lys Tyr Val Ser Leu Glu Gly Leu Ala Gln Pro Val Ala
            20                  25                  30

Val Phe Leu Gly Val Pro Phe Ala Lys Pro Pro Leu Gly Ser Leu Arg
        35                  40                  45

Phe Ala Pro Pro Gln Pro Ala Glu Pro Trp Ser Phe Val Lys Asn Thr
    50                  55                  60

Thr Ser Tyr Pro Pro Met Cys Cys Gln Glu Pro Ile Gly Gly Gln Met
65                  70                  75                  80

Leu Ser Asp Leu Phe Thr Asn Arg Lys Glu Arg Leu Ile Pro Glu Phe
                85                  90                  95

Ser Glu Asp Cys Leu Tyr Leu Asn Ile Tyr Thr Pro Ala Asp Leu Thr
            100                 105                 110

Lys Arg Gly Arg Leu Pro Val Met Val Trp Ile His Gly Gly Gly Leu
        115                 120                 125

Val Val Gly Gly Ala Ser Thr Tyr Asp Gly Leu Ala Leu Ala Ala His
    130                 135                 140

Glu Asn Val Val Val Ala Ile Gln Tyr Arg Leu Gly Ile Trp Gly
145                 150                 155                 160

Phe Phe Ser Thr Gly Asp Glu His Ser Arg Gly Asn Trp Gly His Leu
                165                 170                 175

Asp Gln Val Ala Ala Leu His Trp Val Gln Glu Asn Ile Ala Asn Phe
            180                 185                 190

Gly Gly Asp Pro Gly Ser Val Thr Ile Phe Gly Glu Ser Ala Gly Gly
        195                 200                 205

Glu Ser Val Ser Val Leu Val Leu Ser Pro Leu Ala Lys Asn Leu Phe
```

```
            210                 215                 220
His Arg Ala Ile Ser Glu Ser Gly Val Ala Phe Thr Ala Gly Leu Val
225                 230                 235                 240

Arg Lys Asp Met Lys Ala Ala Lys Gln Ile Ala Val Leu Ala Gly
                245                 250                 255

Cys Lys Thr Thr Thr Ser Ala Val Phe Val His Cys Leu Arg Gln Lys
                260                 265                 270

Ser Glu Asp Glu Leu Leu Asp Leu Thr Leu Lys Met Lys Phe Phe Ala
                275                 280                 285

Leu Asp Leu His Gly Asp Pro Arg Glu Ser His Pro Phe Leu Thr Thr
290                 295                 300

Val Val Asp Gly Val Leu Leu Pro Lys Met Pro Glu Glu Ile Leu Ala
305                 310                 315                 320

Glu Lys Asp Phe Asn Thr Val Pro Tyr Ile Val Gly Ile Asn Lys Gln
                325                 330                 335

Glu Phe Gly Trp Leu Leu Pro Thr Met Met Gly Phe Pro Leu Ser Glu
                340                 345                 350

Gly Lys Leu Asp Gln Lys Thr Ala Thr Ser Leu Leu Trp Lys Ser Tyr
                355                 360                 365

Pro Ile Ala Asn Ile Pro Glu Glu Leu Thr Pro Val Ala Thr Asp Lys
                370                 375                 380

Tyr Leu Gly Gly Thr Asp Asp Pro Val Lys Lys Asp Leu Phe Leu
385                 390                 395                 400

Asp Leu Met Gly Asp Val Val Phe Gly Val Pro Ser Val Thr Val Ala
                405                 410                 415

Arg Gln His Arg Asp Ala Gly Ala Pro Thr Tyr Met Tyr Glu Phe Gln
                420                 425                 430

Tyr Arg Pro Ser Phe Ser Ser Asp Lys Lys Pro Lys Thr Val Ile Gly
                435                 440                 445

Asp His Gly Asp Glu Ile Phe Ser Val Phe Gly Phe Pro Leu Leu Lys
                450                 455                 460

Gly Asp Ala Pro Glu Glu Glu Val Ser Leu Ser Lys Thr Val Met Lys
465                 470                 475                 480

Phe Trp Ala Asn Phe Ala Arg Ser Gly Asn Pro Asn Gly Glu Gly Leu
                485                 490                 495

Pro His Trp Pro Met Tyr Asp Gln Glu Glu Gly Tyr Leu Gln Ile Gly
                500                 505                 510

Val Asn Thr Gln Ala Ala Lys Arg Leu Lys Gly Glu Glu Val Ala Phe
                515                 520                 525

Trp Asn Asp Leu Leu Ser Lys Glu Ala Ala Lys Lys Pro Pro Lys Ile
                530                 535                 540

Lys His Ala Glu Leu
545

<210> SEQ ID NO 13
<211> LENGTH: 1650
<212> TYPE: DNA
<213> ORGANISM: artificial sequence
<220> FEATURE:
<223> OTHER INFORMATION: protein with esterase activity

<400> SEQUENCE: 13
atgggacaac cagcttcgcc gcctgtcgtt gacaccgctc aaggtcgtgt cttgggtaag    60
tacgtctctc ttgagggttt ggcacaacct gttgctgtct tcttgggtgt cccttttcgct   120
```

| | |
|---|---|
| aagcctccac ttggatcttt gcgtttcgcc cctcctcaac cagcagagcc atggtctttc | 180 |
| gttaagaaca ctacttccta ccctccaatg tgttgtcaag aaccaattgg aggtcaaatg | 240 |
| ctttccgatc ttttcactaa cagaaaggaa cgtcttattc ctgagttctc tgaggactgc | 300 |
| ctttacctta acatctacac tcctgccgac ttgaccaaga gaggtagatt gcctgttatg | 360 |
| gtttggatcc acggaggtgg tttggttgtt ggtggagcat ccacttacga tggattggct | 420 |
| cttgccgcac acgagaacgt tgttgttgtt gctatccaat acagattggg tatctgggga | 480 |
| ttcttctcca ccggtgacga acactcccgt ggtaactggg acaccttga ccaagttgct | 540 |
| gcattgcatt gggtccaaga aaacatcgct aacttcggag gtgacccagg ttctgttact | 600 |
| atcttcggtg aaagtgcagg aggtgagagt gtctctgtct tggttttatc cccacttgct | 660 |
| aagaaccttt ccaccgtgc tatctccgaa tccggtgttg ctttcaccgc cggtttggtc | 720 |
| agaaaggaca tgaaggccgc agccaagcag attgccgtcc ttgccggatg caagactact | 780 |
| actagtgccg tcttcgtcca ctgtttgaga caaaagagtg aagacgaact tttggacctc | 840 |
| acattgaaga tgaagttttt cgcccttgac cttcacggaa cccaagaga atctcaccca | 900 |
| ttcttgacca ctgttgttga cggagttttg ttgccaaaga tgcctgagga aattttggcc | 960 |
| gagaaggact tcaacaccgt cccatacatc gttggaatca caagcagga gttcggttgg | 1020 |
| cttttgccaa caatgatggg tttcccactt tccgaaggta agttggacca aaagacagct | 1080 |
| acatcccttt tgtggaagtc ctacccaatc gccaacatcc ctgaagagtt gaccccagtt | 1140 |
| gctaccgaca agtaccttgg tggtaccgac gacccagtca aaagaagga cttgttcttg | 1200 |
| gaccttatgg gtgatgttgt tttcggtgtc ccatctgtta cagttgctcg tcagcacaga | 1260 |
| gatgcaggag ctccaactta catgtacgag ttccaataca gaccatcttt ctcaagtgac | 1320 |
| aagaagccaa agaccgttat cggagaccac ggtgacgaaa tcttctccgt cttcggattc | 1380 |
| ccattgctta agggtgacgc tccagaggaa gaagtctccc tttctaagac cgttatgaag | 1440 |
| ttctgggcta acttcgcccg ttctggtaac ccaaacggag aaggtttgcc acactggcct | 1500 |
| atgtacgacc aagaggaggg ataccttcaa atcggtgtca acactcaagc cgctaagcgt | 1560 |
| ttgaagggtg aggaagttgc tttctggaac gaccttttgt ccaaggaagc agcaaagaag | 1620 |
| cctccaaaga ttaagcacgc tgaattgtaa | 1650 |

<210> SEQ ID NO 14
<211> LENGTH: 1650
<212> TYPE: DNA
<213> ORGANISM: artificial sequence
<220> FEATURE:
<223> OTHER INFORMATION: protein with esterase activity

<400> SEQUENCE: 14

| | |
|---|---|
| atgggccaac ctgcttctcc acctgttgtt gacaccgctc aaggtcgtgt cttgggtaag | 60 |
| tacgtttctt tggaaggttt ggctcaacct gttgctgtct tcttgggtgt tccatttgcc | 120 |
| aagccaccat taggttcttt aagatttgct ccaccacagc ctgctgaacc atggtctttc | 180 |
| gtcaagaaca ctacttctta ccctccaatg tgttgtcagg aaccaatcgg tggtcaaatg | 240 |
| ctttccgatt tattcaccaa cagaaaggaa agattgattc cagagttcag tgaggactgt | 300 |
| ctatatttga acatttacac tccagctgat ttgaccaaga gaggtcgtct gcccgtcatg | 360 |
| gtttggattc acggtggtgg tttggttgtc ggtggtgctt ccacttacga tggtttggct | 420 |
| ttggctgctc acgagaatgt tgttgttgtt gccattcaat acagattagg tatctggggt | 480 |
| ttcttctcca ccggtgacga acactccaga ggtaactggg gtcatttgga ccaagttgct | 540 |

```
gctttgcact gggttcaaga aaacattgcc aacttcggtg gtgacccagg ttccgtcact    600
atctttggtg aatctgctgg tggtgaatcc gtctccgtct tggtcttgtc tccattggcc    660
aagaacttat ccatcgtgc catctctgaa tccggtgttg ccttcaccgc tggtttagtg    720
agaaaggaca tgaaggctgc tgccaagcaa attgctgtct ggctggttg taagaccacc    780 acctctgctg tctttgtcca ttgtttgaga caaaagtctg aagatgagct actagatttg    840
actttgaaaa tgaaattctt tgctttggat ttgcacggtg acccaagaga atctcatcct    900
ttcttgacca ccgttgttga tggtgtcttg ttgccaaaga tgccagaaga aatcttggct    960
gaaaaggatt tcaacactgt tccatacatt gtcggtatta caagcaaga gtttggctgg   1020 ttactaccaa ccatgatggg tttcccatta tctgaaggta aactggacca aaagactgcc   1080
acttcgctgc tatggaaatc ttacccaatt gccaacattc agaagaatt gactccagtt   1140 gccactgaca agtacttggg tggtactgat gatcctgtca agaagaagga cttgttcttg   1200
gatttgatgg gtgatgttgt tttcggtgtt ccatctgtca ccgttgccag acaacaccgt   1260
gatgctggtg ctccaactta catgtatgag ttccaataca gaccttcctt ctcctctgac   1320
aagaagccaa agactgtcat cggtgaccac ggtgatgaaa tcttctccgt ctttggtttc   1380
ccattattga agggtgacgc tccagaagaa gaagtttctt tatccaagac cgtcatgaaa   1440
ttctgggcca actttgccag atccggtaac ccaaatggtg aaggtttacc tcactggcca   1500
atgtatgacc aagaagaagg ttacttgcaa atcggtgtca acactcaagc tgccaagaga   1560 ttgaaggggtg aagaagttgc tttctggaat gacttgttgt ccaaggaagc tgccaagaag   1620
ccaccaaaga tcaagcatgc tgaattgtaa                                   1650

<210> SEQ ID NO 15
<211> LENGTH: 1650
<212> TYPE: DNA
<213> ORGANISM: artificial sequence
<220> FEATURE:
<223> OTHER INFORMATION: primer

<400> SEQUENCE: 15
atggggcagc cagcctcgcc gcctgttgtg gacactgccc agggccgtgt cctggggaag     60
tacgtcagct tagaaggcct ggcacagccg gtggccgtct tcctgggagt ccctttttgcc    120 aagccccctc tcggatcttt gcgttttgct ccgccgcagc ctgcagaacc atggagcttc    180
gtgaagaaca ccacctccta ccctcccatg tgctgccaag agccaattgg gggacagatg    240
ctctctgatc tgtttaccaa ccgtaaggag cgtctcattc cggagttttc tgaagactgt    300
ctctacctga atatttacac ccctgctgac ctgacaaagc gtggccgtct gccggtgatg    360
gtgtggattc acgaggagg tctggtggtg ggcggggctt ccacctatga tggactggcc    420
ctcgctgcgc atgaaaacgt ggtggtggtg gccatccagt accgcctggg catctgggga    480
ttcttcagca caggggacga acacagccgg ggcaactggg gtcacttgga ccaggtggcc    540
gcactgcact gggtccagga gaacatcgcc aactttggag gcgacccagg ctctgtgacc    600
atctttggag agtcagcagg aggggaaagt gtctctgttc tggtgttgtc tcccttggcc    660
aagaacctct ccaccgggc catctctgag agtggcgtgg ccttcactgc tggcctggtc    720
cgtaaggaca tgaaggctgc agctaagcaa attgctgtcc ttgctgggtg taaaaccacc    780
acctcggctg tctttgttca ctgcctgcgc cagaagtcgg aggacgagct cttggactta    840
acgctgaaga tgaatttttt cgctcttgat ttgcatggag accccgtgaa gagccatccc    900
```

```
ttcctgacca ctgtggtgga tggagtgctg ctgcccaaga tgcctgaaga gattctggct    960
gaaaaggatt tcaacactgt cccctacatc gtgggaatca acaagcaaga gtttggctgg   1020
cttctgccaa cgatgatggg cttcccctc tctgaaggca agctggacca aagacggcc    1080 acgtcactcc tgtggaagtc ctaccccatc gctaacatcc ctgaggaact gactccagtg   1140
gccactgaca agtatttggg ggggacagac gaccccgtca aaagaaaga cctgttcctg    1200 gacttgatgg gggatgtggt gtttggtgtc ccatctgtga cggtggcccg tcaacaccgc    1260
gatgcaggag cccccaccta catgtatgag tttcagtatc gcccgagctt ctcatcggac    1320
aagaaaccca agacggtgat cggggaccac ggggatgaaa tcttctccgt ctttggtttt    1380
ccactgttaa aaggcgatgc cccagaagag gaggtcagtc tcagcaagac ggtgatgaaa    1440
ttctgggcca ctttgctcg cagtgggaac cccaatgggg aggggctgcc ccattggccg    1500
atgtacgacc aggaagaagg gtaccttcag atcggcgtca cacccaggc agccaagcgc    1560 ctgaaaggtg aagaagtggc cttctggaac gatctcctgt ccaaggaggc agcaaagaag    1620
ccacccaaga taaagcatgc tgagctgtga                                    1650

<210> SEQ ID NO 16
<211> LENGTH: 44
<212> TYPE: DNA
<213> ORGANISM: artificial sequence
<220> FEATURE:
<223> OTHER INFORMATION: primer

<400> SEQUENCE: 16
ctttaagaag gagatataca tatgggacaa ccagcttcgc cgcc                      44

<210> SEQ ID NO 17
<211> LENGTH: 46
<212> TYPE: DNA
<213> ORGANISM: artificial sequence
<220> FEATURE:
<223> OTHER INFORMATION: primer

<400> SEQUENCE: 17
cccccccccc ccaagcttat tacaattcgg cgtgctttat cttagg                    46

<210> SEQ ID NO 18
<211> LENGTH: 38
<212> TYPE: DNA
<213> ORGANISM: artificial sequence
<220> FEATURE:
<223> OTHER INFORMATION: primer

<400> SEQUENCE: 18
atttatacat atgggacaac cagcttcgcc gcctgtcg                             38

<210> SEQ ID NO 19
<211> LENGTH: 43
<212> TYPE: DNA
<213> ORGANISM: artificial sequence
<220> FEATURE:
<223> OTHER INFORMATION: primer

<400> SEQUENCE: 19
ccgccaagct tattacaatt cagcgtgctt aatctttgga ggc                       43

<210> SEQ ID NO 20
<211> LENGTH: 38
<212> TYPE: DNA
<213> ORGANISM: artificial sequence
```

```
<220> FEATURE:
<223> OTHER INFORMATION: primer

<400> SEQUENCE: 20
atttatacat atgggccaac ctgcttctcc acctgttg                           38

<210> SEQ ID NO 21
<211> LENGTH: 43
<212> TYPE: DNA
<213> ORGANISM: artificial sequence
<220> FEATURE:
<223> OTHER INFORMATION: primer

<400> SEQUENCE: 21
ccgccaagct tattacaatt cagcatgctt gatctttggt ggc                     43

<210> SEQ ID NO 22
<211> LENGTH: 38
<212> TYPE: DNA
<213> ORGANISM: artificial sequence
<220> FEATURE:
<223> OTHER INFORMATION: primer

<400> SEQUENCE: 22
atttatacat atgggacaac cagcttcgcc gcctgtcg                           38

<210> SEQ ID NO 23
<211> LENGTH: 43
<212> TYPE: DNA
<213> ORGANISM: artificial sequence
<220> FEATURE:
<223> OTHER INFORMATION: primer

<400> SEQUENCE: 23
ccgccaagct tattacaatt cggcgtgctt tatcttaggt ggc                     43

<210> SEQ ID NO 24
<211> LENGTH: 35
<212> TYPE: DNA
<213> ORGANISM: artificial sequence
<220> FEATURE:
<223> OTHER INFORMATION: primer

<400> SEQUENCE: 24
atttatacat atggggcagc cagcctcgcc gcctg                              35

<210> SEQ ID NO 25
<211> LENGTH: 42
<212> TYPE: DNA
<213> ORGANISM: artificial sequence
<220> FEATURE:
<223> OTHER INFORMATION: primer

<400> SEQUENCE: 25
ccgccaagct tatcacagct cagcatgctt tatcttgggt gg                      42

<210> SEQ ID NO 26
<211> LENGTH: 57
<212> TYPE: DNA
<213> ORGANISM: artificial sequence
<220> FEATURE:
<223> OTHER INFORMATION: primer

<400> SEQUENCE: 26
cggatccttt aactttaaga aggagatata atggatgacg cggcaattca acaaacg      57
```

-continued

```
<210> SEQ ID NO 27
<211> LENGTH: 38
<212> TYPE: DNA
<213> ORGANISM: artificial sequence
<220> FEATURE:
<223> OTHER INFORMATION: primer

<400> SEQUENCE: 27
cggatcctta tttaccgctg gtcatttttt ggtgttcg                              38

<210> SEQ ID NO 28
<211> LENGTH: 71
<212> TYPE: DNA
<213> ORGANISM: artificial sequence
<220> FEATURE:
<223> OTHER INFORMATION: primer

<400> SEQUENCE: 28
gtaaattccc tacaatcctg cccattgtct gccaacaact atgggatct tgtgtaggct       60 ggagctgctt c                                                          71

<210> SEQ ID NO 29
<211> LENGTH: 71
<212> TYPE: DNA
<213> ORGANISM: artificial sequence
<220> FEATURE:
<223> OTHER INFORMATION: primer

<400> SEQUENCE: 29
cccatagtcg catggtgtcg ccttctttac ttttgttact gatttgtaaa acatatgaat      60
atcctcctta g                                                          71

<210> SEQ ID NO 30
<211> LENGTH: 74
<212> TYPE: DNA
<213> ORGANISM: artificial sequence
<220> FEATURE:
<223> OTHER INFORMATION: primer

<400> SEQUENCE: 30
cctattacgt ctcgcgctac aatcgcggta atcaacgata aggacacttt gtctgtgtag      60
gctggagctg cttc                                                       74

<210> SEQ ID NO 31
<211> LENGTH: 75
<212> TYPE: DNA
<213> ORGANISM: artificial sequence
<220> FEATURE:
<223> OTHER INFORMATION: primer

<400> SEQUENCE: 31
ctgatagcgg aaacgtaatt aagggctaag agcacactac tcttagcccc ttaaccatat      60
gaatatcctc cttag                                                      75

<210> SEQ ID NO 32
<211> LENGTH: 1629
<212> TYPE: DNA
<213> ORGANISM: artificial sequence
<220> FEATURE:
<223> OTHER INFORMATION: protein with esterase activity
<220> FEATURE:
<221> NAME/KEY: CDS
<222> LOCATION: (1)..(1629)
<223> OTHER INFORMATION: Bovine Liver Esterase
```

<400> SEQUENCE: 32

```
atg ggt ctg gca ccg tcg cca cct atc gtg gat acc gca cag ggc cgt      48
Met Gly Leu Ala Pro Ser Pro Pro Ile Val Asp Thr Ala Gln Gly Arg
1               5                   10                  15 gtt ctg ggg aag cac gtc agc cta aaa ggt ttc gca cag ccg gtg gcg      96
Val Leu Gly Lys His Val Ser Leu Lys Gly Phe Ala Gln Pro Val Ala
            20                  25                  30 gtt ttt ctg ggt gtc cca ttc gcc aaa ccg cct tta ggg tcc ttg cgt     144
Val Phe Leu Gly Val Pro Phe Ala Lys Pro Pro Leu Gly Ser Leu Arg
        35                  40                  45 ttc gcc cca cct cag ccg gct gag ccg tgg acc ttt gtc aag aat acc     192
Phe Ala Pro Pro Gln Pro Ala Glu Pro Trp Thr Phe Val Lys Asn Thr
50                  55                  60 att agc tat cca ccg atg tgc tcc caa gat cca gtg ggt gct cag ttg     240
Ile Ser Tyr Pro Pro Met Cys Ser Gln Asp Pro Val Gly Ala Gln Leu
65                  70                  75                  80 tta tcg gac ctg ttc acc aac cgc aaa gaa aac atc agt ctg act ttc     288
Leu Ser Asp Leu Phe Thr Asn Arg Lys Glu Asn Ile Ser Leu Thr Phe
                85                  90                  95 agc gag gat tgc ttg tat ctc aat atc tat acc ccg gca gat tta act     336
Ser Glu Asp Cys Leu Tyr Leu Asn Ile Tyr Thr Pro Ala Asp Leu Thr
            100                 105                 110 aaa cgt agc cgc ctg ccg gtg atg gtg tgg att cat ggt ggt gga ctg     384
Lys Arg Ser Arg Leu Pro Val Met Val Trp Ile His Gly Gly Gly Leu
        115                 120                 125 atg gtg ggc ggc gct tct acg tac gac ggg ctg gtc tta tcg gcg cac     432
Met Val Gly Gly Ala Ser Thr Tyr Asp Gly Leu Val Leu Ser Ala His
130                 135                 140 gag aac gtg gtg gtg gtg acc atc cag tat cgt ctg ggc att tgg ggt     480
Glu Asn Val Val Val Val Thr Ile Gln Tyr Arg Leu Gly Ile Trp Gly
145                 150                 155                 160 ttc ttt agc acg ggc gat gaa cat agt cgc ggg aac tgg ggc cat ttg     528
Phe Phe Ser Thr Gly Asp Glu His Ser Arg Gly Asn Trp Gly His Leu
                165                 170                 175 gat cag gtg gcg gct ctg cat tgg gtc cag gaa aac atc gcg aac ttc     576
Asp Gln Val Ala Ala Leu His Trp Val Gln Glu Asn Ile Ala Asn Phe
            180                 185                 190 ggt ggc gac cca ggc agc gtg acc atc ttt ggt gaa tcc gcc ggt gca     624
Gly Gly Asp Pro Gly Ser Val Thr Ile Phe Gly Glu Ser Ala Gly Ala
        195                 200                 205 gag agt gtt agc atc tta gtg ctt tcc ccg ctg gcg cgt aat ttg ttt     672
Glu Ser Val Ser Ile Leu Val Leu Ser Pro Leu Ala Arg Asn Leu Phe
210                 215                 220 cat cgc gcg att agc gaa agc ggc gtg gcg ctg atc tcg acc ctg gtt     720
His Arg Ala Ile Ser Glu Ser Gly Val Ala Leu Ile Ser Thr Leu Val
225                 230                 235                 240 aaa cgt gat tca aaa gcc gca gct gag caa atc gcc gtc atc gca ggc     768
Lys Arg Asp Ser Lys Ala Ala Ala Glu Gln Ile Ala Val Ile Ala Gly
                245                 250                 255 tgt aag acc acc acc tct gcc gtc tta gta cat tgc ctg cgc cag aaa     816
Cys Lys Thr Thr Thr Ser Ala Val Leu Val His Cys Leu Arg Gln Lys
            260                 265                 270 acg gaa gat gaa ttg ctg gaa atc acg ctg aag atg aaa ttc ttt gca     864
Thr Glu Asp Glu Leu Leu Glu Ile Thr Leu Lys Met Lys Phe Phe Ala
        275                 280                 285 ctc gac ctt cat aag gat agt acg gaa agc cac ccg ttt ctg ccg acc     912
Leu Asp Leu His Lys Asp Ser Thr Glu Ser His Pro Phe Leu Pro Thr
290                 295                 300
```

```
gtg gtt gac ggc atg ctg ctg cct aaa atg ccg gaa gag atg ctg gcc    960
Val Val Asp Gly Met Leu Leu Pro Lys Met Pro Glu Glu Met Leu Ala
305                 310                 315                 320 gag aaa aat ttt aac aac gtc ccg tat atg gtg ggt att aac aaa caa   1008
Glu Lys Asn Phe Asn Asn Val Pro Tyr Met Val Gly Ile Asn Lys Gln
            325                 330                 335 gaa ttc ggc tgg atc atc cca ctg ttt atg agc tat ccg ctg ccg gag   1056
Glu Phe Gly Trp Ile Ile Pro Leu Phe Met Ser Tyr Pro Leu Pro Glu
        340                 345                 350 gat aaa ctg gat cag aaa act gcg acg agt ctg ctg tgg cag agc tat   1104
Asp Lys Leu Asp Gln Lys Thr Ala Thr Ser Leu Leu Trp Gln Ser Tyr
    355                 360                 365 tcc tta ttg agc atc cca gaa gaa ctg tcg ccg gtg gcc acg gat aaa   1152
Ser Leu Leu Ser Ile Pro Glu Glu Leu Ser Pro Val Ala Thr Asp Lys
370                 375                 380 tac cta ggt ggg act gat gat cct gtt aaa aag aaa gat ctg ttt ctg   1200
Tyr Leu Gly Gly Thr Asp Asp Pro Val Lys Lys Lys Asp Leu Phe Leu
385                 390                 395                 400 gat ctg atc gct gac gtt ctc ttc ggc gtc ccg tct gtc aat gtg gcg   1248
Asp Leu Ile Ala Asp Val Leu Phe Gly Val Pro Ser Val Asn Val Ala
                405                 410                 415 cgg cgc cat cgt gac gct ggg gcg ccg acc tat atg tac gaa ttc cag   1296
Arg Arg His Arg Asp Ala Gly Ala Pro Thr Tyr Met Tyr Glu Phe Gln
            420                 425                 430 tac cgc ccg agc ttt agt tca gaa ctg aag ccg aaa act gtg atc ggt   1344
Tyr Arg Pro Ser Phe Ser Ser Glu Leu Lys Pro Lys Thr Val Ile Gly
        435                 440                 445 gat cac ggt gac gaa ctg ttt tcc gtc ttt ggg gca cca ttc cta aag   1392
Asp His Gly Asp Glu Leu Phe Ser Val Phe Gly Ala Pro Phe Leu Lys
    450                 455                 460 gac ggt gcg tcg gaa gag gaa att aat ctg agc aaa atg gtg atg aag   1440
Asp Gly Ala Ser Glu Glu Glu Ile Asn Leu Ser Lys Met Val Met Lys
465                 470                 475                 480 ttt tgg gcg aac ttc gca cgc aat ggg aac ccg aat ggt gaa ggc tta   1488
Phe Trp Ala Asn Phe Ala Arg Asn Gly Asn Pro Asn Gly Glu Gly Leu
                485                 490                 495 cct cac tgg cca gct tac gat cat aaa gag ggc tat ttg cag atc ggt   1536
Pro His Trp Pro Ala Tyr Asp His Lys Glu Gly Tyr Leu Gln Ile Gly
            500                 505                 510 gtt aac acg cgt gcg gcc gag aaa ctg aag gat aaa gag gta gca ttt   1584
Val Asn Thr Arg Ala Ala Glu Lys Leu Lys Asp Lys Glu Val Ala Phe
        515                 520                 525 tgg aat gaa ctg ctg agc cgc gaa gtg gca cgt cat cat acc taa       1629
Trp Asn Glu Leu Leu Ser Arg Glu Val Ala Arg His His Thr
    530                 535                 540
```

<210> SEQ ID NO 33
<211> LENGTH: 542
<212> TYPE: PRT
<213> ORGANISM: artificial sequence
<220> FEATURE:
<223> OTHER INFORMATION: Synthetic Construct

<400> SEQUENCE: 33

```
Met Gly Leu Ala Pro Ser Pro Pro Ile Val Asp Thr Ala Gln Gly Arg
1               5                   10                  15

Val Leu Gly Lys His Val Ser Leu Lys Gly Phe Ala Gln Pro Val Ala
            20                  25                  30

Val Phe Leu Gly Val Pro Phe Ala Lys Pro Pro Leu Gly Ser Leu Arg
        35                  40                  45
```

-continued

```
Phe Ala Pro Pro Gln Pro Ala Glu Pro Trp Thr Phe Val Lys Asn Thr
 50              55                  60
Ile Ser Tyr Pro Pro Met Cys Ser Gln Asp Pro Val Gly Ala Gln Leu
 65              70                  75                  80
Leu Ser Asp Leu Phe Thr Asn Arg Lys Glu Asn Ile Ser Leu Thr Phe
                 85                  90                  95
Ser Glu Asp Cys Leu Tyr Leu Asn Ile Tyr Thr Pro Ala Asp Leu Thr
                100                 105                 110
Lys Arg Ser Arg Leu Pro Val Met Val Trp Ile His Gly Gly Gly Leu
                115                 120                 125
Met Val Gly Gly Ala Ser Thr Tyr Asp Gly Leu Val Leu Ser Ala His
130                 135                 140
Glu Asn Val Val Val Thr Ile Gln Tyr Arg Leu Gly Ile Trp Gly
145                 150                 155                 160
Phe Phe Ser Thr Gly Asp Glu His Ser Arg Gly Asn Trp Gly His Leu
                165                 170                 175
Asp Gln Val Ala Ala Leu His Trp Val Gln Glu Asn Ile Ala Asn Phe
                180                 185                 190
Gly Gly Asp Pro Gly Ser Val Thr Ile Phe Gly Glu Ser Ala Gly Ala
                195                 200                 205
Glu Ser Val Ser Ile Leu Val Leu Ser Pro Leu Ala Arg Asn Leu Phe
210                 215                 220
His Arg Ala Ile Ser Glu Ser Gly Val Ala Leu Ile Ser Thr Leu Val
225                 230                 235                 240
Lys Arg Asp Ser Lys Ala Ala Glu Gln Ile Ala Val Ile Ala Gly
                245                 250                 255
Cys Lys Thr Thr Thr Ser Ala Val Leu Val His Cys Leu Arg Gln Lys
                260                 265                 270
Thr Glu Asp Glu Leu Leu Glu Ile Thr Leu Lys Met Lys Phe Phe Ala
                275                 280                 285
Leu Asp Leu His Lys Asp Ser Thr Glu Ser His Pro Phe Leu Pro Thr
                290                 295                 300
Val Val Asp Gly Met Leu Leu Pro Lys Met Pro Glu Glu Met Leu Ala
305                 310                 315                 320
Glu Lys Asn Phe Asn Asn Val Pro Tyr Met Val Gly Ile Asn Lys Gln
                325                 330                 335
Glu Phe Gly Trp Ile Ile Pro Leu Phe Met Ser Tyr Pro Leu Pro Glu
                340                 345                 350
Asp Lys Leu Asp Gln Lys Thr Ala Thr Ser Leu Leu Trp Gln Ser Tyr
                355                 360                 365
Ser Leu Leu Ser Ile Pro Glu Glu Leu Ser Pro Val Ala Thr Asp Lys
                370                 375                 380
Tyr Leu Gly Gly Thr Asp Asp Pro Val Lys Lys Lys Asp Leu Phe Leu
385                 390                 395                 400
Asp Leu Ile Ala Asp Val Leu Phe Gly Val Pro Ser Val Asn Val Ala
                405                 410                 415
Arg Arg His Arg Asp Ala Gly Ala Pro Thr Tyr Met Tyr Glu Phe Gln
                420                 425                 430
Tyr Arg Pro Ser Phe Ser Ser Glu Leu Lys Pro Lys Thr Val Ile Gly
                435                 440                 445
Asp His Gly Asp Glu Leu Phe Ser Val Phe Gly Ala Pro Phe Leu Lys
450                 455                 460
Asp Gly Ala Ser Glu Glu Glu Ile Asn Leu Ser Lys Met Val Met Lys
```

```
                465                 470                 475                 480
        Phe Trp Ala Asn Phe Ala Arg Asn Gly Asn Pro Asn Gly Glu Gly Leu
                            485                 490                 495

Pro His Trp Pro Ala Tyr Asp His Lys Glu Gly Tyr Leu Gln Ile Gly
                    500                 505                 510

Val Asn Thr Arg Ala Ala Glu Lys Leu Lys Asp Lys Glu Val Ala Phe
                    515                 520                 525

Trp Asn Glu Leu Leu Ser Arg Glu Val Ala Arg His His Thr
                    530                 535                 540

<210> SEQ ID NO 34
<211> LENGTH: 1650
<212> TYPE: DNA
<213> ORGANISM: artificial sequence
<220> FEATURE:
<223> OTHER INFORMATION: protein with esterase activity
<220> FEATURE:
<221> NAME/KEY: CDS
<222> LOCATION: (1)..(1650)

<400> SEQUENCE: 34 atg gga caa cca gct tcg ccg cct gtc gtt gat acc gct caa gga cga       48
Met Gly Gln Pro Ala Ser Pro Pro Val Val Asp Thr Ala Gln Gly Arg
1               5                   10                  15 gtc ttg ggt aag tac gtc tct tta gag gga ttg gca caa ccg gtt gct       96
Val Leu Gly Lys Tyr Val Ser Leu Glu Gly Leu Ala Gln Pro Val Ala
                20                  25                  30 gtc ttc ttg gga gtc cct ttt gct aag cca cct ctt gga tct ttg agg      144
Val Phe Leu Gly Val Pro Phe Ala Lys Pro Pro Leu Gly Ser Leu Arg
            35                  40                  45 ttt gcc ccg ccg caa cca gca gag cca tgg tct ttc gtt aag aac act      192
Phe Ala Pro Pro Gln Pro Ala Glu Pro Trp Ser Phe Val Lys Asn Thr
        50                  55                  60 act tcc tac cct cca atg tgt tgt caa gat cca gtc gta gaa caa atg      240
Thr Ser Tyr Pro Pro Met Cys Cys Gln Asp Pro Val Val Glu Gln Met
65                  70                  75                  80 acg tca gac cta ttc act aac gga aag gaa agg ctt acc ctg gag ttc      288
Thr Ser Asp Leu Phe Thr Asn Gly Lys Glu Arg Leu Thr Leu Glu Phe
                85                  90                  95 tct gag gat tgc ctt tac cta aat att tac act cct gcc gat ttg aca      336
Ser Glu Asp Cys Leu Tyr Leu Asn Ile Tyr Thr Pro Ala Asp Leu Thr
            100                 105                 110 aag agg ggt agg ttg ccg gtt atg gtt tgg att cat gga gga ggt ttg      384
Lys Arg Gly Arg Leu Pro Val Met Val Trp Ile His Gly Gly Gly Leu
        115                 120                 125 gtt ctg ggc gga gca ccg atg tat gac gga gtg gtt ctt gcc gcg cac      432
Val Leu Gly Gly Ala Pro Met Tyr Asp Gly Val Val Leu Ala Ala His
    130                 135                 140 gag aac gtt gtt gtt gtt gct att caa tac cgt ttg ggt att tgg gga      480
Glu Asn Val Val Val Val Ala Ile Gln Tyr Arg Leu Gly Ile Trp Gly
145                 150                 155                 160 ttt ttc tcc aca gga gat gag cat tcc cgt gga aac tgg ggc cat tta      528
Phe Phe Ser Thr Gly Asp Glu His Ser Arg Gly Asn Trp Gly His Leu
                165                 170                 175 gat caa gtt gct gca ttg cat tgg gtc caa gaa aac att gct aac ttc      576
Asp Gln Val Ala Ala Leu His Trp Val Gln Glu Asn Ile Ala Asn Phe
            180                 185                 190 gga ggt gat cca ggt tct gtt act att ttc gga gaa tca gca ggc gga      624
Gly Gly Asp Pro Gly Ser Val Thr Ile Phe Gly Glu Ser Ala Gly Gly
        195                 200                 205
```

```
gag agt gtc tct gta ttg gtt tta tca cca tta gct aag aac ctt ttt        672
Glu Ser Val Ser Val Leu Val Leu Ser Pro Leu Ala Lys Asn Leu Phe
    210             215             220 cat cgt gct att tcc gaa agt ggt gtt gct tta acc gtc gct ttg gtc        720
His Arg Ala Ile Ser Glu Ser Gly Val Ala Leu Thr Val Ala Leu Val
225             230             235             240 agg aag gat atg aag gcc gca gcc aag cag atc gct gtc ctt gca gga        768
Arg Lys Asp Met Lys Ala Ala Ala Lys Gln Ile Ala Val Leu Ala Gly
                245             250             255 tgc aaa act act act tcg gca gtc ttc gtg cat tgt ttg cgt caa aag        816
Cys Lys Thr Thr Thr Ser Ala Val Phe Val His Cys Leu Arg Gln Lys
            260             265             270 tcg gaa gat gaa ctt tta gac ctc acg ttg aag atg aaa ttc ctg acc        864
Ser Glu Asp Glu Leu Leu Asp Leu Thr Leu Lys Met Lys Phe Leu Thr
        275             280             285 ctt gac ttt cac gga gat caa agg gaa tct cac cct ttt ttg ccg act        912
Leu Asp Phe His Gly Asp Gln Arg Glu Ser His Pro Phe Leu Pro Thr
    290             295             300 gtt gtt gac gga gtt ttg ttg cct aag atg cct gag gaa atc ttg gcc        960
Val Val Asp Gly Val Leu Leu Pro Lys Met Pro Glu Glu Ile Leu Ala
305             310             315             320 gag aag gac ttt aac acc gtc cca tac att gtt gga att aac aag cag       1008
Glu Lys Asp Phe Asn Thr Val Pro Tyr Ile Val Gly Ile Asn Lys Gln
                325             330             335 gag ttc gga tgg ctt ttg cca acg atg atg gga ttt cct ctt tcc gag       1056
Glu Phe Gly Trp Leu Leu Pro Thr Met Met Gly Phe Pro Leu Ser Glu
            340             345             350 gga aag ttg gat caa aag acg gct acg tca ctt ttg tgg aag tcc tac       1104
Gly Lys Leu Asp Gln Lys Thr Ala Thr Ser Leu Leu Trp Lys Ser Tyr
        355             360             365 cca att gcc aac att cct gaa gag ttg acc cca gtt gct acc gat aag       1152
Pro Ile Ala Asn Ile Pro Glu Glu Leu Thr Pro Val Ala Thr Asp Lys
    370             375             380 tat tta gga gga aca gat gat cct gtc aaa aag aaa gat ttg ttt ttg       1200
Tyr Leu Gly Gly Thr Asp Asp Pro Val Lys Lys Lys Asp Leu Phe Leu
385             390             395             400 gat ctg atg gga gac gtt gtt ttc ggc gtc cca tca gtt acg gtt gct       1248
Asp Leu Met Gly Asp Val Val Phe Gly Val Pro Ser Val Thr Val Ala
                405             410             415 cgt cag cat agg gac gca gga gct cca act tac atg tat gag ttc caa       1296
Arg Gln His Arg Asp Ala Gly Ala Pro Thr Tyr Met Tyr Glu Phe Gln
            420             425             430 tat cgt cca tct ttt tca tcg gat aag aaa cct aag acg gtt att gga       1344
Tyr Arg Pro Ser Phe Ser Ser Asp Lys Lys Pro Lys Thr Val Ile Gly
        435             440             445 gat cat gga gac gaa att ttt tcc gtc ttc ggc ttc cca ttg ctc aaa       1392
Asp His Gly Asp Glu Ile Phe Ser Val Phe Gly Phe Pro Leu Leu Lys
    450             455             460 ggt gac gct cca gag gaa gaa gtc agt ctt tct aag acg gtt atg aaa       1440
Gly Asp Ala Pro Glu Glu Glu Val Ser Leu Ser Lys Thr Val Met Lys
465             470             475             480 ttt tgg gct aac ttc gcc cgt agt gga aac cct aat gga gaa gga ttg       1488
Phe Trp Ala Asn Phe Ala Arg Ser Gly Asn Pro Asn Gly Glu Gly Leu
                485             490             495 cct cac tgg ccg atg tac gat caa gag gag gga tac ctt caa att ggt       1536
Pro His Trp Pro Met Tyr Asp Gln Glu Glu Gly Tyr Leu Gln Ile Gly
            500             505             510 gtc aac act caa gca gct aag agg ttg aaa ggc gag gag gtt gct ttt       1584
Val Asn Thr Gln Ala Ala Lys Arg Leu Lys Gly Glu Glu Val Ala Phe
        515             520             525
```

```
tgg aac gac ctg ttg tcc aag gaa gca gca aag aag cca cct aag ata   1632
Trp Asn Asp Leu Leu Ser Lys Glu Ala Ala Lys Lys Pro Pro Lys Ile
    530                 535                 540 aag cac gcc gaa ttg taa                                           1650
Lys His Ala Glu Leu
545

<210> SEQ ID NO 35
<211> LENGTH: 549
<212> TYPE: PRT
<213> ORGANISM: artificial sequence
<220> FEATURE:
<223> OTHER INFORMATION: Synthetic Construct

<400> SEQUENCE: 35

Met Gly Gln Pro Ala Ser Pro Val Val Asp Thr Ala Gln Gly Arg
1               5                   10                  15

Val Leu Gly Lys Tyr Val Ser Leu Glu Gly Leu Ala Gln Pro Val Ala
                20                  25                  30

Val Phe Leu Gly Val Pro Phe Ala Lys Pro Pro Leu Gly Ser Leu Arg
            35                  40                  45

Phe Ala Pro Pro Gln Pro Ala Glu Pro Trp Ser Phe Val Lys Asn Thr
50                  55                  60

Thr Ser Tyr Pro Pro Met Cys Cys Gln Asp Pro Val Val Glu Gln Met
65                  70                  75                  80

Thr Ser Asp Leu Phe Thr Asn Gly Lys Glu Arg Leu Thr Leu Glu Phe
                85                  90                  95

Ser Glu Asp Cys Leu Tyr Leu Asn Ile Tyr Thr Pro Ala Asp Leu Thr
            100                 105                 110

Lys Arg Gly Arg Leu Pro Val Met Val Trp Ile His Gly Gly Gly Leu
        115                 120                 125

Val Leu Gly Gly Ala Pro Met Tyr Asp Gly Val Val Leu Ala Ala His
    130                 135                 140

Glu Asn Val Val Val Ala Ile Gln Tyr Arg Leu Gly Ile Trp Gly
145                 150                 155                 160

Phe Phe Ser Thr Gly Asp Glu His Ser Arg Gly Asn Trp Gly His Leu
                165                 170                 175

Asp Gln Val Ala Ala Leu His Trp Val Gln Glu Asn Ile Ala Asn Phe
            180                 185                 190

Gly Gly Asp Pro Gly Ser Val Thr Ile Phe Gly Glu Ser Ala Gly Gly
        195                 200                 205

Glu Ser Val Ser Val Leu Val Leu Ser Pro Leu Ala Lys Asn Leu Phe
    210                 215                 220

His Arg Ala Ile Ser Glu Ser Gly Val Ala Leu Thr Val Ala Leu Val
225                 230                 235                 240

Arg Lys Asp Met Lys Ala Ala Ala Lys Gln Ile Ala Val Leu Ala Gly
                245                 250                 255

Cys Lys Thr Thr Thr Ser Ala Val Phe Val His Cys Leu Arg Gln Lys
            260                 265                 270

Ser Glu Asp Glu Leu Leu Asp Leu Thr Leu Lys Met Lys Phe Leu Thr
        275                 280                 285

Leu Asp Phe His Gly Asp Gln Arg Glu Ser His Pro Phe Leu Pro Thr
    290                 295                 300

Val Val Asp Gly Val Leu Leu Pro Lys Met Pro Glu Glu Ile Leu Ala
305                 310                 315                 320
```

```
Glu Lys Asp Phe Asn Thr Val Pro Tyr Ile Val Gly Ile Asn Lys Gln
                325                 330                 335

Glu Phe Gly Trp Leu Leu Pro Thr Met Met Gly Phe Pro Leu Ser Glu
            340                 345                 350

Gly Lys Leu Asp Gln Lys Thr Ala Thr Ser Leu Leu Trp Lys Ser Tyr
        355                 360                 365

Pro Ile Ala Asn Ile Pro Glu Glu Leu Thr Pro Val Ala Thr Asp Lys
370                 375                 380

Tyr Leu Gly Gly Thr Asp Pro Val Lys Lys Asp Leu Phe Leu
385                 390                 395                 400

Asp Leu Met Gly Asp Val Val Phe Gly Val Pro Ser Val Thr Val Ala
                405                 410                 415

Arg Gln His Arg Asp Ala Gly Ala Pro Thr Tyr Met Tyr Glu Phe Gln
            420                 425                 430

Tyr Arg Pro Ser Phe Ser Ser Asp Lys Lys Pro Lys Thr Val Ile Gly
        435                 440                 445

Asp His Gly Asp Glu Ile Phe Ser Val Phe Gly Phe Pro Leu Leu Lys
    450                 455                 460

Gly Asp Ala Pro Glu Glu Glu Val Ser Leu Ser Lys Thr Val Met Lys
465                 470                 475                 480

Phe Trp Ala Asn Phe Ala Arg Ser Gly Asn Pro Asn Gly Glu Gly Leu
                485                 490                 495

Pro His Trp Pro Met Tyr Asp Gln Glu Gly Tyr Leu Gln Ile Gly
            500                 505                 510

Val Asn Thr Gln Ala Ala Lys Arg Leu Lys Gly Glu Val Ala Phe
        515                 520                 525

Trp Asn Asp Leu Leu Ser Lys Glu Ala Ala Lys Lys Pro Pro Lys Ile
530                 535                 540

Lys His Ala Glu Leu
545

<210> SEQ ID NO 36
<211> LENGTH: 1650
<212> TYPE: DNA
<213> ORGANISM: artificial sequence
<220> FEATURE:
<223> OTHER INFORMATION: protein with esterase activity
<220> FEATURE:
<221> NAME/KEY: CDS
<222> LOCATION: (1)..(1650)

<400> SEQUENCE: 36 atg gga caa cca gct tcg ccg cct gtc gtt gat acc gct caa gga cga      48
Met Gly Gln Pro Ala Ser Pro Pro Val Val Asp Thr Ala Gln Gly Arg
1               5                   10                  15 gtc ttg ggt aag tac gtc tct tta gag gga ttg gca caa ccg gtt gct      96
Val Leu Gly Lys Tyr Val Ser Leu Glu Gly Leu Ala Gln Pro Val Ala
            20                  25                  30 gtc ttc ttg gga gtc cct ttt gct aag cca cct ctt gga tct ttg agg     144
Val Phe Leu Gly Val Pro Phe Ala Lys Pro Pro Leu Gly Ser Leu Arg
        35                  40                  45 ttt gcc ccg ccg caa cca gca gag cca tgg tct ttc gtt aag aac act     192
Phe Ala Pro Pro Gln Pro Ala Glu Pro Trp Ser Phe Val Lys Asn Thr
    50                  55                  60 act tcc tac cct cca atg tgt tgt caa gat cca gtc gca gga caa atg     240
Thr Ser Tyr Pro Pro Met Cys Cys Gln Asp Pro Val Ala Gly Gln Met
65                  70                  75                  80 acg tca gac cta ttc act aac gga aag gaa agg ctt atc ccg gag ttc     288
```

```
            Thr Ser Asp Leu Phe Thr Asn Gly Lys Glu Arg Leu Ile Pro Glu Phe
                            85              90                  95 tct gag gat tgc ctt tac cta aat att tac act cct gcc gat ttg aca        336
Ser Glu Asp Cys Leu Tyr Leu Asn Ile Tyr Thr Pro Ala Asp Leu Thr
            100                 105                 110 aag agg ggt agg ttg ccg gtt atg gtt tgg att cat gga gga ggt ttg        384
Lys Arg Gly Arg Leu Pro Val Met Val Trp Ile His Gly Gly Gly Leu
            115                 120                 125 gtt gtt ggc gga gca tcc act tat gac gga ttg gct ctt gcc gcg cac        432
Val Val Gly Gly Ala Ser Thr Tyr Asp Gly Leu Ala Leu Ala Ala His
        130                 135                 140 gag aac gtt gtt gtt gtt gct att caa tac cgt ttg ggt att tgg gga        480
Glu Asn Val Val Val Val Ala Ile Gln Tyr Arg Leu Gly Ile Trp Gly
145                 150                 155                 160 ttt ttc tcc aca gga gat gag cat tcc cgt gga aac tgg ggc cat tta        528
Phe Phe Ser Thr Gly Asp Glu His Ser Arg Gly Asn Trp Gly His Leu
                165                 170                 175 gat caa gtt gct gca ttg cat tgg gtc caa gaa aac att gct aac ttc        576
Asp Gln Val Ala Ala Leu His Trp Val Gln Glu Asn Ile Ala Asn Phe
            180                 185                 190 gga ggt gat aca ggt tct gtt act att ttc gga gaa tca gca ggc gga        624
Gly Gly Asp Thr Gly Ser Val Thr Ile Phe Gly Glu Ser Ala Gly Gly
            195                 200                 205 gag agt gtc tct gta ttg gtt tta tca cca tta gct aag aac ctt ttt        672
Glu Ser Val Ser Val Leu Val Leu Ser Pro Leu Ala Lys Asn Leu Phe
210                 215                 220 cat cgt gct att tcc gaa agt ggt gtt gct tta acc gcc ggt ttg gtc        720
His Arg Ala Ile Ser Glu Ser Gly Val Ala Leu Thr Ala Gly Leu Val
225                 230                 235                 240 agg aag gat atg aag gcc gca gcc aag cag atc gct gtc ctt gca gga        768
Arg Lys Asp Met Lys Ala Ala Ala Lys Gln Ile Ala Val Leu Ala Gly
                245                 250                 255 tgc aaa act act act tcg gca gtc ttc gtg cat tgt ttg cgt caa aag        816
Cys Lys Thr Thr Thr Ser Ala Val Phe Val His Cys Leu Arg Gln Lys
            260                 265                 270 tcg gaa gat gaa ctt tta gac ctc acg ttg aag atg aaa ttc ctg acc        864
Ser Glu Asp Glu Leu Leu Asp Leu Thr Leu Lys Met Lys Phe Leu Thr
            275                 280                 285 ctt gac tta cac gga gat cca agg gaa tct cac cct ttt ttg ccg act        912
Leu Asp Leu His Gly Asp Pro Arg Glu Ser His Pro Phe Leu Pro Thr
        290                 295                 300 gtt gtt gac gga gtt ttg ttg cct aag atg cct gag gaa atc ttg gcc        960
Val Val Asp Gly Val Leu Leu Pro Lys Met Pro Glu Glu Ile Leu Ala
305                 310                 315                 320 gag aag gac ttt aac acc gtc cca tac att gtt gga att aac aag cag       1008
Glu Lys Asp Phe Asn Thr Val Pro Tyr Ile Val Gly Ile Asn Lys Gln
                325                 330                 335 gag ttc gga tgg ctt ttg cca acg atg atg gga ttt cct ctt tcc gag       1056
Glu Phe Gly Trp Leu Leu Pro Thr Met Met Gly Phe Pro Leu Ser Glu
            340                 345                 350 gga aag ttg gat caa aag acg gct acg tca ctt ttg tgg aag tcc ttc       1104
Gly Lys Leu Asp Gln Lys Thr Ala Thr Ser Leu Leu Trp Lys Ser Phe
            355                 360                 365 cca att acc aac att cct gaa gag ttg acc cca gtt gct acc gat aag       1152
Pro Ile Thr Asn Ile Pro Glu Glu Leu Thr Pro Val Ala Thr Asp Lys
        370                 375                 380 tat tta gga gga aca gat gat cct gtc aaa aag aaa gat ttg ttt ttg       1200
Tyr Leu Gly Gly Thr Asp Asp Pro Val Lys Lys Lys Asp Leu Phe Leu
385                 390                 395                 400
```

```
gat ctg atg gga gac gtt gtt ttc ggc gtc cca tca gtt acg gtt gct     1248
Asp Leu Met Gly Asp Val Val Phe Gly Val Pro Ser Val Thr Val Ala
            405                 410                 415 cgt cag cat agg gac gca gga gct cca act tac atg tat gag ttc caa     1296
Arg Gln His Arg Asp Ala Gly Ala Pro Thr Tyr Met Tyr Glu Phe Gln
        420                 425                 430 tat cgt cca tct ttt tca tcg gat aag aaa cct aag acg gtt att gga     1344
Tyr Arg Pro Ser Phe Ser Ser Asp Lys Lys Pro Lys Thr Val Ile Gly
    435                 440                 445 gat cat gga gac gaa att ttt tcc gtc ttc ggc ttc cca ttg ctc aaa     1392
Asp His Gly Asp Glu Ile Phe Ser Val Phe Gly Phe Pro Leu Leu Lys
450                 455                 460 ggt gac gct cca gag gaa gaa gtc agt ctt tct aag acg gtt atg aaa     1440
Gly Asp Ala Pro Glu Glu Glu Val Ser Leu Ser Lys Thr Val Met Lys
465                 470                 475                 480 ttt tgg gct aac ttc gcc cgt agt gga aac cct aat gga gaa gga ttg     1488
Phe Trp Ala Asn Phe Ala Arg Ser Gly Asn Pro Asn Gly Glu Gly Leu
                485                 490                 495 cct cac tgg ccg atg tac gat caa gag gag gga tac ctt caa att ggt     1536
Pro His Trp Pro Met Tyr Asp Gln Glu Glu Gly Tyr Leu Gln Ile Gly
            500                 505                 510 gtc aac act caa gca gct aag agg ttg aaa ggc gag gag gtt gct ttt     1584
Val Asn Thr Gln Ala Ala Lys Arg Leu Lys Gly Glu Glu Val Ala Phe
        515                 520                 525 tgg aac gac ctg ttg tcc aag gaa gca gca aag aag cca cct aag ata     1632
Trp Asn Asp Leu Leu Ser Lys Glu Ala Ala Lys Lys Pro Pro Lys Ile
    530                 535                 540 aag cac gcc gaa ttg taa                                             1650
Lys His Ala Glu Leu
545
```

<210> SEQ ID NO 37
<211> LENGTH: 549
<212> TYPE: PRT
<213> ORGANISM: artificial sequence
<220> FEATURE:
<223> OTHER INFORMATION: Synthetic Construct

<400> SEQUENCE: 37

```
Met Gly Gln Pro Ala Ser Pro Pro Val Val Asp Thr Ala Gln Gly Arg
1               5                   10                  15

Val Leu Gly Lys Tyr Val Ser Leu Glu Gly Leu Ala Gln Pro Val Ala
            20                  25                  30

Val Phe Leu Gly Val Pro Phe Ala Lys Pro Pro Leu Gly Ser Leu Arg
        35                  40                  45

Phe Ala Pro Pro Gln Pro Ala Glu Pro Trp Ser Phe Val Lys Asn Thr
    50                  55                  60

Thr Ser Tyr Pro Pro Met Cys Cys Gln Asp Pro Val Ala Gly Gln Met
65                  70                  75                  80

Thr Ser Asp Leu Phe Thr Asn Gly Lys Glu Arg Leu Ile Pro Glu Phe
                85                  90                  95

Ser Glu Asp Cys Leu Tyr Leu Asn Ile Tyr Thr Pro Ala Asp Leu Thr
            100                 105                 110

Lys Arg Gly Arg Leu Pro Val Met Val Trp Ile His Gly Gly Leu
        115                 120                 125

Val Val Gly Gly Ala Ser Thr Tyr Asp Gly Leu Ala Leu Ala Ala His
    130                 135                 140

Glu Asn Val Val Val Ala Ile Gln Tyr Arg Leu Gly Ile Trp Gly
145                 150                 155                 160
```

Phe Phe Ser Thr Gly Asp Glu His Ser Arg Gly Asn Trp Gly His Leu
                165                 170                 175

Asp Gln Val Ala Ala Leu His Trp Val Gln Glu Asn Ile Ala Asn Phe
            180                 185                 190

Gly Gly Asp Thr Gly Ser Val Thr Ile Phe Gly Glu Ser Ala Gly Gly
        195                 200                 205

Glu Ser Val Ser Val Leu Val Leu Ser Pro Leu Ala Lys Asn Leu Phe
210                 215                 220

His Arg Ala Ile Ser Glu Ser Gly Val Ala Leu Thr Ala Gly Leu Val
225                 230                 235                 240

Arg Lys Asp Met Lys Ala Ala Lys Gln Ile Ala Val Leu Ala Gly
                245                 250                 255

Cys Lys Thr Thr Thr Ser Ala Val Phe Val His Cys Leu Arg Gln Lys
                260                 265                 270

Ser Glu Asp Glu Leu Leu Asp Leu Thr Leu Lys Met Lys Phe Leu Thr
            275                 280                 285

Leu Asp Leu His Gly Asp Pro Arg Glu Ser His Pro Phe Leu Pro Thr
    290                 295                 300

Val Val Asp Gly Val Leu Leu Pro Lys Met Pro Glu Glu Ile Leu Ala
305                 310                 315                 320

Glu Lys Asp Phe Asn Thr Val Pro Tyr Ile Val Gly Ile Asn Lys Gln
                325                 330                 335

Glu Phe Gly Trp Leu Leu Pro Thr Met Met Gly Phe Pro Leu Ser Glu
            340                 345                 350

Gly Lys Leu Asp Gln Lys Thr Ala Thr Ser Leu Leu Trp Lys Ser Phe
        355                 360                 365

Pro Ile Thr Asn Ile Pro Glu Glu Leu Thr Pro Val Ala Thr Asp Lys
    370                 375                 380

Tyr Leu Gly Gly Thr Asp Asp Pro Val Lys Lys Asp Leu Phe Leu
385                 390                 395                 400

Asp Leu Met Gly Asp Val Val Phe Gly Val Pro Ser Val Thr Val Ala
                405                 410                 415

Arg Gln His Arg Asp Ala Gly Ala Pro Thr Tyr Met Tyr Glu Phe Gln
            420                 425                 430

Tyr Arg Pro Ser Phe Ser Ser Asp Lys Lys Pro Lys Thr Val Ile Gly
        435                 440                 445

Asp His Gly Asp Glu Ile Phe Ser Val Phe Gly Phe Pro Leu Leu Lys
    450                 455                 460

Gly Asp Ala Pro Glu Glu Val Ser Leu Ser Lys Thr Val Met Lys
465                 470                 475                 480

Phe Trp Ala Asn Phe Ala Arg Ser Gly Asn Pro Asn Gly Glu Gly Leu
                485                 490                 495

Pro His Trp Pro Met Tyr Asp Gln Glu Glu Gly Tyr Leu Gln Ile Gly
            500                 505                 510

Val Asn Thr Gln Ala Ala Lys Arg Leu Lys Gly Glu Glu Val Ala Phe
        515                 520                 525

Trp Asn Asp Leu Leu Ser Lys Glu Ala Ala Lys Lys Pro Pro Lys Ile
    530                 535                 540

Lys His Ala Glu Leu
545

<210> SEQ ID NO 38
<211> LENGTH: 1650

```
<212> TYPE: DNA
<213> ORGANISM: artificial sequence
<220> FEATURE:
<223> OTHER INFORMATION: protein with esterase activity
<220> FEATURE:
<221> NAME/KEY: CDS
<222> LOCATION: (1)..(1650)

<400> SEQUENCE: 38
```

| | | | | | | | | | | | | | | | | |
|---|---|---|---|---|---|---|---|---|---|---|---|---|---|---|---|---|
| atg | gga | caa | cca | gct | tcg | ccg | cct | gtc | gtt | gat | acc | gct | caa | gga | cga | 48 |
| Met | Gly | Gln | Pro | Ala | Ser | Pro | Pro | Val | Val | Asp | Thr | Ala | Gln | Gly | Arg | |
| 1 | | | 5 | | | | 10 | | | | | 15 | | | | |
| gtc | ttg | ggt | aag | tac | gtc | tct | tta | gag | gga | ttg | gca | caa | ccg | gtt | gct | 96 |
| Val | Leu | Gly | Lys | Tyr | Val | Ser | Leu | Glu | Gly | Leu | Ala | Gln | Pro | Val | Ala | |
| | | 20 | | | | | 25 | | | | | 30 | | | | |
| gtc | ttc | ttg | gga | gtc | cct | ttt | gct | aag | cca | cct | ctt | gga | tct | ttg | agg | 144 |
| Val | Phe | Leu | Gly | Val | Pro | Phe | Ala | Lys | Pro | Pro | Leu | Gly | Ser | Leu | Arg | |
| | 35 | | | | | 40 | | | | | 45 | | | | | |
| ttt | gcc | ccg | ccg | caa | cca | gca | gag | cca | tgg | tct | ttc | gtt | aag | aac | act | 192 |
| Phe | Ala | Pro | Pro | Gln | Pro | Ala | Glu | Pro | Trp | Ser | Phe | Val | Lys | Asn | Thr | |
| 50 | | | | | 55 | | | | | 60 | | | | | | |
| act | tcc | tac | cct | cca | atg | tgt | tgt | caa | gat | cca | gtc | gta | gaa | caa | atg | 240 |
| Thr | Ser | Tyr | Pro | Pro | Met | Cys | Cys | Gln | Asp | Pro | Val | Val | Glu | Gln | Met | |
| 65 | | | | 70 | | | | | 75 | | | | | 80 | | |
| acg | tca | gac | cta | ttc | act | aac | gga | aag | gaa | agg | ctt | acc | ctg | gag | ttc | 288 |
| Thr | Ser | Asp | Leu | Phe | Thr | Asn | Gly | Lys | Glu | Arg | Leu | Thr | Leu | Glu | Phe | |
| | | | | 85 | | | | | 90 | | | | | 95 | | |
| tct | gag | gat | tgc | ctt | tac | cta | aat | att | tac | act | cct | gcc | gat | ttg | aca | 336 |
| Ser | Glu | Asp | Cys | Leu | Tyr | Leu | Asn | Ile | Tyr | Thr | Pro | Ala | Asp | Leu | Thr | |
| | | | 100 | | | | | 105 | | | | | 110 | | | |
| aag | agg | ggt | agg | ttg | ccg | gtt | atg | gtt | tgg | att | cat | gga | gga | ggt | ttg | 384 |
| Lys | Arg | Gly | Arg | Leu | Pro | Val | Met | Val | Trp | Ile | His | Gly | Gly | Gly | Leu | |
| | | 115 | | | | | 120 | | | | | 125 | | | | |
| gtt | gtt | ggc | gga | gca | tcc | act | tat | gac | gga | ttg | gct | ctt | gcc | gcg | cac | 432 |
| Val | Val | Gly | Gly | Ala | Ser | Thr | Tyr | Asp | Gly | Leu | Ala | Leu | Ala | Ala | His | |
| | 130 | | | | | 135 | | | | | 140 | | | | | |
| gag | aac | gtt | gtt | gtt | gtt | gct | att | caa | tac | cgt | ttg | ggt | att | tgg | gga | 480 |
| Glu | Asn | Val | Val | Val | Val | Ala | Ile | Gln | Tyr | Arg | Leu | Gly | Ile | Trp | Gly | |
| 145 | | | | | 150 | | | | | 155 | | | | | 160 | |
| ttt | ttc | tcc | aca | gga | gat | gag | cat | tcc | cgt | gga | aac | tgg | ggc | cat | tta | 528 |
| Phe | Phe | Ser | Thr | Gly | Asp | Glu | His | Ser | Arg | Gly | Asn | Trp | Gly | His | Leu | |
| | | | | 165 | | | | | 170 | | | | | 175 | | |
| gat | caa | gtt | gct | gca | ttg | cat | tgg | gtc | caa | gaa | aac | att | gct | aac | ttc | 576 |
| Asp | Gln | Val | Ala | Ala | Leu | His | Trp | Val | Gln | Glu | Asn | Ile | Ala | Asn | Phe | |
| | | | 180 | | | | | 185 | | | | | 190 | | | |
| gga | ggt | gat | cca | ggt | tct | gtt | act | att | ttc | gga | gaa | tca | gca | ggc | gga | 624 |
| Gly | Gly | Asp | Pro | Gly | Ser | Val | Thr | Ile | Phe | Gly | Glu | Ser | Ala | Gly | Gly | |
| | | 195 | | | | | 200 | | | | | 205 | | | | |
| gag | agt | gtc | tct | gta | ttg | gtt | tta | tca | cca | tta | gct | aag | aac | ctt | ttt | 672 |
| Glu | Ser | Val | Ser | Val | Leu | Val | Leu | Ser | Pro | Leu | Ala | Lys | Asn | Leu | Phe | |
| | 210 | | | | | 215 | | | | | 220 | | | | | |
| cat | cgt | gct | att | tcc | gaa | agt | ggt | gtt | gct | ttt | acc | gcc | ggt | ttg | gtc | 720 |
| His | Arg | Ala | Ile | Ser | Glu | Ser | Gly | Val | Ala | Phe | Thr | Ala | Gly | Leu | Val | |
| 225 | | | | | 230 | | | | | 235 | | | | | 240 | |
| agg | aag | gat | atg | aag | gcc | gca | gcc | aag | cag | atc | gct | gtc | ctt | gca | gga | 768 |
| Arg | Lys | Asp | Met | Lys | Ala | Ala | Ala | Lys | Gln | Ile | Ala | Val | Leu | Ala | Gly | |
| | | | | 245 | | | | | 250 | | | | | 255 | | |
| tgc | aaa | act | act | act | tcg | gca | gtc | ttc | gtg | cat | tgt | ttg | cgt | caa | aag | 816 |
| Cys | Lys | Thr | Thr | Thr | Ser | Ala | Val | Phe | Val | His | Cys | Leu | Arg | Gln | Lys | |
| | | | 260 | | | | | 265 | | | | | 270 | | | |
| tcg | gaa | gat | gaa | ctt | tta | gac | ctc | acg | ttg | aag | atg | aaa | ttc | ttt | gcc | 864 |

```
Ser Glu Asp Glu Leu Leu Asp Leu Thr Leu Lys Met Lys Phe Phe Ala
            275                 280                 285 ctt gac tta cac gga gat cca agg gaa tct cac cct ttt ttg acc act       912
Leu Asp Leu His Gly Asp Pro Arg Glu Ser His Pro Phe Leu Thr Thr
        290                 295                 300 gtt gtt gac gga gtt ttg ttg cct aag atg cct gag gaa atc ttg gcc       960
Val Val Asp Gly Val Leu Leu Pro Lys Met Pro Glu Glu Ile Leu Ala
305                 310                 315                 320 gag aag gac ttt aac acc gtc cca tac att gtt gga att aac aag cag      1008
Glu Lys Asp Phe Asn Thr Val Pro Tyr Ile Val Gly Ile Asn Lys Gln
                325                 330                 335 gag ttc gga tgg ctt ttg cca acg atg atg gga ttt cct ctt tcc gag      1056
Glu Phe Gly Trp Leu Leu Pro Thr Met Met Gly Phe Pro Leu Ser Glu
            340                 345                 350 gga aag ttg gat caa aag acg gct acg tca ctt ttg tgg aag tcc tac      1104
Gly Lys Leu Asp Gln Lys Thr Ala Thr Ser Leu Leu Trp Lys Ser Tyr
        355                 360                 365 cca att gcc aac att cct gaa gag ttg acc cca gtt gct acc gat aag      1152
Pro Ile Ala Asn Ile Pro Glu Glu Leu Thr Pro Val Ala Thr Asp Lys
370                 375                 380 tat tta gga gga aca gat gat cct gtc aaa aag aaa gat ttg ttt ttg      1200
Tyr Leu Gly Gly Thr Asp Asp Pro Val Lys Lys Lys Asp Leu Phe Leu
385                 390                 395                 400 gat ctg atg gga gac gtt gtt ttc ggc gtc cca tca gtt acg gtt gct      1248
Asp Leu Met Gly Asp Val Val Phe Gly Val Pro Ser Val Thr Val Ala
                405                 410                 415 cgt cag cat agg gac gca gga gct cca act tac atg tat gag ttc caa      1296
Arg Gln His Arg Asp Ala Gly Ala Pro Thr Tyr Met Tyr Glu Phe Gln
            420                 425                 430 tat cgt cca tct ttt tca tcg gat aag aaa cct aag acg gtt att gga      1344
Tyr Arg Pro Ser Phe Ser Ser Asp Lys Lys Pro Lys Thr Val Ile Gly
        435                 440                 445 gat cat gga gac gaa att ttt tcc gtc ttc ggc ttc cca ttg ctc aaa      1392
Asp His Gly Asp Glu Ile Phe Ser Val Phe Gly Phe Pro Leu Leu Lys
450                 455                 460 ggt gac gct cca gag gaa gaa gtc agt ctt tct aag acg gtt atg aaa      1440
Gly Asp Ala Pro Glu Glu Glu Val Ser Leu Ser Lys Thr Val Met Lys
465                 470                 475                 480 ttt tgg gct aac ttc gcc cgt agt gga aac cct aat gga gaa gga ttg      1488
Phe Trp Ala Asn Phe Ala Arg Ser Gly Asn Pro Asn Gly Glu Gly Leu
                485                 490                 495 cct cac tgg ccg atg tac gat caa gag gag gga tac ctt caa att ggt      1536
Pro His Trp Pro Met Tyr Asp Gln Glu Glu Gly Tyr Leu Gln Ile Gly
            500                 505                 510 gtc aac act caa gca gct aag agg ttg aaa ggc gag gag gtt gct ttt      1584
Val Asn Thr Gln Ala Ala Lys Arg Leu Lys Gly Glu Glu Val Ala Phe
        515                 520                 525 tgg aac gac ctg ttg tcc aag gaa gca gca aag aag cca cct aag ata      1632
Trp Asn Asp Leu Leu Ser Lys Glu Ala Ala Lys Lys Pro Pro Lys Ile
530                 535                 540 aag cac gcc gaa ttg taa                                              1650
Lys His Ala Glu Leu
545

<210> SEQ ID NO 39
<211> LENGTH: 549
<212> TYPE: PRT
<213> ORGANISM: artificial sequence
<220> FEATURE:
<223> OTHER INFORMATION: Synthetic Construct
```

-continued

```
<400> SEQUENCE: 39

Met Gly Gln Pro Ala Ser Pro Pro Val Asp Thr Ala Gln Gly Arg
1               5                   10                  15

Val Leu Gly Lys Tyr Val Ser Leu Glu Gly Leu Ala Gln Pro Val Ala
            20                  25                  30

Val Phe Leu Gly Val Pro Phe Ala Lys Pro Pro Leu Gly Ser Leu Arg
        35                  40                  45

Phe Ala Pro Pro Gln Pro Ala Glu Pro Trp Ser Phe Val Lys Asn Thr
    50                  55                  60

Thr Ser Tyr Pro Pro Met Cys Cys Gln Asp Pro Val Val Glu Gln Met
65                  70                  75                  80

Thr Ser Asp Leu Phe Thr Asn Gly Lys Glu Arg Leu Thr Leu Glu Phe
                85                  90                  95

Ser Glu Asp Cys Leu Tyr Leu Asn Ile Tyr Thr Pro Ala Asp Leu Thr
            100                 105                 110

Lys Arg Gly Arg Leu Pro Val Met Val Trp Ile His Gly Gly Gly Leu
        115                 120                 125

Val Val Gly Gly Ala Ser Thr Tyr Asp Gly Leu Ala Leu Ala Ala His
    130                 135                 140

Glu Asn Val Val Val Ala Ile Gln Tyr Arg Leu Gly Ile Trp Gly
145                 150                 155                 160

Phe Phe Ser Thr Gly Asp Glu His Ser Arg Gly Asn Trp Gly His Leu
                165                 170                 175

Asp Gln Val Ala Ala Leu His Trp Val Gln Glu Asn Ile Ala Asn Phe
            180                 185                 190

Gly Gly Asp Pro Gly Ser Val Thr Ile Phe Gly Glu Ser Ala Gly Gly
        195                 200                 205

Glu Ser Val Ser Val Leu Val Leu Ser Pro Leu Ala Lys Asn Leu Phe
    210                 215                 220

His Arg Ala Ile Ser Glu Ser Gly Val Ala Phe Thr Ala Gly Leu Val
225                 230                 235                 240

Arg Lys Asp Met Lys Ala Ala Lys Gln Ile Ala Val Leu Ala Gly
                245                 250                 255

Cys Lys Thr Thr Thr Ser Ala Val Phe Val His Cys Leu Arg Gln Lys
            260                 265                 270

Ser Glu Asp Glu Leu Leu Asp Leu Thr Leu Lys Met Lys Phe Phe Ala
        275                 280                 285

Leu Asp Leu His Gly Asp Pro Arg Glu Ser His Pro Phe Leu Thr Thr
    290                 295                 300

Val Val Asp Gly Val Leu Leu Pro Lys Met Pro Glu Glu Ile Leu Ala
305                 310                 315                 320

Glu Lys Asp Phe Asn Thr Val Pro Tyr Ile Val Gly Ile Asn Lys Gln
                325                 330                 335

Glu Phe Gly Trp Leu Leu Pro Thr Met Met Gly Phe Pro Leu Ser Glu
            340                 345                 350

Gly Lys Leu Asp Gln Lys Thr Ala Thr Ser Leu Leu Trp Lys Ser Tyr
        355                 360                 365

Pro Ile Ala Asn Ile Pro Glu Glu Leu Thr Pro Val Ala Thr Asp Lys
    370                 375                 380

Tyr Leu Gly Gly Thr Asp Asp Pro Val Lys Lys Lys Asp Leu Phe Leu
385                 390                 395                 400

Asp Leu Met Gly Asp Val Val Phe Gly Val Pro Ser Val Thr Val Ala
                405                 410                 415
```

```
Arg Gln His Arg Asp Ala Gly Ala Pro Thr Tyr Met Tyr Glu Phe Gln
            420                 425                 430

Tyr Arg Pro Ser Phe Ser Ser Asp Lys Lys Pro Lys Thr Val Ile Gly
        435                 440                 445

Asp His Gly Asp Glu Ile Phe Ser Val Phe Gly Phe Pro Leu Leu Lys
    450                 455                 460

Gly Asp Ala Pro Glu Glu Val Ser Leu Ser Lys Thr Val Met Lys
465                 470                 475                 480

Phe Trp Ala Asn Phe Ala Arg Ser Gly Asn Pro Asn Gly Glu Gly Leu
                485                 490                 495

Pro His Trp Pro Met Tyr Asp Gln Glu Glu Gly Tyr Leu Gln Ile Gly
            500                 505                 510

Val Asn Thr Gln Ala Ala Lys Arg Leu Lys Gly Glu Glu Val Ala Phe
        515                 520                 525

Trp Asn Asp Leu Leu Ser Lys Glu Ala Ala Lys Lys Pro Pro Lys Ile
    530                 535                 540

Lys His Ala Glu Leu
545

<210> SEQ ID NO 40
<211> LENGTH: 1650
<212> TYPE: DNA
<213> ORGANISM: artificial sequence
<220> FEATURE:
<223> OTHER INFORMATION: protein with esterase activity
<220> FEATURE:
<221> NAME/KEY: CDS
<222> LOCATION: (1)..(1650)

<400> SEQUENCE: 40 atg gga caa cca gct tcg ccg cct gtc gtt gat acc gct caa gga cga      48
Met Gly Gln Pro Ala Ser Pro Pro Val Val Asp Thr Ala Gln Gly Arg
1               5                   10                  15 gtc ttg ggt aag tac gtc tct tta gag gga ttg gca caa ccg gtt gct      96
Val Leu Gly Lys Tyr Val Ser Leu Glu Gly Leu Ala Gln Pro Val Ala
            20                  25                  30 gtc ttc ttg gga gtc cct ttt gct aag cca cct ctt gga tct ttg agg     144
Val Phe Leu Gly Val Pro Phe Ala Lys Pro Pro Leu Gly Ser Leu Arg
        35                  40                  45 ttt gcc ccg ccg caa cca gca gag cca tgg tct ttc gtt aag aac act     192
Phe Ala Pro Pro Gln Pro Ala Glu Pro Trp Ser Phe Val Lys Asn Thr
    50                  55                  60 act tcc tac cct cca atg tgt tgt caa gaa cca atc gga gga caa atg     240
Thr Ser Tyr Pro Pro Met Cys Cys Gln Glu Pro Ile Gly Gly Gln Met
65                  70                  75                  80 ctt tca gac cta ttc act aac aga aag gaa agg ctt atc ccg gag ttc     288
Leu Ser Asp Leu Phe Thr Asn Arg Lys Glu Arg Leu Ile Pro Glu Phe
                85                  90                  95 tct gag gat tgc ctt tac cta aat att tac act cct gcc gat ttg aca     336
Ser Glu Asp Cys Leu Tyr Leu Asn Ile Tyr Thr Pro Ala Asp Leu Thr
            100                 105                 110 aag agg ggt agg ttg ccg gtt atg gtt tgg att cat gga gga ggt ttg     384
Lys Arg Gly Arg Leu Pro Val Met Val Trp Ile His Gly Gly Gly Leu
        115                 120                 125 gtt ctg ggc gga gca ccg atg tat gac gga gtg gtt ctt gcc gcg cac     432
Val Leu Gly Gly Ala Pro Met Tyr Asp Gly Val Val Leu Ala Ala His
    130                 135                 140 gag aac gtt gtt gtt gtt gct att caa tac cgt ttg ggt att tgg gga     480
Glu Asn Val Val Val Val Ala Ile Gln Tyr Arg Leu Gly Ile Trp Gly
```

-continued

```
                145                 150                 155                 160
ttt ttc tcc aca gga gat gag cat tcc cgt gga aac tgg ggc cat tta        528
Phe Phe Ser Thr Gly Asp Glu His Ser Arg Gly Asn Trp Gly His Leu
                165                 170                 175 gat caa gtt gct gca ttg cat tgg gtc caa gaa aac att gct aac ttc        576
Asp Gln Val Ala Ala Leu His Trp Val Gln Glu Asn Ile Ala Asn Phe
            180                 185                 190 gga ggt gat cca ggt tct gtt act att ttc gga gaa tca gca ggc gga        624
Gly Gly Asp Pro Gly Ser Val Thr Ile Phe Gly Glu Ser Ala Gly Gly
        195                 200                 205 gag agt gtc tct gta ttg gtt tta tca cca tta gct aag aac ctt ttt        672
Glu Ser Val Ser Val Leu Val Leu Ser Pro Leu Ala Lys Asn Leu Phe
    210                 215                 220 cat cgt gct att tcc gaa agt ggt gtt gct ttt acc gcc ggt ttg gtc        720
His Arg Ala Ile Ser Glu Ser Gly Val Ala Phe Thr Ala Gly Leu Val
225                 230                 235                 240 agg aag gat atg aag gcc gca gcc aag cag atc gct gtc ctt gca gga        768
Arg Lys Asp Met Lys Ala Ala Ala Lys Gln Ile Ala Val Leu Ala Gly
                245                 250                 255 tgc aaa act act act tcg gca gtc ttc gtg cat tgt ttg cgt caa aag        816
Cys Lys Thr Thr Thr Ser Ala Val Phe Val His Cys Leu Arg Gln Lys
            260                 265                 270 tcg gaa gat gaa ctt tta gac ctc acg ttg aag atg aaa ttc ttt gcc        864
Ser Glu Asp Glu Leu Leu Asp Leu Thr Leu Lys Met Lys Phe Phe Ala
        275                 280                 285 ctt gac tta cac gga gat cca agg gaa tct cac cct ttt ttg acc act        912
Leu Asp Leu His Gly Asp Pro Arg Glu Ser His Pro Phe Leu Thr Thr
    290                 295                 300 gtt gtt gac gga gtt ttg ttg cct aag atg cct gag gaa atc ttg gcc        960
Val Val Asp Gly Val Leu Leu Pro Lys Met Pro Glu Glu Ile Leu Ala
305                 310                 315                 320 gag aag gac ttt aac acc gtc cca tac att gtt gga att aac aag cag       1008
Glu Lys Asp Phe Asn Thr Val Pro Tyr Ile Val Gly Ile Asn Lys Gln
                325                 330                 335 gag ttc gga tgg ctt ttg cca acg atg atg gga ttt cct ctt tcc gag       1056
Glu Phe Gly Trp Leu Leu Pro Thr Met Met Gly Phe Pro Leu Ser Glu
            340                 345                 350 gga aag ttg gat caa aag acg gct acg tca ctt ttg tgg aag tcc tac       1104
Gly Lys Leu Asp Gln Lys Thr Ala Thr Ser Leu Leu Trp Lys Ser Tyr
        355                 360                 365 cca att gcc aac att cct gaa gag ttg acc cca gtt gct acc gat aag       1152
Pro Ile Ala Asn Ile Pro Glu Glu Leu Thr Pro Val Ala Thr Asp Lys
    370                 375                 380 tat tta gga gga aca gat gat cct gtc aaa aag aaa gat ttg ttt ttg       1200
Tyr Leu Gly Gly Thr Asp Asp Pro Val Lys Lys Lys Asp Leu Phe Leu
385                 390                 395                 400 gat ctg atg gga gac gtt gtt ttc ggc gtc cca tca gtt acg gtt gct       1248
Asp Leu Met Gly Asp Val Val Phe Gly Val Pro Ser Val Thr Val Ala
                405                 410                 415 cgt cag cat agg gac gca gga gct cca act tac atg tat gag ttc caa       1296
Arg Gln His Arg Asp Ala Gly Ala Pro Thr Tyr Met Tyr Glu Phe Gln
            420                 425                 430 tat cgt cca tct ttt tca tcg gat aag aaa cct aag acg gtt att gga       1344
Tyr Arg Pro Ser Phe Ser Ser Asp Lys Lys Pro Lys Thr Val Ile Gly
        435                 440                 445 gat cat gga gac gaa att ttt tcc gtc ttc ggc ttc cca ttg ctc aaa       1392
Asp His Gly Asp Glu Ile Phe Ser Val Phe Gly Phe Pro Leu Leu Lys
    450                 455                 460 ggt gac gct cca gag gaa gaa gtc agt ctt tct aag acg gtt atg aaa       1440
Gly Asp Ala Pro Glu Glu Glu Val Ser Leu Ser Lys Thr Val Met Lys
```

```
Gly Asp Ala Pro Glu Glu Val Ser Leu Ser Lys Thr Val Met Lys
465                 470                 475                 480 ttt tgg gct aac ttc gcc cgt agt gga aac cct aat gga gaa gga ttg    1488
Phe Trp Ala Asn Phe Ala Arg Ser Gly Asn Pro Asn Gly Glu Gly Leu
                        485                 490                 495 cct cac tgg ccg atg tac gat caa gag gag gga tac ctt caa att ggt   1536
Pro His Trp Pro Met Tyr Asp Gln Glu Glu Gly Tyr Leu Gln Ile Gly
            500                 505                 510 gtc aac act caa gca gct aag agg ttg aaa ggc gag gag gtt gct ttt   1584
Val Asn Thr Gln Ala Ala Lys Arg Leu Lys Gly Glu Glu Val Ala Phe
                515                 520                 525 tgg aac gac ctg ttg tcc aag gaa gca gca aag aag cca cct aag ata   1632
Trp Asn Asp Leu Leu Ser Lys Glu Ala Ala Lys Lys Pro Pro Lys Ile
            530                 535                 540 aag cac gcc gaa ttg taa                                           1650
Lys His Ala Glu Leu
545
```

<210> SEQ ID NO 41
<211> LENGTH: 549
<212> TYPE: PRT
<213> ORGANISM: artificial sequence
<220> FEATURE:
<223> OTHER INFORMATION: Synthetic Construct

<400> SEQUENCE: 41

```
Met Gly Gln Pro Ala Ser Pro Val Val Asp Thr Ala Gln Gly Arg
1               5                   10                  15

Val Leu Gly Lys Tyr Val Ser Leu Glu Gly Leu Ala Gln Pro Val Ala
                20                  25                  30

Val Phe Leu Gly Val Pro Phe Ala Lys Pro Pro Leu Gly Ser Leu Arg
            35                  40                  45

Phe Ala Pro Pro Gln Pro Ala Glu Pro Trp Ser Phe Val Lys Asn Thr
        50                  55                  60

Thr Ser Tyr Pro Pro Met Cys Cys Gln Glu Pro Ile Gly Gly Gln Met
65                  70                  75                  80

Leu Ser Asp Leu Phe Thr Asn Arg Lys Glu Arg Leu Ile Pro Glu Phe
                85                  90                  95

Ser Glu Asp Cys Leu Tyr Leu Asn Ile Tyr Thr Pro Ala Asp Leu Thr
            100                 105                 110

Lys Arg Gly Arg Leu Pro Val Met Val Trp Ile His Gly Gly Gly Leu
        115                 120                 125

Val Leu Gly Gly Ala Pro Met Tyr Asp Gly Val Val Leu Ala Ala His
    130                 135                 140

Glu Asn Val Val Val Ala Ile Gln Tyr Arg Leu Gly Ile Trp Gly
145                 150                 155                 160

Phe Phe Ser Thr Gly Asp Glu His Ser Arg Gly Asn Trp Gly His Leu
                165                 170                 175

Asp Gln Val Ala Ala Leu His Trp Val Gln Glu Asn Ile Ala Asn Phe
            180                 185                 190

Gly Gly Asp Pro Gly Ser Val Thr Ile Phe Gly Glu Ser Ala Gly Gly
        195                 200                 205

Glu Ser Val Ser Val Leu Val Leu Ser Pro Leu Ala Lys Asn Leu Phe
    210                 215                 220

His Arg Ala Ile Ser Glu Ser Gly Val Ala Phe Thr Ala Gly Leu Val
225                 230                 235                 240

Arg Lys Asp Met Lys Ala Ala Ala Lys Gln Ile Ala Val Leu Ala Gly
```

```
                    245                 250                 255
Cys Lys Thr Thr Thr Ser Ala Val Phe Val His Cys Leu Arg Gln Lys
                260                 265                 270

Ser Glu Asp Glu Leu Leu Asp Leu Thr Leu Lys Met Lys Phe Phe Ala
            275                 280                 285

Leu Asp Leu His Gly Asp Pro Arg Glu Ser His Pro Phe Leu Thr Thr
290                 295                 300

Val Val Asp Gly Val Leu Leu Pro Lys Met Pro Glu Glu Ile Leu Ala
305                 310                 315                 320

Glu Lys Asp Phe Asn Thr Val Pro Tyr Ile Val Gly Ile Asn Lys Gln
                325                 330                 335

Glu Phe Gly Trp Leu Leu Pro Thr Met Met Gly Phe Pro Leu Ser Glu
            340                 345                 350

Gly Lys Leu Asp Gln Lys Thr Ala Thr Ser Leu Leu Trp Lys Ser Tyr
        355                 360                 365

Pro Ile Ala Asn Ile Pro Glu Glu Leu Thr Pro Val Ala Thr Asp Lys
    370                 375                 380

Tyr Leu Gly Gly Thr Asp Asp Pro Val Lys Lys Lys Asp Leu Phe Leu
385                 390                 395                 400

Asp Leu Met Gly Asp Val Val Phe Gly Val Pro Ser Val Thr Val Ala
                405                 410                 415

Arg Gln His Arg Asp Ala Gly Ala Pro Thr Tyr Met Tyr Glu Phe Gln
            420                 425                 430

Tyr Arg Pro Ser Phe Ser Ser Asp Lys Lys Pro Lys Thr Val Ile Gly
        435                 440                 445

Asp His Gly Asp Glu Ile Phe Ser Val Phe Gly Phe Pro Leu Leu Lys
    450                 455                 460

Gly Asp Ala Pro Glu Glu Val Ser Leu Ser Lys Thr Val Met Lys
465                 470                 475                 480

Phe Trp Ala Asn Phe Ala Arg Ser Gly Asn Pro Asn Gly Glu Gly Leu
                485                 490                 495

Pro His Trp Pro Met Tyr Asp Gln Glu Gly Tyr Leu Gln Ile Gly
            500                 505                 510

Val Asn Thr Gln Ala Ala Lys Arg Leu Lys Gly Glu Glu Val Ala Phe
        515                 520                 525

Trp Asn Asp Leu Leu Ser Lys Glu Ala Ala Lys Lys Pro Pro Lys Ile
    530                 535                 540

Lys His Ala Glu Leu
545

<210> SEQ ID NO 42
<211> LENGTH: 1650
<212> TYPE: DNA
<213> ORGANISM: artificial sequence
<220> FEATURE:
<223> OTHER INFORMATION: protein with esterase activity
<220> FEATURE:
<221> NAME/KEY: CDS
<222> LOCATION: (1)..(1650)

<400> SEQUENCE: 42 atg gga caa cca gct tcg ccg cct gtc gtt gat acc gct caa gga cga      48
Met Gly Gln Pro Ala Ser Pro Pro Val Val Asp Thr Ala Gln Gly Arg
1               5                   10                  15 gtc ttg ggt aag tac gtc tct tta gag gga ttg gca caa ccg gtt gct      96
Val Leu Gly Lys Tyr Val Ser Leu Glu Gly Leu Ala Gln Pro Val Ala
            20                  25                  30
```

| | | |
|---|---|---|
| gtc ttc ttg gga gtc cct ttt gct aag cca cct ctt gga tct ttg agg<br>Val Phe Leu Gly Val Pro Phe Ala Lys Pro Pro Leu Gly Ser Leu Arg<br>35                     40                       45 | | 144 |
| ttt gcc ccg ccg caa cca gca gag cca tgg tct ttc gtt aag aac act<br>Phe Ala Pro Pro Gln Pro Ala Glu Pro Trp Ser Phe Val Lys Asn Thr<br>50                     55                       60 | | 192 |
| act tcc tac cct cca atg tgt tgt caa gaa cca atc gga gga caa atg<br>Thr Ser Tyr Pro Pro Met Cys Cys Gln Glu Pro Ile Gly Gly Gln Met<br>65                     70                       75                       80 | | 240 |
| ctt tca gac cta ttc act aac aga aag gaa agg ctt atc ccg gag ttc<br>Leu Ser Asp Leu Phe Thr Asn Arg Lys Glu Arg Leu Ile Pro Glu Phe<br>                     85                       90                       95 | | 288 |
| tct gag gat tgc ctt tac cta aat att tac act cct gcc gat ttg aca<br>Ser Glu Asp Cys Leu Tyr Leu Asn Ile Tyr Thr Pro Ala Asp Leu Thr<br>                    100                   105                  110 | | 336 |
| aag agg ggt agg ttg ccg gtt atg gtt tgg att cat gga gga ggt ttg<br>Lys Arg Gly Arg Leu Pro Val Met Val Trp Ile His Gly Gly Gly Leu<br>             115                       120                       125 | | 384 |
| gtt gtt ggc gga gca tcc act tat gac gga ttg gct ctt gcc gcg cac<br>Val Val Gly Gly Ala Ser Thr Tyr Asp Gly Leu Ala Leu Ala Ala His<br>130                     135                       140 | | 432 |
| gag aac gtt gtt gtt gtt gct att caa tac cgt ttg ggt att tgg gga<br>Glu Asn Val Val Val Val Ala Ile Gln Tyr Arg Leu Gly Ile Trp Gly<br>145                     150                       155                       160 | | 480 |
| ttt ttc tcc aca gga gat gag cat tcc cgt gga aac tgg ggc cat tta<br>Phe Phe Ser Thr Gly Asp Glu His Ser Arg Gly Asn Trp Gly His Leu<br>                    165                   170                  175 | | 528 |
| gat caa gtt gct gca ttg cat tgg gtc caa gaa aac att gct aac ttc<br>Asp Gln Val Ala Ala Leu His Trp Val Gln Glu Asn Ile Ala Asn Phe<br>                    180                   185                  190 | | 576 |
| gga ggt gat cca ggt tct gtt act att ttc gga gaa tca gca ggc gga<br>Gly Gly Asp Pro Gly Ser Val Thr Ile Phe Gly Glu Ser Ala Gly Gly<br>             195                       200                       205 | | 624 |
| gag agt gtc tct gta ttg gtt tta tca cca tta gct aag aac ctt ttt<br>Glu Ser Val Ser Val Leu Val Leu Ser Pro Leu Ala Lys Asn Leu Phe<br>210                     215                       220 | | 672 |
| cat cgt gct att tcc gaa agt ggt gtt gct tta acc gtc gct ttg gtc<br>His Arg Ala Ile Ser Glu Ser Gly Val Ala Leu Thr Val Ala Leu Val<br>225                     230                       235                       240 | | 720 |
| agg aag gat atg aag gcc gca gcc aag cag atc gct gtc ctt gca gga<br>Arg Lys Asp Met Lys Ala Ala Ala Lys Gln Ile Ala Val Leu Ala Gly<br>                    245                   250                  255 | | 768 |
| tgc aaa act act act tcg gca gtc ttc gtg cat tgt ttg cgt caa aag<br>Cys Lys Thr Thr Thr Ser Ala Val Phe Val His Cys Leu Arg Gln Lys<br>                    260                   265                  270 | | 816 |
| tcg gaa gat gaa ctt tta gac ctc acg ttg aag atg aaa ttc tta gcc<br>Ser Glu Asp Glu Leu Leu Asp Leu Thr Leu Lys Met Lys Phe Leu Ala<br>             275                       280                       285 | | 864 |
| ctt gac tta cac gga gat cca agg gaa tct cac cct ttt ttg acc act<br>Leu Asp Leu His Gly Asp Pro Arg Glu Ser His Pro Phe Leu Thr Thr<br>290                     295                       300 | | 912 |
| gtt gtt gac gga gtt ttg ttg cct aag atg cct gag gaa atc ttg gcc<br>Val Val Asp Gly Val Leu Leu Pro Lys Met Pro Glu Glu Ile Leu Ala<br>305                     310                       315                       320 | | 960 |
| gag aag gac ttt aac acc gtc cca tac att gtt gga att aac aag cag<br>Glu Lys Asp Phe Asn Thr Val Pro Tyr Ile Val Gly Ile Asn Lys Gln<br>                    325                   330                  335 | | 1008 |
| gag ttc gga tgg ctt ttg cca acg atg atg gga ttt cct ctt tcc gag<br>Glu Phe Gly Trp Leu Leu Pro Thr Met Met Gly Phe Pro Leu Ser Glu | | 1056 |

```
                       340                 345                 350
gga aag ttg gat caa aag acg gct acg tca ctt ttg tgg aag tcc tac    1104
Gly Lys Leu Asp Gln Lys Thr Ala Thr Ser Leu Leu Trp Lys Ser Tyr
            355                 360                 365 cca att gcc aac att cct gaa gag ttg acc cca gtt gct acc gat aag    1152
Pro Ile Ala Asn Ile Pro Glu Glu Leu Thr Pro Val Ala Thr Asp Lys
370                 375                 380 tat tta gga gga aca gat gat cct gtc aaa aag aaa gat ttg ttt ttg    1200
Tyr Leu Gly Gly Thr Asp Asp Pro Val Lys Lys Lys Asp Leu Phe Leu
385                 390                 395                 400 gat ctg atg gga gac gtt gtt ttc ggc gtc cca tca gtt acg gtt gct    1248
Asp Leu Met Gly Asp Val Val Phe Gly Val Pro Ser Val Thr Val Ala
                405                 410                 415 cgt cag cat agg gac gca gga gct cca act tac atg tat gag ttc caa    1296
Arg Gln His Arg Asp Ala Gly Ala Pro Thr Tyr Met Tyr Glu Phe Gln
            420                 425                 430 tat cgt cca tct ttt tca tcg gat aag aaa cct aag acg gtt att gga    1344
Tyr Arg Pro Ser Phe Ser Ser Asp Lys Lys Pro Lys Thr Val Ile Gly
        435                 440                 445 gat cat gga gac gaa att ttt tcc gtc ttc ggc ttc cca ttg ctc aaa    1392
Asp His Gly Asp Glu Ile Phe Ser Val Phe Gly Phe Pro Leu Leu Lys
450                 455                 460 ggt gac gct cca gag gaa gaa gtc agt ctt tct aag acg gtt atg aaa    1440
Gly Asp Ala Pro Glu Glu Glu Val Ser Leu Ser Lys Thr Val Met Lys
465                 470                 475                 480 ttt tgg gct aac ttc gcc cgt agt gga aac cct aat gga gaa gga ttg    1488
Phe Trp Ala Asn Phe Ala Arg Ser Gly Asn Pro Asn Gly Glu Gly Leu
                485                 490                 495 cct cac tgg ccg atg tac gat caa gag gag gga tac ctt caa att ggt    1536
Pro His Trp Pro Met Tyr Asp Gln Glu Glu Gly Tyr Leu Gln Ile Gly
            500                 505                 510 gtc aac act caa gca gct aag agg ttg aaa ggc gag gag gtt gct ttt    1584
Val Asn Thr Gln Ala Ala Lys Arg Leu Lys Gly Glu Glu Val Ala Phe
        515                 520                 525 tgg aac gac ctg ttg tcc aag gaa gca gca aag aag cca cct aag ata    1632
Trp Asn Asp Leu Leu Ser Lys Glu Ala Ala Lys Lys Pro Pro Lys Ile
530                 535                 540 aag cac gcc gaa ttg taa                                             1650
Lys His Ala Glu Leu
545

<210> SEQ ID NO 43
<211> LENGTH: 549
<212> TYPE: PRT
<213> ORGANISM: artificial sequence
<220> FEATURE:
<223> OTHER INFORMATION: Synthetic Construct

<400> SEQUENCE: 43

Met Gly Gln Pro Ala Ser Pro Val Val Asp Thr Ala Gln Gly Arg
1               5                   10                  15

Val Leu Gly Lys Tyr Val Ser Leu Glu Gly Leu Ala Gln Pro Val Ala
            20                  25                  30

Val Phe Leu Gly Val Pro Phe Ala Lys Pro Pro Leu Gly Ser Leu Arg
        35                  40                  45

Phe Ala Pro Pro Gln Pro Ala Glu Pro Trp Ser Phe Val Lys Asn Thr
    50                  55                  60

Thr Ser Tyr Pro Pro Met Cys Cys Gln Glu Pro Ile Gly Gly Gln Met
65                  70                  75                  80
```

```
Leu Ser Asp Leu Phe Thr Asn Arg Lys Glu Arg Leu Ile Pro Glu Phe
            85                  90                  95

Ser Glu Asp Cys Leu Tyr Leu Asn Ile Tyr Thr Pro Ala Asp Leu Thr
            100                 105                 110

Lys Arg Gly Arg Leu Pro Val Met Val Trp Ile His Gly Gly Gly Leu
            115                 120                 125

Val Val Gly Gly Ala Ser Thr Tyr Asp Gly Leu Ala Leu Ala Ala His
130                 135                 140

Glu Asn Val Val Val Ala Ile Gln Tyr Arg Leu Gly Ile Trp Gly
145                 150                 155                 160

Phe Phe Ser Thr Gly Asp Glu His Ser Arg Gly Asn Trp Gly His Leu
                165                 170                 175

Asp Gln Val Ala Ala Leu His Trp Val Gln Glu Asn Ile Ala Asn Phe
            180                 185                 190

Gly Gly Asp Pro Gly Ser Val Thr Ile Phe Gly Glu Ser Ala Gly Gly
            195                 200                 205

Glu Ser Val Ser Val Leu Val Leu Ser Pro Leu Ala Lys Asn Leu Phe
            210                 215                 220

His Arg Ala Ile Ser Glu Ser Gly Val Ala Leu Thr Val Ala Leu Val
225                 230                 235                 240

Arg Lys Asp Met Lys Ala Ala Lys Gln Ile Ala Val Leu Ala Gly
                245                 250                 255

Cys Lys Thr Thr Thr Ser Ala Val Phe Val His Cys Leu Arg Gln Lys
            260                 265                 270

Ser Glu Asp Glu Leu Leu Asp Leu Thr Leu Lys Met Lys Phe Leu Ala
            275                 280                 285

Leu Asp Leu His Gly Asp Pro Arg Glu Ser His Pro Phe Leu Thr Thr
            290                 295                 300

Val Val Asp Gly Val Leu Leu Pro Lys Met Pro Glu Glu Ile Leu Ala
305                 310                 315                 320

Glu Lys Asp Phe Asn Thr Val Pro Tyr Ile Val Gly Ile Asn Lys Gln
                325                 330                 335

Glu Phe Gly Trp Leu Leu Pro Thr Met Met Gly Phe Pro Leu Ser Glu
            340                 345                 350

Gly Lys Leu Asp Gln Lys Thr Ala Thr Ser Leu Leu Trp Lys Ser Tyr
            355                 360                 365

Pro Ile Ala Asn Ile Pro Glu Glu Leu Thr Pro Val Ala Thr Asp Lys
            370                 375                 380

Tyr Leu Gly Gly Thr Asp Asp Pro Val Lys Lys Asp Leu Phe Leu
385                 390                 395                 400

Asp Leu Met Gly Asp Val Val Phe Gly Val Pro Ser Val Thr Val Ala
            405                 410                 415

Arg Gln His Arg Asp Ala Gly Ala Pro Thr Tyr Met Tyr Glu Phe Gln
            420                 425                 430

Tyr Arg Pro Ser Phe Ser Asp Lys Lys Pro Lys Thr Val Ile Gly
            435                 440                 445

Asp His Gly Asp Glu Ile Phe Ser Val Phe Gly Phe Pro Leu Leu Lys
            450                 455                 460

Gly Asp Ala Pro Glu Glu Val Ser Leu Ser Lys Thr Val Met Lys
465                 470                 475                 480

Phe Trp Ala Asn Phe Ala Arg Ser Gly Asn Pro Asn Gly Glu Gly Leu
                485                 490                 495

Pro His Trp Pro Met Tyr Asp Gln Glu Glu Gly Tyr Leu Gln Ile Gly
```

|  |  |  | 500 |  |  |  | 505 |  |  |  | 510 |  |
|--|--|--|--|--|--|--|--|--|--|--|--|--|
| Val | Asn | Thr | Gln | Ala | Ala | Lys | Arg | Leu | Lys | Gly | Glu | Glu | Val | Ala | Phe |
|  |  |  | 515 |  |  |  | 520 |  |  |  | 525 |  |

Trp Asn Asp Leu Leu Ser Lys Glu Ala Ala Lys Lys Pro Pro Lys Ile
    530             535              540

Lys His Ala Glu Leu
545

```
<210> SEQ ID NO 44
<211> LENGTH: 1650
<212> TYPE: DNA
<213> ORGANISM: artificial sequence
<220> FEATURE:
<223> OTHER INFORMATION: protein with esterase activity
<220> FEATURE:
<221> NAME/KEY: CDS
<222> LOCATION: (1)..(1650)

<400> SEQUENCE: 44
```

| atg | gga | caa | cca | gct | tcg | ccg | cct | gtc | gtt | gat | acc | gct | caa | gga | cga | 48 |
|--|--|--|--|--|--|--|--|--|--|--|--|--|--|--|--|--|
| Met | Gly | Gln | Pro | Ala | Ser | Pro | Pro | Val | Val | Asp | Thr | Ala | Gln | Gly | Arg |  |
| 1 |  |  |  | 5 |  |  |  |  | 10 |  |  |  |  | 15 |  |  |

| gtc | ttg | ggt | aag | tac | gtc | tct | tta | gag | gga | ttg | gca | caa | ccg | gtt | gct | 96 |
|--|--|--|--|--|--|--|--|--|--|--|--|--|--|--|--|--|
| Val | Leu | Gly | Lys | Tyr | Val | Ser | Leu | Glu | Gly | Leu | Ala | Gln | Pro | Val | Ala |  |
|  |  |  | 20 |  |  |  |  | 25 |  |  |  |  | 30 |  |  |  |

| gtc | ttc | ttg | gga | gtc | cct | ttt | gct | aag | cca | cct | ctt | gga | tct | ttg | agg | 144 |
|--|--|--|--|--|--|--|--|--|--|--|--|--|--|--|--|--|
| Val | Phe | Leu | Gly | Val | Pro | Phe | Ala | Lys | Pro | Pro | Leu | Gly | Ser | Leu | Arg |  |
|  |  | 35 |  |  |  |  | 40 |  |  |  |  | 45 |  |  |  |  |

| ttt | gcc | ccg | ccg | caa | cca | gca | gag | cca | tgg | tct | ttc | gtt | aag | aac | act | 192 |
|--|--|--|--|--|--|--|--|--|--|--|--|--|--|--|--|--|
| Phe | Ala | Pro | Pro | Gln | Pro | Ala | Glu | Pro | Trp | Ser | Phe | Val | Lys | Asn | Thr |  |
| 50 |  |  |  |  | 55 |  |  |  |  | 60 |  |  |  |  |  |  |

| act | tcc | tac | cct | cca | atg | tgt | tgt | caa | gaa | cca | atc | gga | gga | caa | atg | 240 |
|--|--|--|--|--|--|--|--|--|--|--|--|--|--|--|--|--|
| Thr | Ser | Tyr | Pro | Pro | Met | Cys | Cys | Gln | Glu | Pro | Ile | Gly | Gly | Gln | Met |  |
| 65 |  |  |  | 70 |  |  |  |  | 75 |  |  |  |  | 80 |  |  |

| ctt | tca | gac | cta | ttc | act | aac | aga | aag | gaa | agg | ctt | atc | ccg | gag | ttc | 288 |
|--|--|--|--|--|--|--|--|--|--|--|--|--|--|--|--|--|
| Leu | Ser | Asp | Leu | Phe | Thr | Asn | Arg | Lys | Glu | Arg | Leu | Ile | Pro | Glu | Phe |  |
|  |  |  | 85 |  |  |  |  | 90 |  |  |  |  | 95 |  |  |  |

| tct | gag | gat | tgc | ctt | tac | cta | aat | att | tac | act | cct | gcc | gat | ttg | aca | 336 |
|--|--|--|--|--|--|--|--|--|--|--|--|--|--|--|--|--|
| Ser | Glu | Asp | Cys | Leu | Tyr | Leu | Asn | Ile | Tyr | Thr | Pro | Ala | Asp | Leu | Thr |  |
|  |  | 100 |  |  |  |  | 105 |  |  |  |  | 110 |  |  |  |  |

| aag | agg | ggt | agg | ttg | ccg | gtt | atg | gtt | tgg | att | cat | gga | gga | ggt | ttg | 384 |
|--|--|--|--|--|--|--|--|--|--|--|--|--|--|--|--|--|
| Lys | Arg | Gly | Arg | Leu | Pro | Val | Met | Val | Trp | Ile | His | Gly | Gly | Gly | Leu |  |
| 115 |  |  |  |  | 120 |  |  |  |  | 125 |  |  |  |  |  |  |

| gtt | gtt | ggc | gga | gca | tcc | act | tat | gac | gga | ttg | gct | ctt | gcc | gcg | cac | 432 |
|--|--|--|--|--|--|--|--|--|--|--|--|--|--|--|--|--|
| Val | Val | Gly | Gly | Ala | Ser | Thr | Tyr | Asp | Gly | Leu | Ala | Leu | Ala | Ala | His |  |
|  | 130 |  |  |  |  | 135 |  |  |  |  | 140 |  |  |  |  |  |

| gag | aac | gtt | gtt | gtt | gtt | gct | att | caa | tac | cgt | ttg | ggt | att | tgg | gga | 480 |
|--|--|--|--|--|--|--|--|--|--|--|--|--|--|--|--|--|
| Glu | Asn | Val | Val | Val | Val | Ala | Ile | Gln | Tyr | Arg | Leu | Gly | Ile | Trp | Gly |  |
| 145 |  |  |  | 150 |  |  |  |  | 155 |  |  |  |  | 160 |  |  |

| ttt | ttc | tcc | aca | gga | gat | gag | cat | tcc | cgt | gga | aac | tgg | ggc | cat | tta | 528 |
|--|--|--|--|--|--|--|--|--|--|--|--|--|--|--|--|--|
| Phe | Phe | Ser | Thr | Gly | Asp | Glu | His | Ser | Arg | Gly | Asn | Trp | Gly | His | Leu |  |
|  |  |  | 165 |  |  |  |  | 170 |  |  |  |  | 175 |  |  |  |

| gat | caa | gtt | gct | gca | ttg | cat | tgg | gtc | caa | gaa | aac | att | gct | aac | ttc | 576 |
|--|--|--|--|--|--|--|--|--|--|--|--|--|--|--|--|--|
| Asp | Gln | Val | Ala | Ala | Leu | His | Trp | Val | Gln | Glu | Asn | Ile | Ala | Asn | Phe |  |
|  | 180 |  |  |  |  | 185 |  |  |  |  | 190 |  |  |  |  |  |

| gga | ggt | gat | cca | ggt | tct | gtt | act | att | ttc | gga | gaa | tca | gca | ggc | gga | 624 |
|--|--|--|--|--|--|--|--|--|--|--|--|--|--|--|--|--|
| Gly | Gly | Asp | Pro | Gly | Ser | Val | Thr | Ile | Phe | Gly | Glu | Ser | Ala | Gly | Gly |  |
| 195 |  |  |  | 200 |  |  |  |  | 205 |  |  |  |  |  |  |  |

| gag | agt | gtc | tct | gta | ttg | gtt | tta | tca | cca | tta | gct | aag | aac | ctt | ttt | 672 |
|--|--|--|--|--|--|--|--|--|--|--|--|--|--|--|--|--|
| Glu | Ser | Val | Ser | Val | Leu | Val | Leu | Ser | Pro | Leu | Ala | Lys | Asn | Leu | Phe |  |
| 210 |  |  |  | 215 |  |  |  |  | 220 |  |  |  |  |  |  |  |

```
cat cgt gct att tcc gaa agt ggt gtt gct ttt acc gcc ggt ttg gtc      720
His Arg Ala Ile Ser Glu Ser Gly Val Ala Phe Thr Ala Gly Leu Val
225                 230                 235                 240 agg aag gat atg aag gcc gca gcc aag cag atc gct gtc ctt gca gga      768
Arg Lys Asp Met Lys Ala Ala Ala Lys Gln Ile Ala Val Leu Ala Gly
            245                 250                 255 tgc aaa act act act tcg gca gtc ttc gtg cat tgt ttg cgt caa aag      816
Cys Lys Thr Thr Thr Ser Ala Val Phe Val His Cys Leu Arg Gln Lys
        260                 265                 270 tcg gaa gat gaa ctt tta gac ctc acg ttg aag atg aaa ttc ctg acc      864
Ser Glu Asp Glu Leu Leu Asp Leu Thr Leu Lys Met Lys Phe Leu Thr
    275                 280                 285 ctt gac ttt cac gga gat caa agg gaa tct cac cct ttt ttg ccg act      912
Leu Asp Phe His Gly Asp Gln Arg Glu Ser His Pro Phe Leu Pro Thr
290                 295                 300 gtt gtt gac gga gtt ttg ttg cct aag atg cct gag gaa atc ttg gcc      960
Val Val Asp Gly Val Leu Leu Pro Lys Met Pro Glu Glu Ile Leu Ala
305                 310                 315                 320 gag aag gac ttt aac acc gtc cca tac att gtt gga att aac aag cag     1008
Glu Lys Asp Phe Asn Thr Val Pro Tyr Ile Val Gly Ile Asn Lys Gln
            325                 330                 335 gag ttc gga tgg ctt ttg cca acg atg atg gga ttt cct ctt tcc gag     1056
Glu Phe Gly Trp Leu Leu Pro Thr Met Met Gly Phe Pro Leu Ser Glu
        340                 345                 350 gga aag ttg gat caa aag acg gct acg tca ctt ttg tgg aag tcc tac     1104
Gly Lys Leu Asp Gln Lys Thr Ala Thr Ser Leu Leu Trp Lys Ser Tyr
    355                 360                 365 cca att gcc aac att cct gaa gag ttg acc cca gtt gct acc gat aag     1152
Pro Ile Ala Asn Ile Pro Glu Glu Leu Thr Pro Val Ala Thr Asp Lys
370                 375                 380 tat tta gga gga aca gat gat cct gtc aaa aag aaa gat ttg ttt ttg     1200
Tyr Leu Gly Gly Thr Asp Asp Pro Val Lys Lys Lys Asp Leu Phe Leu
385                 390                 395                 400 gat ctg atg gga gac gtt gtt ttc ggc gtc cca tca gtt acg gtt gct     1248
Asp Leu Met Gly Asp Val Val Phe Gly Val Pro Ser Val Thr Val Ala
            405                 410                 415 cgt cag cat agg gac gca gga gct cca act tac atg tat gag ttc caa     1296
Arg Gln His Arg Asp Ala Gly Ala Pro Thr Tyr Met Tyr Glu Phe Gln
        420                 425                 430 tat cgt cca tct ttt tca tcg gat aag aaa cct aag acg gtt att gga     1344
Tyr Arg Pro Ser Phe Ser Ser Asp Lys Lys Pro Lys Thr Val Ile Gly
    435                 440                 445 gat cat gga gac gaa att ttt tcc gtc ttc ggc ttc cca ttg ctc aaa     1392
Asp His Gly Asp Glu Ile Phe Ser Val Phe Gly Phe Pro Leu Leu Lys
450                 455                 460 ggt gac gct cca gag gaa gaa gtc agt ctt tct aag acg gtt atg aaa     1440
Gly Asp Ala Pro Glu Glu Glu Val Ser Leu Ser Lys Thr Val Met Lys
465                 470                 475                 480 ttt tgg gct aac ttc gcc cgt agt gga aac cct aat gga gaa gga ttg     1488
Phe Trp Ala Asn Phe Ala Arg Ser Gly Asn Pro Asn Gly Glu Gly Leu
            485                 490                 495 cct cac tgg ccg atg tac gat caa gag gag gga tac ctt caa att ggt     1536
Pro His Trp Pro Met Tyr Asp Gln Glu Glu Gly Tyr Leu Gln Ile Gly
        500                 505                 510 gtc aac act caa gca gct aag agg ttg aaa ggc gag gag gtt gct ttt     1584
Val Asn Thr Gln Ala Ala Lys Arg Leu Lys Gly Glu Glu Val Ala Phe
    515                 520                 525 tgg aac gac ctg ttg tcc aag gaa gca gca aag aag cca cct aag ata     1632
Trp Asn Asp Leu Leu Ser Lys Glu Ala Ala Lys Lys Pro Pro Lys Ile
```

```
              530                 535                 540
aag cac gcc gaa ttg taa                                                    1650
Lys His Ala Glu Leu
545

<210> SEQ ID NO 45
<211> LENGTH: 549
<212> TYPE: PRT
<213> ORGANISM: artificial sequence
<220> FEATURE:
<223> OTHER INFORMATION: Synthetic Construct

<400> SEQUENCE: 45

Met Gly Gln Pro Ala Ser Pro Pro Val Val Asp Thr Ala Gln Gly Arg
1               5                   10                  15

Val Leu Gly Lys Tyr Val Ser Leu Glu Gly Leu Ala Gln Pro Val Ala
            20                  25                  30

Val Phe Leu Gly Val Pro Phe Ala Lys Pro Pro Leu Gly Ser Leu Arg
        35                  40                  45

Phe Ala Pro Pro Gln Pro Ala Glu Pro Trp Ser Phe Val Lys Asn Thr
    50                  55                  60

Thr Ser Tyr Pro Pro Met Cys Cys Gln Glu Pro Ile Gly Gly Gln Met
65                  70                  75                  80

Leu Ser Asp Leu Phe Thr Asn Arg Lys Glu Arg Leu Ile Pro Glu Phe
                85                  90                  95

Ser Glu Asp Cys Leu Tyr Leu Asn Ile Tyr Thr Pro Ala Asp Leu Thr
            100                 105                 110

Lys Arg Gly Arg Leu Pro Val Met Val Trp Ile His Gly Gly Gly Leu
        115                 120                 125

Val Val Gly Gly Ala Ser Thr Tyr Asp Gly Leu Ala Leu Ala Ala His
    130                 135                 140

Glu Asn Val Val Val Ala Ile Gln Tyr Arg Leu Gly Ile Trp Gly
145                 150                 155                 160

Phe Phe Ser Thr Gly Asp Glu His Ser Arg Gly Asn Trp Gly His Leu
                165                 170                 175

Asp Gln Val Ala Ala Leu His Trp Val Gln Glu Asn Ile Ala Asn Phe
            180                 185                 190

Gly Gly Asp Pro Gly Ser Val Thr Ile Phe Gly Glu Ser Ala Gly Gly
        195                 200                 205

Glu Ser Val Ser Val Leu Val Leu Ser Pro Leu Ala Lys Asn Leu Phe
    210                 215                 220

His Arg Ala Ile Ser Glu Ser Gly Val Ala Phe Thr Ala Gly Leu Val
225                 230                 235                 240

Arg Lys Asp Met Lys Ala Ala Lys Gln Ile Ala Val Leu Ala Gly
                245                 250                 255

Cys Lys Thr Thr Thr Ser Ala Val Phe Val His Cys Leu Arg Gln Lys
            260                 265                 270

Ser Glu Asp Glu Leu Leu Asp Leu Thr Leu Lys Met Lys Phe Leu Thr
        275                 280                 285

Leu Asp Phe His Gly Asp Gln Arg Glu Ser His Pro Phe Leu Pro Thr
    290                 295                 300

Val Val Asp Gly Val Leu Leu Pro Lys Met Pro Glu Glu Ile Leu Ala
305                 310                 315                 320

Glu Lys Asp Phe Asn Thr Val Pro Tyr Ile Val Gly Ile Asn Lys Gln
                325                 330                 335
```

-continued

```
Glu Phe Gly Trp Leu Leu Pro Thr Met Met Gly Phe Pro Leu Ser Glu
            340                 345                 350

Gly Lys Leu Asp Gln Lys Thr Ala Thr Ser Leu Leu Trp Lys Ser Tyr
        355                 360                 365

Pro Ile Ala Asn Ile Pro Glu Glu Leu Thr Pro Val Ala Thr Asp Lys
        370                 375                 380

Tyr Leu Gly Gly Thr Asp Asp Pro Val Lys Lys Lys Asp Leu Phe Leu
385                 390                 395                 400

Asp Leu Met Gly Asp Val Val Phe Gly Val Pro Ser Val Thr Val Ala
                405                 410                 415

Arg Gln His Arg Asp Ala Gly Ala Pro Thr Tyr Met Tyr Glu Phe Gln
                420                 425                 430

Tyr Arg Pro Ser Phe Ser Ser Asp Lys Lys Pro Lys Thr Val Ile Gly
        435                 440                 445

Asp His Gly Asp Glu Ile Phe Ser Val Phe Gly Phe Pro Leu Leu Lys
        450                 455                 460

Gly Asp Ala Pro Glu Glu Glu Val Ser Leu Ser Lys Thr Val Met Lys
465                 470                 475                 480

Phe Trp Ala Asn Phe Ala Arg Ser Gly Asn Pro Asn Gly Glu Gly Leu
                485                 490                 495

Pro His Trp Pro Met Tyr Asp Gln Glu Glu Gly Tyr Leu Gln Ile Gly
                500                 505                 510

Val Asn Thr Gln Ala Ala Lys Arg Leu Lys Gly Glu Glu Val Ala Phe
            515                 520                 525

Trp Asn Asp Leu Leu Ser Lys Glu Ala Ala Lys Lys Pro Pro Lys Ile
        530                 535                 540

Lys His Ala Glu Leu
545
```